(12) United States Patent
Lu et al.

(10) Patent No.: US 11,058,779 B2
(45) Date of Patent: Jul. 13, 2021

(54) SIRNA/NANOPARTICLE FORMULATIONS FOR TREATMENT OF MIDDLE-EAST RESPIRATORY SYNDROME CORONAVIRAL INFECTION

(71) Applicant: Sirnaomics, Inc., Gaithersburg, MD (US)

(72) Inventors: Patrick Y. Lu, Potomac, MD (US); Vera Simonenko, Gaithersburg, MD (US); Yibin Cai, Gaithersburg, MD (US); John Xu, Germantown, MD (US); David Evans, North Potomac, MD (US)

(73) Assignee: Sirnaomics, Inc., Gaithersburg, MD (US)

( * ) Notice: Subject to any disclaimer, the term of this patent is extended or adjusted under 35 U.S.C. 154(b) by 102 days.

(21) Appl. No.: 15/758,312

(22) PCT Filed: Sep. 7, 2016

(86) PCT No.: PCT/US2016/050590
§ 371 (c)(1),
(2) Date: Mar. 7, 2018

(87) PCT Pub. No.: WO2017/044507
PCT Pub. Date: Mar. 16, 2017

(65) Prior Publication Data
US 2019/0030187 A1    Jan. 31, 2019

Related U.S. Application Data

(60) Provisional application No. 62/215,565, filed on Sep. 8, 2015.

(51) Int. Cl.
*A61K 48/00* (2006.01)
*C12N 15/11* (2006.01)
(Continued)

(52) U.S. Cl.
CPC .......... *A61K 48/0066* (2013.01); *A61K 9/127* (2013.01); *A61K 9/5153* (2013.01);
(Continued)

(58) Field of Classification Search
CPC .............. A61K 48/0066; A61K 47/543; A61K 48/0008; A61K 9/127; A61K 31/14;
(Continued)

(56) References Cited

U.S. PATENT DOCUMENTS

2008/0070354 A1    3/2008  Jain et al.
2010/0204266 A1    8/2010  Ecker et al.
(Continued)

FOREIGN PATENT DOCUMENTS

| WO | 2011109698 A1 | 9/2011 |
| WO | 2015057966 A2 | 4/2015 |
| WO | 2015081155 A1 | 6/2015 |

OTHER PUBLICATIONS

Nur et al. (Interdiscip Sci Comput Life Sci, 2015 vol. 7:257-265, published online Jul. 30, 2015).*
(Continued)

*Primary Examiner* — Terra C Gibbs
(74) *Attorney, Agent, or Firm* — Edell, Shapiro & Finnan, LLC

(57) ABSTRACT

The present invention relates to compositions and methods for siRNA therapeutics for prevention and treatment of Middle East Respiratory Syndrome Corona Virus (MERS-CoV) infections. The compositions include a pharmaceutical composition comprising siRNA cocktails that target viral genes and pharmaceutically acceptable polymeric nanoparticle carriers and liposomal nanoparticle carriers.

20 Claims, 15 Drawing Sheets

Specification includes a Sequence Listing.

(51) Int. Cl.
| | |
|---|---|
| *C07H 21/02* | (2006.01) |
| *C07H 21/04* | (2006.01) |
| *A61K 9/51* | (2006.01) |
| *A61K 9/127* | (2006.01) |
| *A61K 47/54* | (2017.01) |
| *A61P 31/14* | (2006.01) |
| *A61K 47/28* | (2006.01) |
| *C12N 15/113* | (2010.01) |
| *C12N 15/88* | (2006.01) |
| *B82Y 5/00* | (2011.01) |

(52) U.S. Cl.
CPC ............ *A61K 47/28* (2013.01); *A61K 47/543* (2017.08); *A61K 48/0008* (2013.01); *A61P 31/14* (2018.01); *C12N 15/1131* (2013.01); *B82Y 5/00* (2013.01); *C12N 15/88* (2013.01); *C12N 2310/14* (2013.01); *C12N 2320/31* (2013.01); *C12N 2320/32* (2013.01)

(58) Field of Classification Search
CPC ................ C12N 15/1131; C12N 15/88; C12N 2310/14; C12N 2320/31; A61P 31/14
See application file for complete search history.

(56) References Cited

U.S. PATENT DOCUMENTS

2011/0275785 A1   11/2011   Mixson
2014/0235605 A1   8/2014   Shiffman et al.

OTHER PUBLICATIONS

GenBank Accession JX869059 (Dec. 2012). Human betacoronavirus 2c EMC/2012, complete genome.*
Wang et al. (Asian Biomedicine, 2013 vol. 7:463-475).*
Xia et al. (Virus Research, 2014, Epub Oct. 14, 2014 vol. 194:200-210).*
Li et al. (Nature Medicine, 2005 vol. 11:944-951).*
Mevel, M., et al., "DODAG: a Versatile New Cationic Lipid that Mediates Efficient Delivery of pDNA and siRNA", Journal of Controlled Release, vol. 143, pp. 222-232 (2010).
Yang, X., et al., "Proteolytic processing, deubiquitinase and interferon antagonist activities of Middle East respiratory syndrome coronavirus papain-like protease", Journal of General Virology,, vol. 95, pp. 614-626 (2014).
Search report in corresponding International Application No. PCT/US16/50590, dated Apr. 6, 2017.

* cited by examiner

Figure 1. The genome structure of MERS-CoV
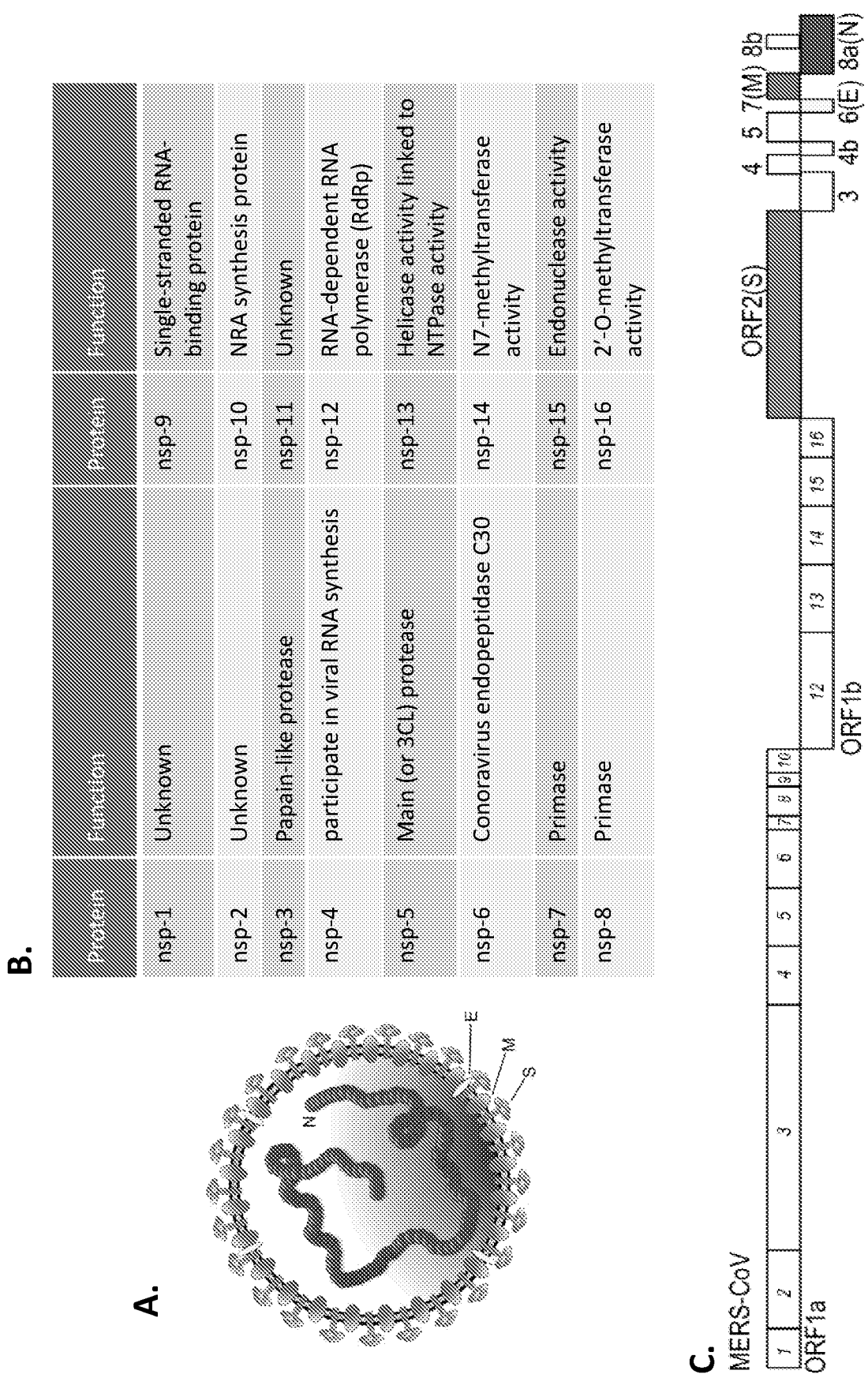

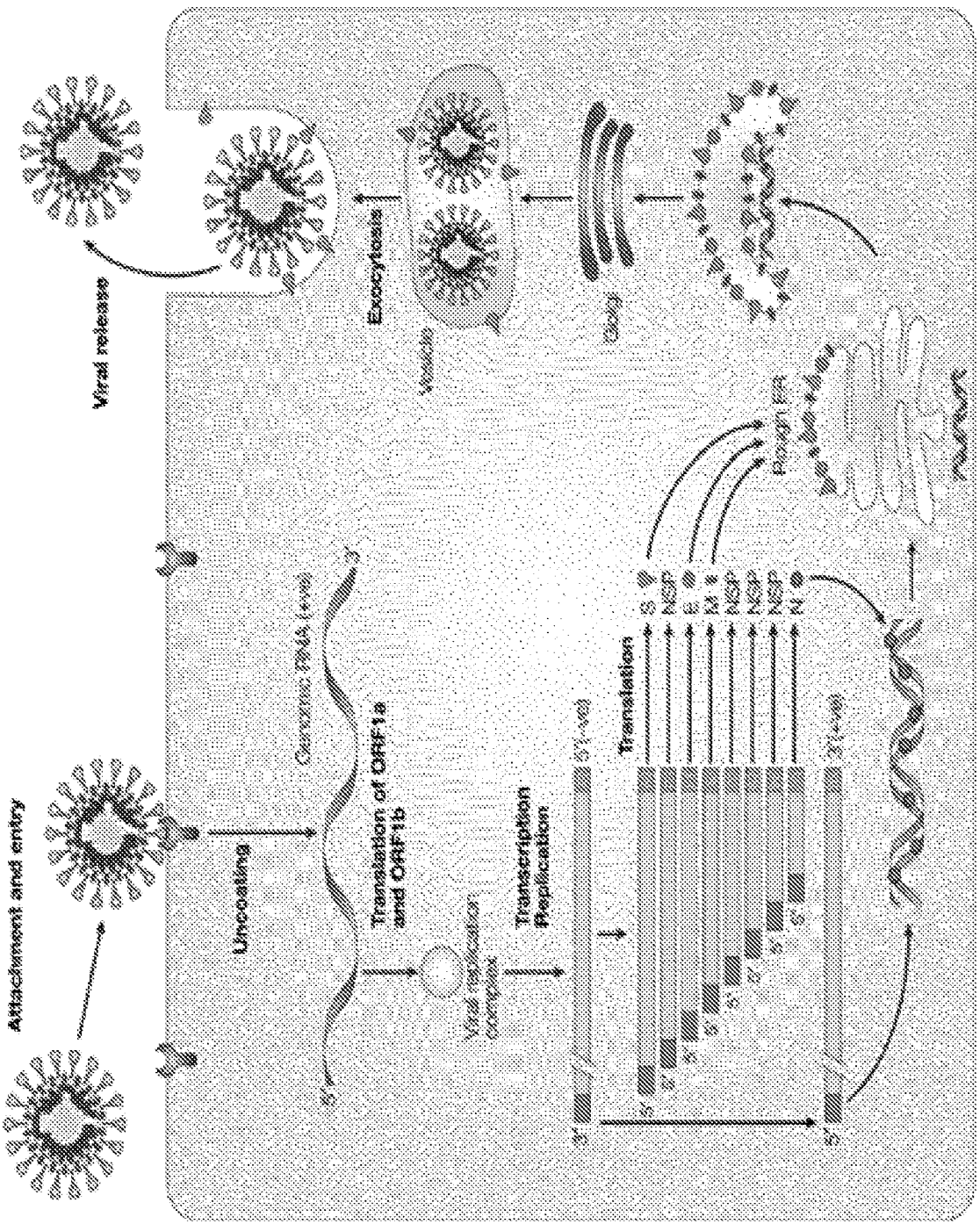
Figure 2. The life cycle of MERS

Figure 3. Sequences of siRNA design Targeting three critical genes for the life cycle of MERS virus MERS-CoV ORF1a — PL$^{pro}$ — RdRp — ORF1b — Spike ORF2(S) — 3, 4, 4b, 5, 6(E), 7(M), 8a(N), 8b MP1: CGCAAUACGUAAAGCUAAAGAUUAU
MP2: GGGUGUGAUUAAUCUAAGAAGUUU
MP3: CGCACUAAUGGUGUUACAAUCUU
MP4: GGCUUCAUUUAUUUCAAAGAAUU
MP5: GCGCUUUACAAAUCUAGAUAAGUU
MP6: CGCAUUGCAUGCCGUAAGUGUAAUU MRR1: CCCAGUGUUAUUGGUGUUUAUCAUA
MRR2: GGGAUUCAUGCUAAACAUUGUA
MRR3: GGGUGCUAAUGGCAACAAGAUUGUU
MRR4: CCCCAAAUUGUUGAUAAAUACUAU
MRR5: CGGUUGCUUUGUAGAUGAUAUCGUU MSP1: GGCCGUACAUAUUCUAACAUAACUA
MSP2: GCCGUACAUAUUCUAACAUAACUAU
MSP3: CCGAAGAUGAGAUUUAGAGUGUU
MSP4: CCCAGUUUAAUAUAAACAGUCCUU
MSP5: GGCUUCACUACAACUAAUGAGCUU
MSP6: CCCCUGUUAAUGGCUACUUUAUAA
MSP7: CCCUGUUAAUGGCUACUUUAUAAA
MSP8: GCCGCAUAAGGUUCAUGUUCACUA

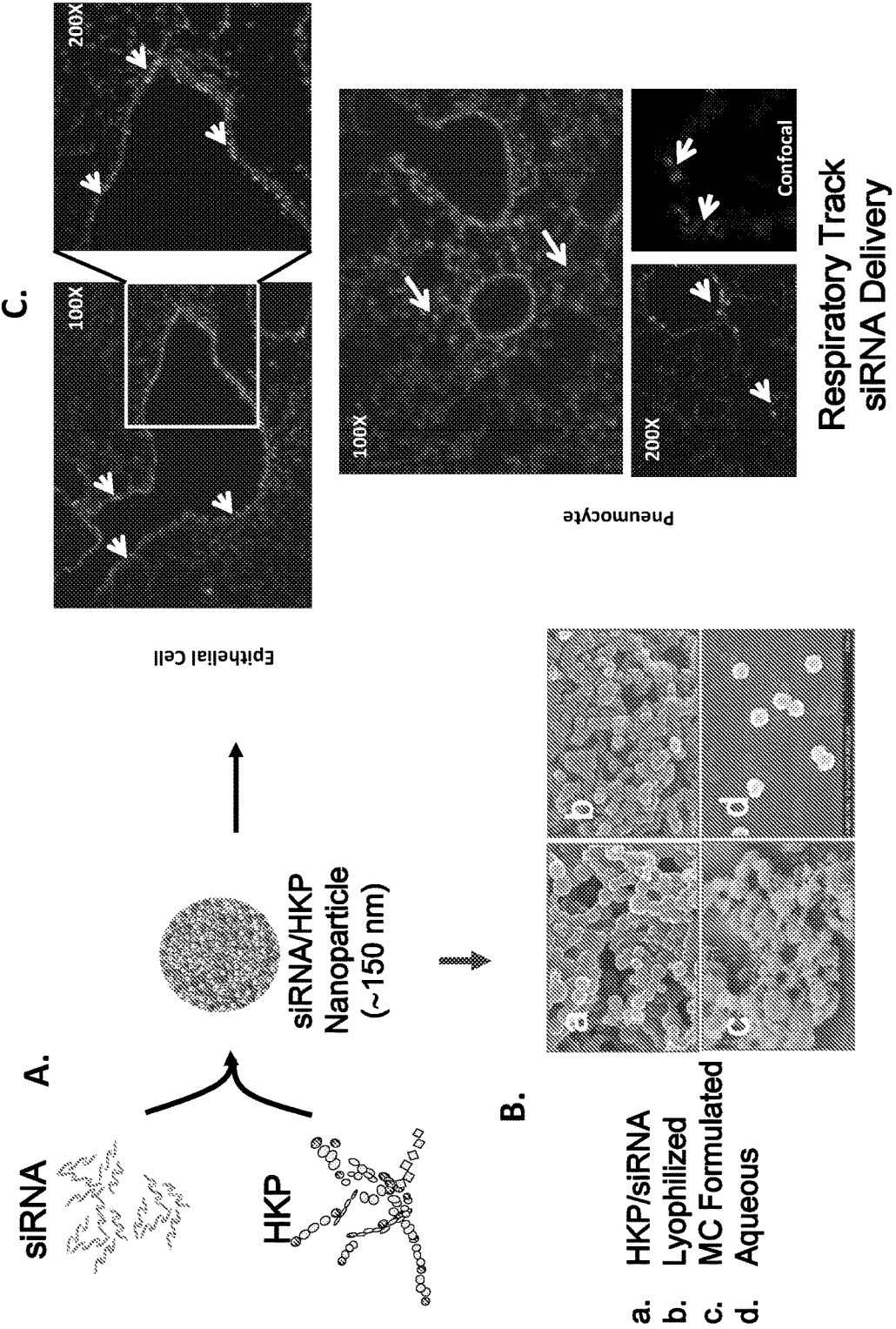
Figure 4. Histidine-Lysine Polymer for siRNA pulmonary delivery

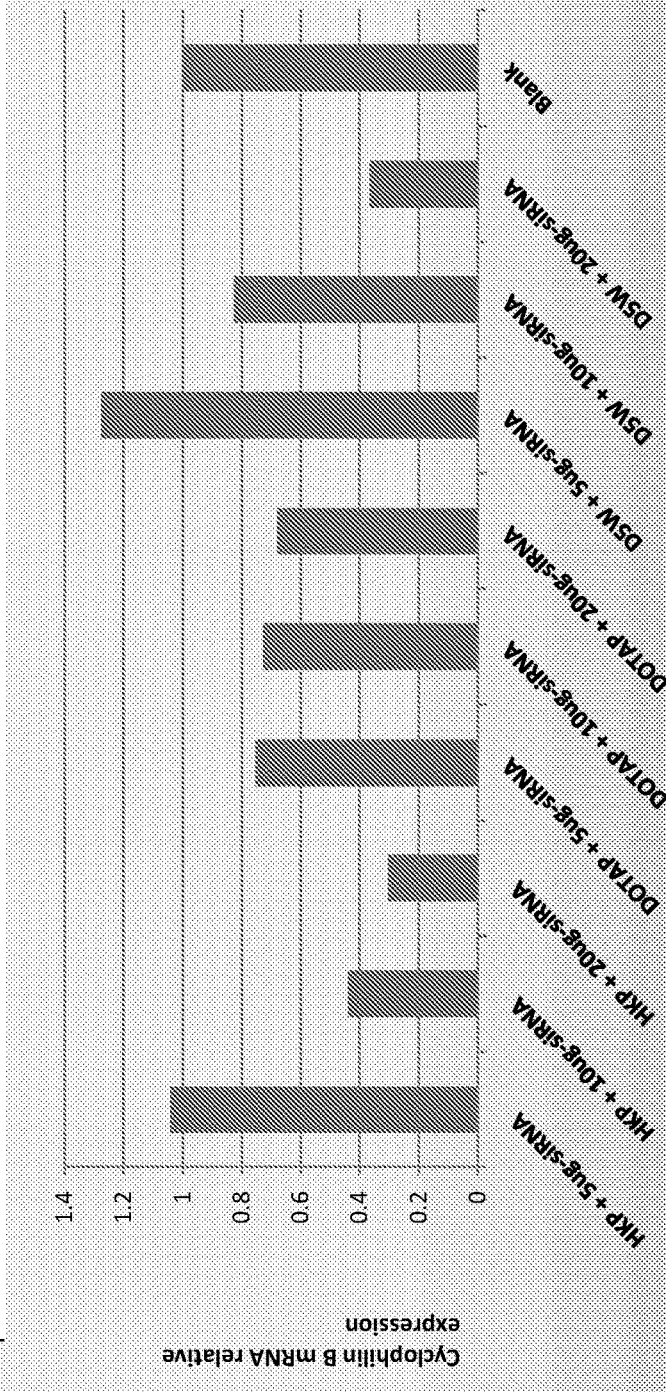
Figure 5. Histidine-Lysine Polymer is better than DOTAP and D5W in terms of siRNA pulmonary delivery

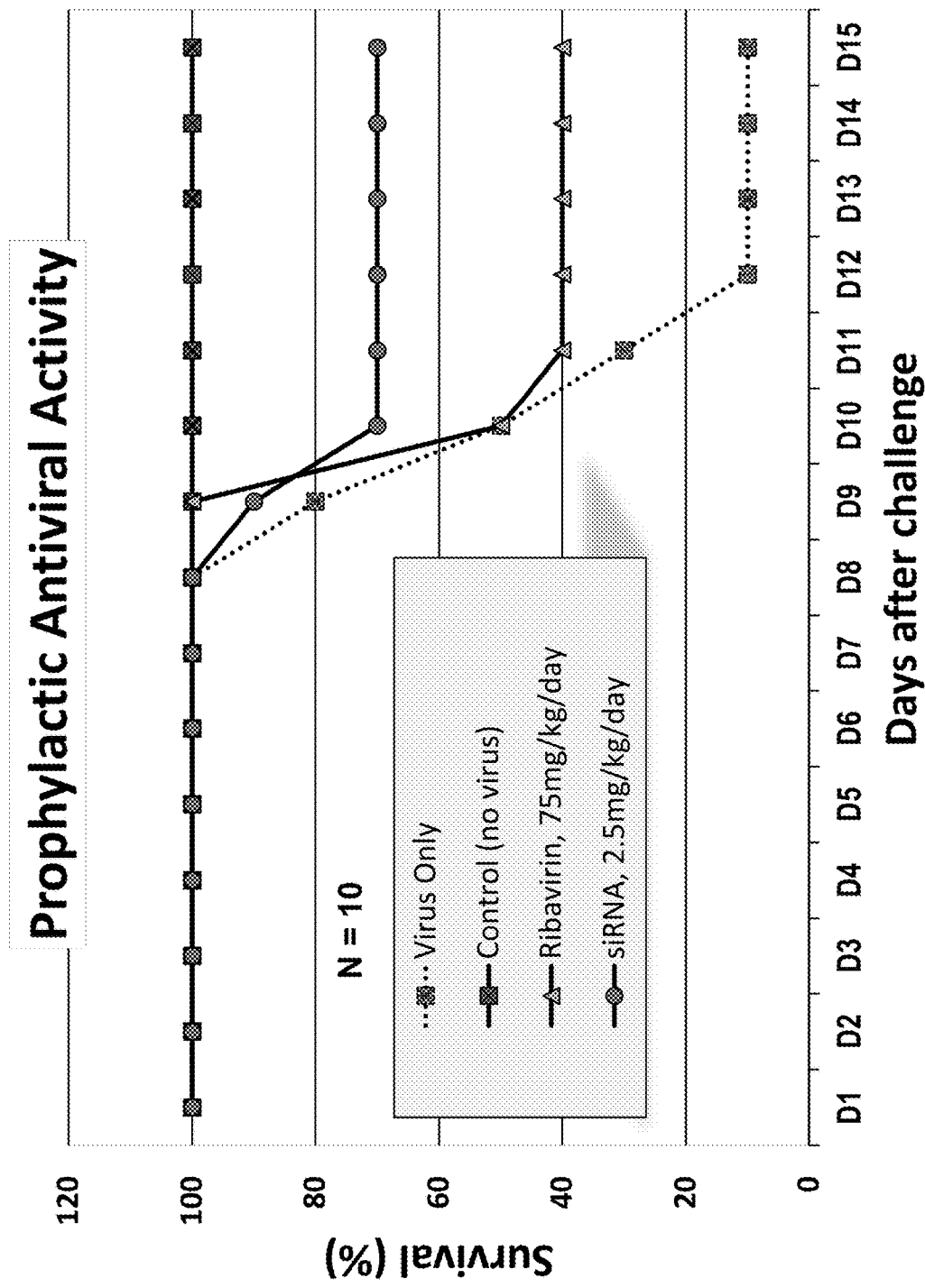
Figure 6. Histidine-Lysine Polymer for siRNA
Intraperitoneal delivery as a prophylaxis

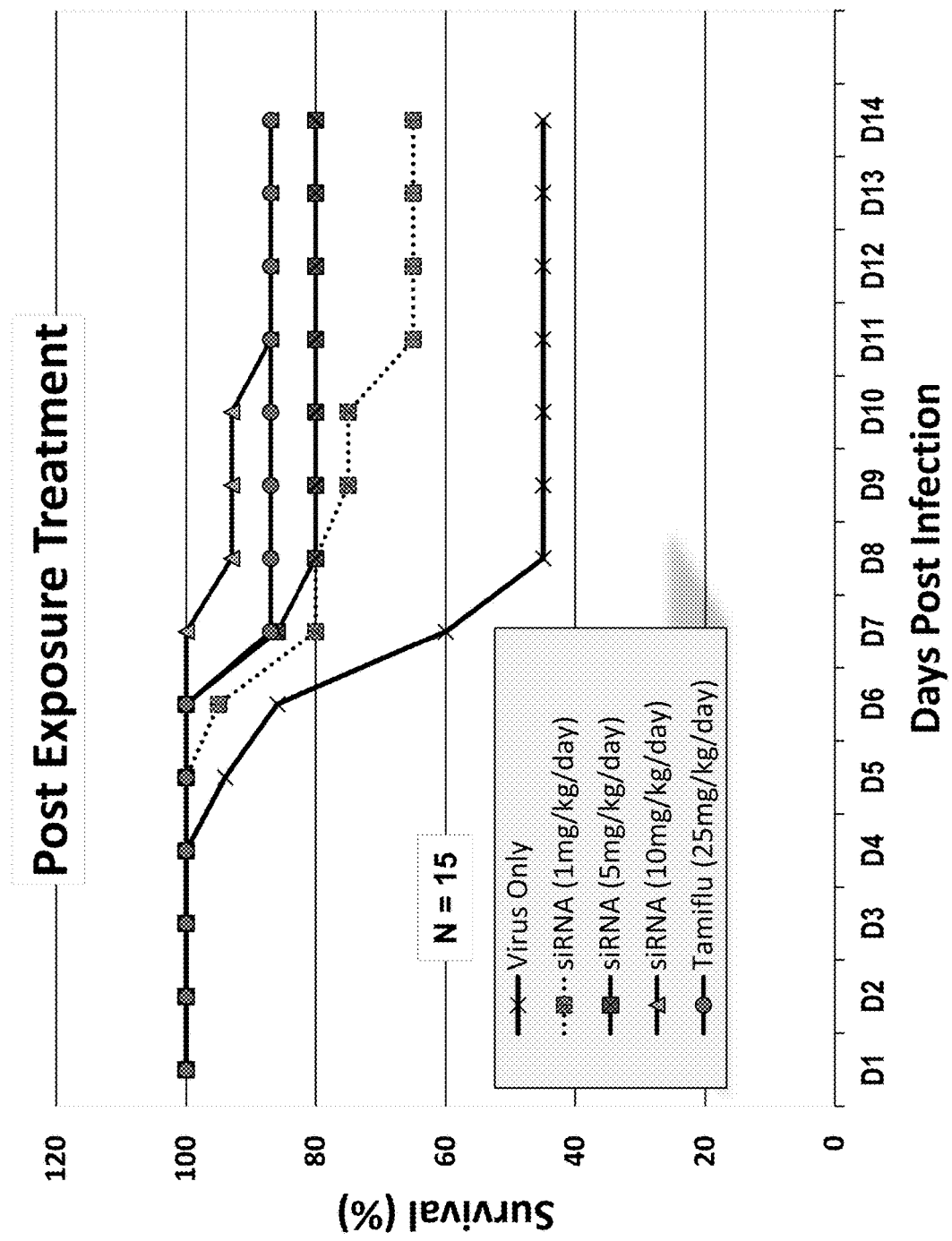
Figure 7. Histidine-Lysine Polymer for siRNA Intraperitoneal delivery as a therapeutics

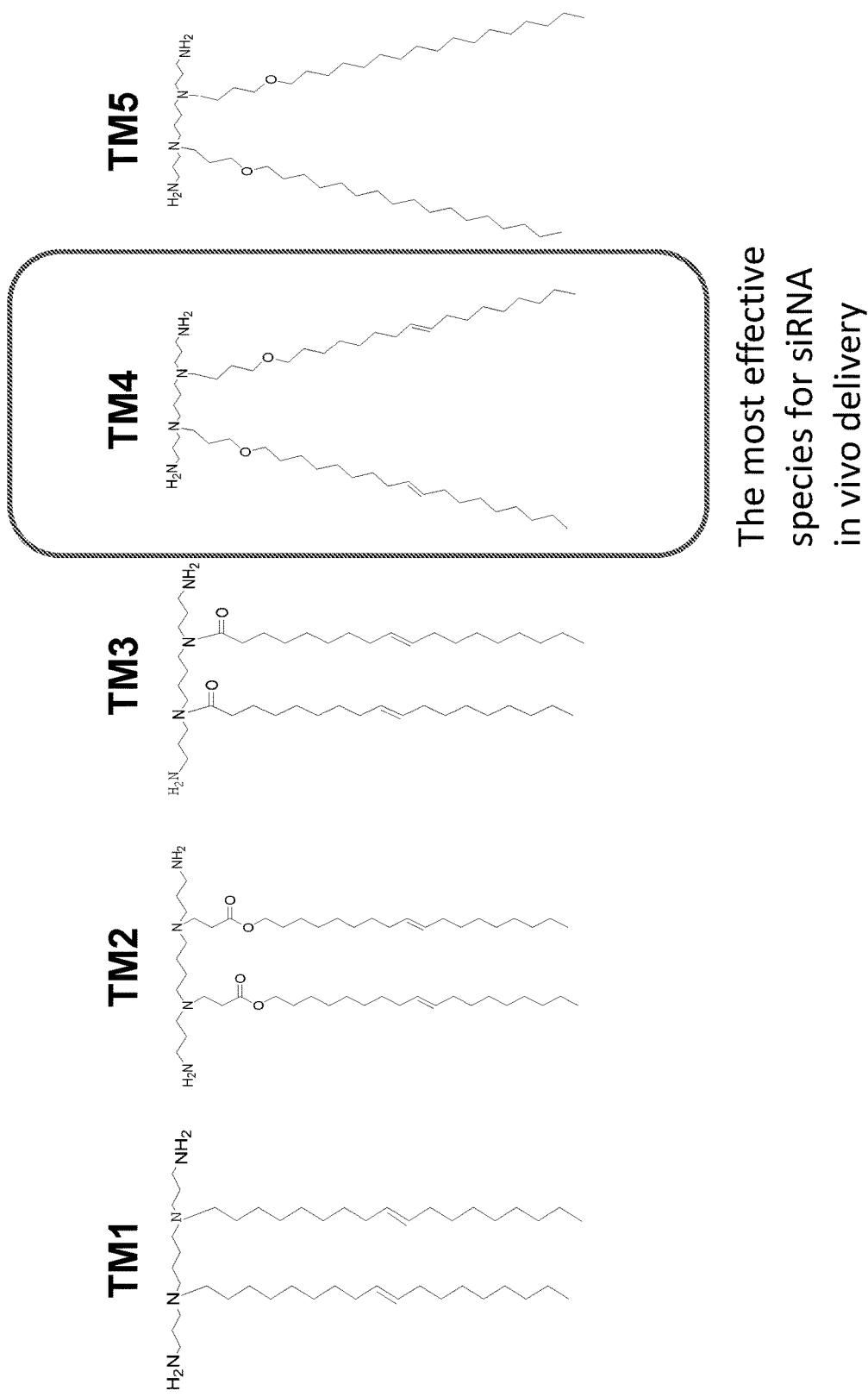
Figure 8. Structures of Spermine-Lipid Conjugates (SLiC) species

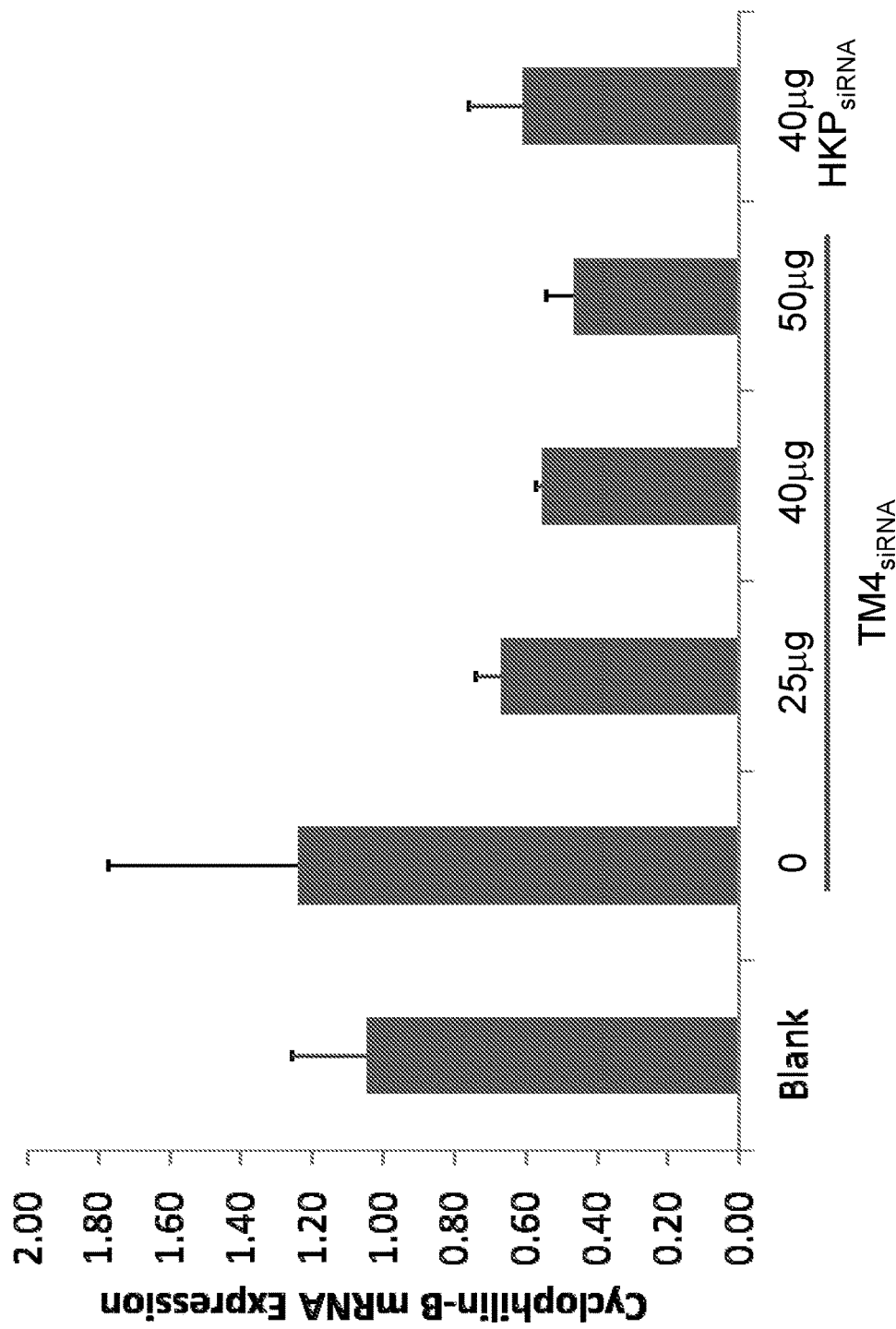
Figure 9. Target gene expression after SLiC-mediated siRNA delivery

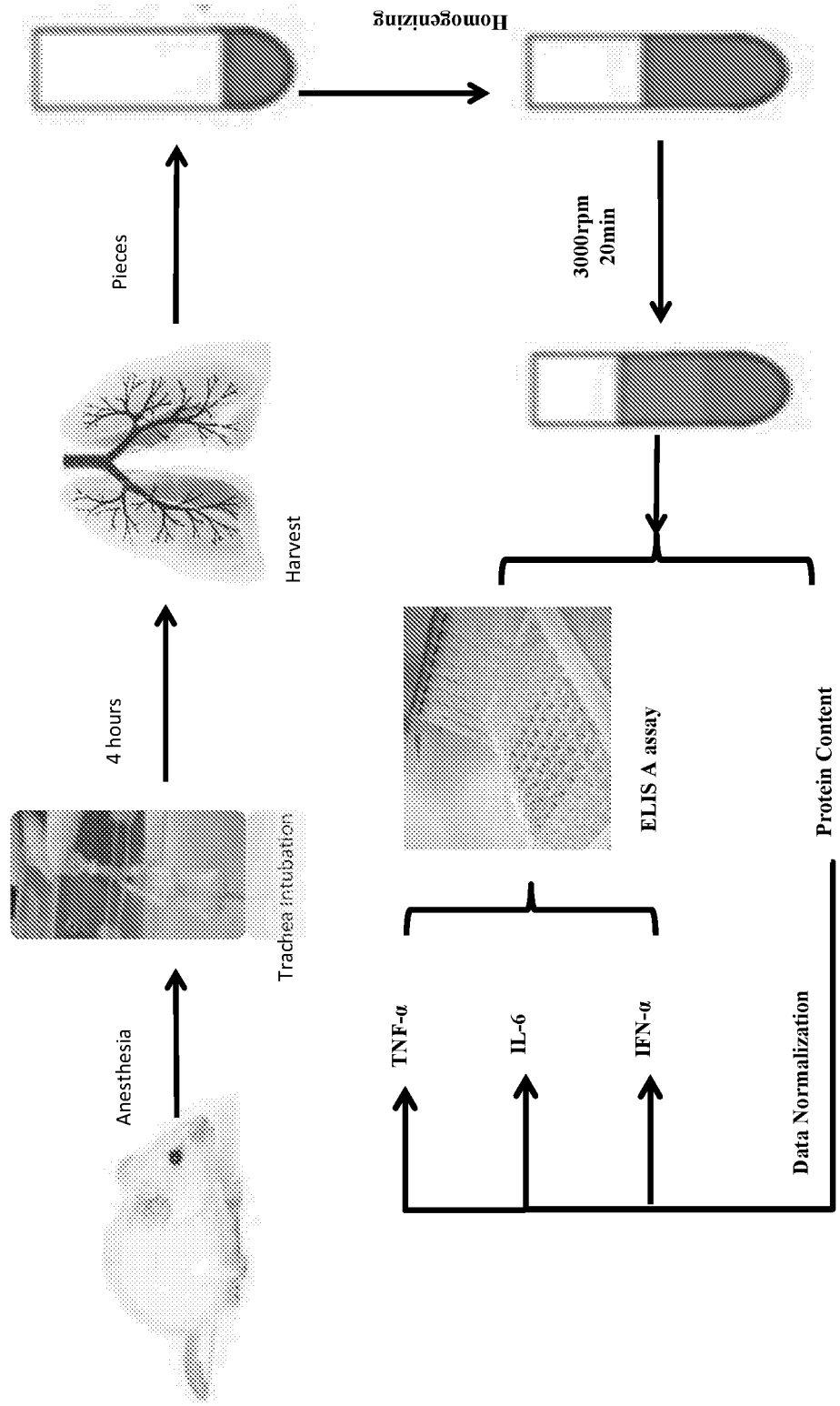
Figure 10. Evaluation of Cytokine Response after Histidine-Lysine Polymer mediate siRNA delivery in the Lung

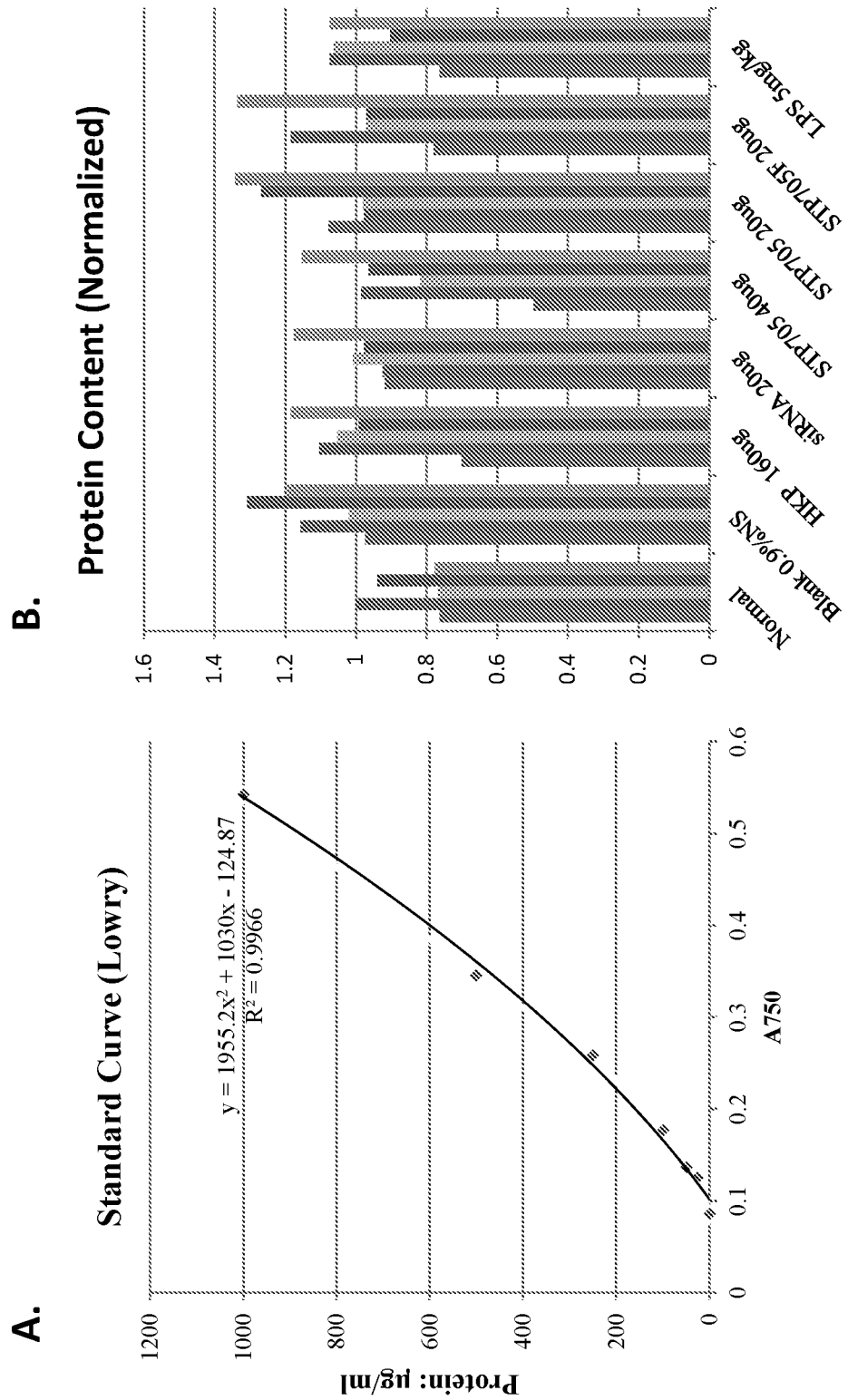
Figure 11. Methods for Evaluation of Cytokine Response after Histidine-Lysine Polymer mediate siRNA delivery in the Lung

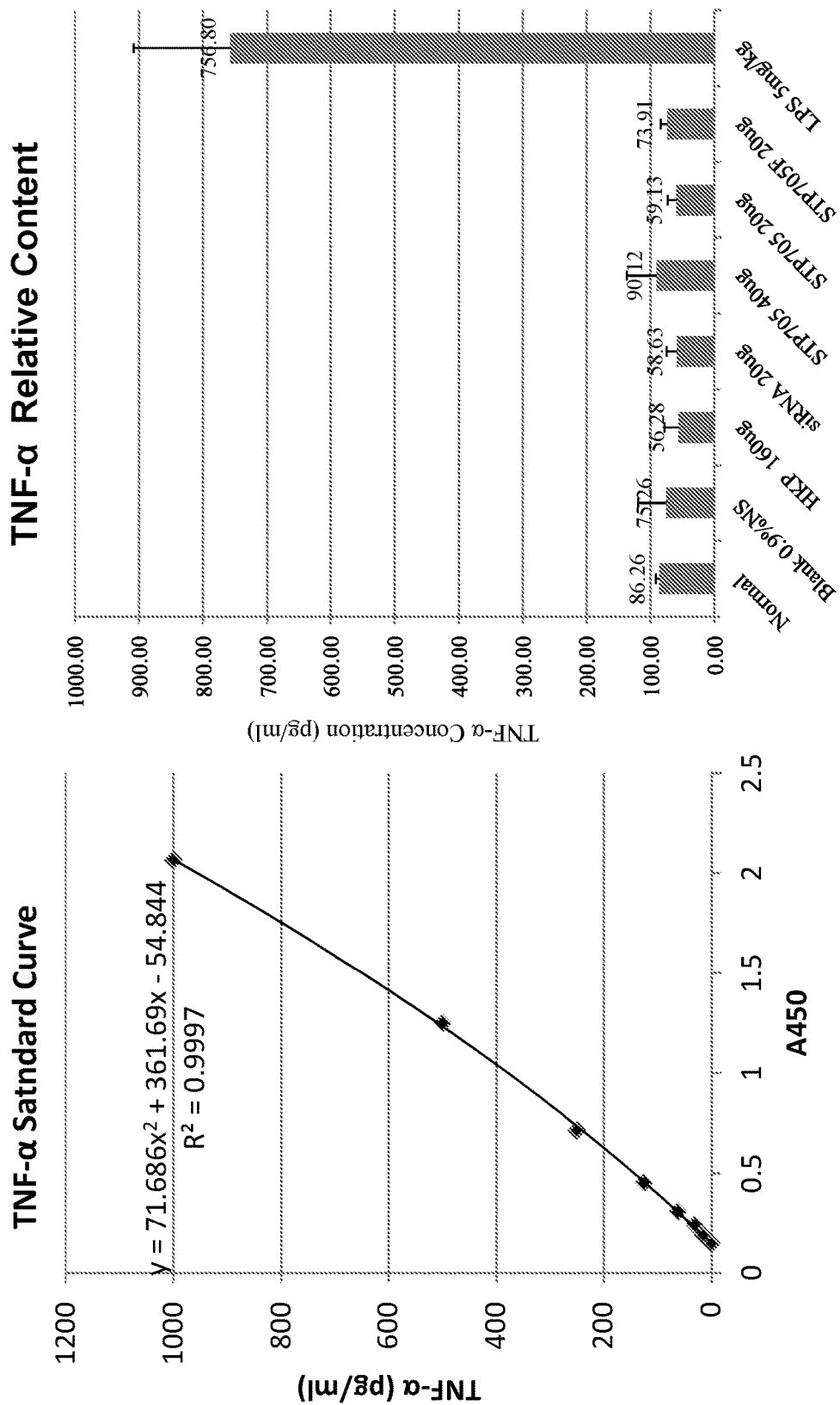
Figure 12. TNF-α Expression after Histidine-Lysine Polymer mediate siRNA delivery in the Lung Figure 13. IL-6 Expression after Histidine-Lysine Polymer mediate siRNA delivery in the Lung
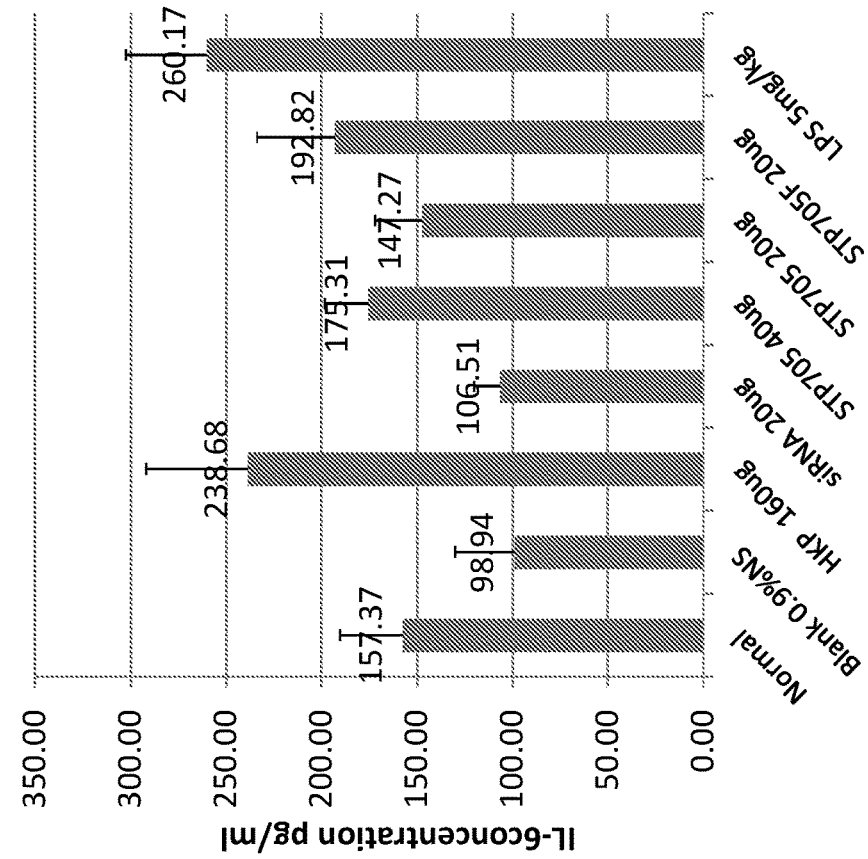
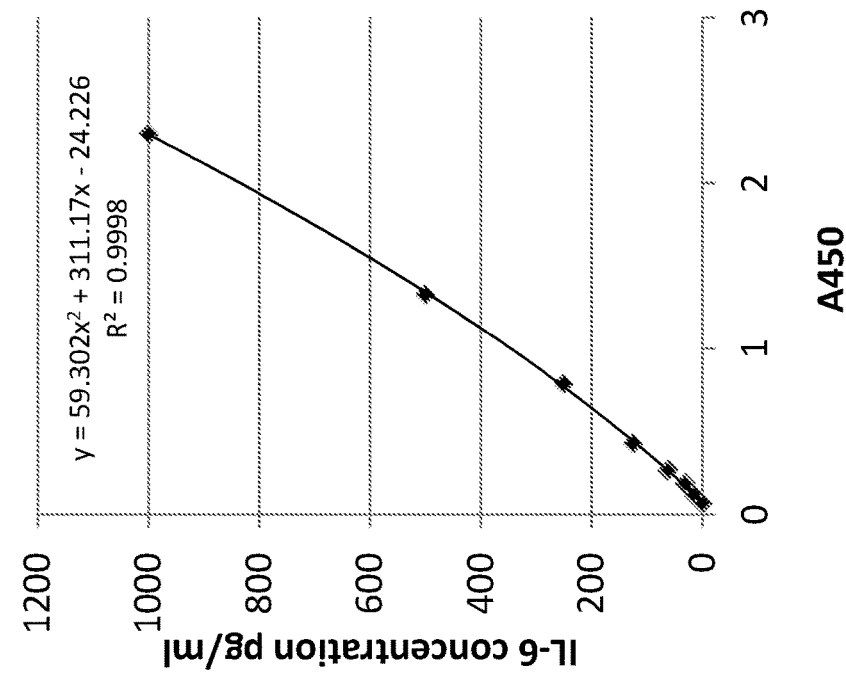

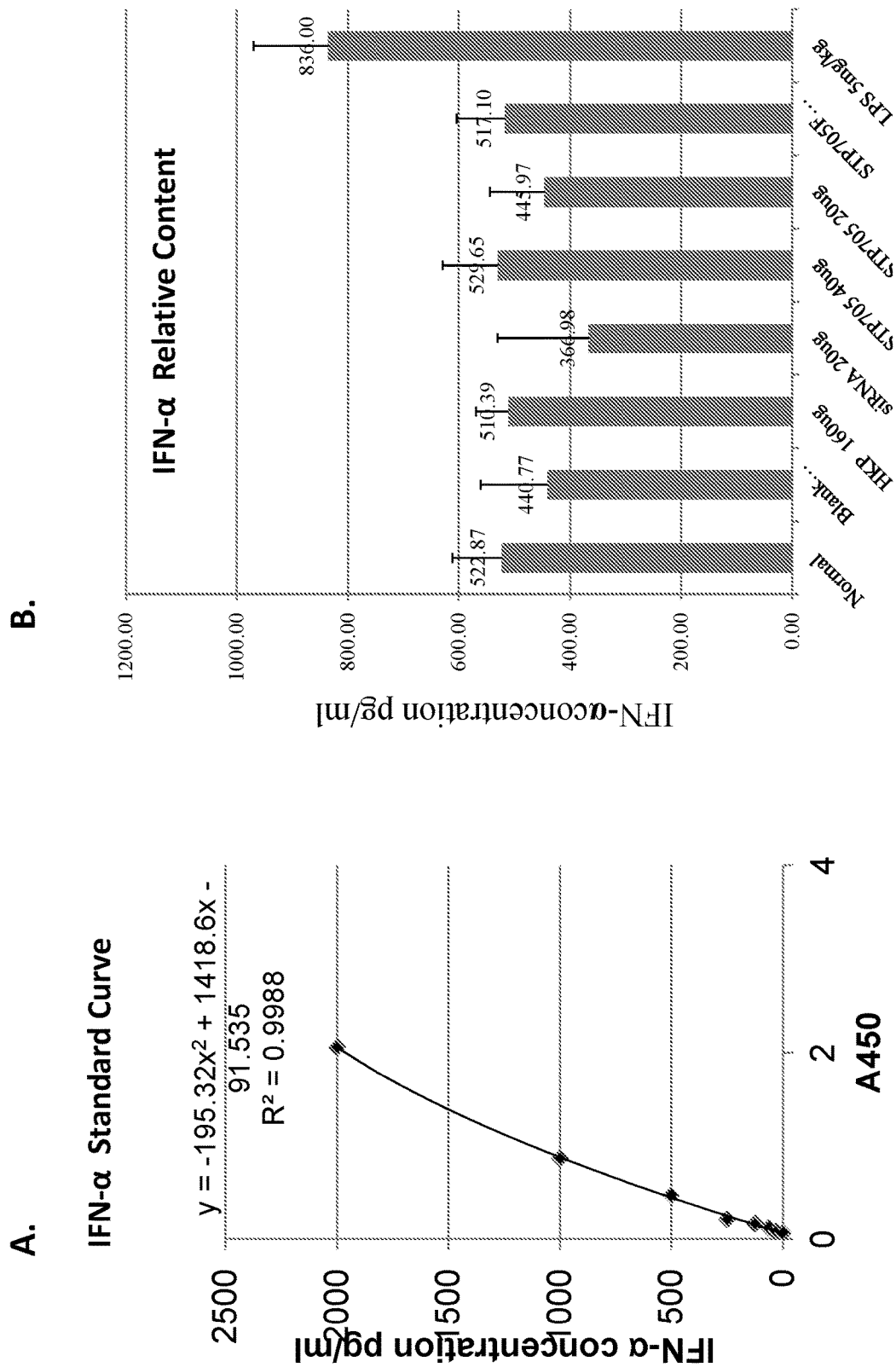
Figure 14. IFN-α Expression after Histidine-Lysine Polymer mediate siRNA delivery in the Lung Figure 15. The siRNA therapeutic formulation solution can be administered though the areosolation with a nebulizer great page

SEQUENCE LISTING

```
<160> NUMBER OF SEQ ID NOS: 1059

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cgcaauacgu aaagcuaaag auuau                                              25

<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ggguguugau uauacuaaga aguuu                                              25

<210> SEQ ID NO 3
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cgcauaaugg ugguuacaau ucuu                                               24

<210> SEQ ID NO 4
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ggcuucauuu uauuucaaag aauuu                                              25

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
gcgcuuuuac aaaucuagau aaguu                                        25

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cgcauugcau gccguaagug uaauu                                        25

<210> SEQ ID NO 7
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cccaguguua uugguguuua ucaua                                        25

<210> SEQ ID NO 8
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gggauuucau gcuuaaaaca uugua                                        25

<210> SEQ ID NO 9
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gggugcuaau ggcaacaaga uuguu                                        25

<210> SEQ ID NO 10
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ccccaaauuu guugauaaau acuau                                        25

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
```
cgguugcuuu guagaugaua ucguu                                              25

<210> SEQ ID NO 12
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ggccguacau auucuaacau aacua                                              25

<210> SEQ ID NO 13
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ccgaagauga gauuuagag ugguu                                               25

<210> SEQ ID NO 14
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cccaguuuaa uuauaaacag uccuu                                              25

<210> SEQ ID NO 15
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ggcuucacua caacuaauga agcuu                                              25

<210> SEQ ID NO 16
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ccccuguuaa uggcuacuuu auuaa                                              25

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
cccuguuaau ggcuacuuua uuaaa                                              25

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gccgcauaag guucauguuc acuaa                                              25

<210> SEQ ID NO 19
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gggguugauu auacuaagaa guuu                                               24

<210> SEQ ID NO 20
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gggauuucau gcuuaaaaca uugua                                              25

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
cccaguguua uugguguuua ucaua                                              25

<210> SEQ ID NO 22
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cgcaauacgu aaagcuaaag auau                                               24

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys His His His Lys His His His Lys His His His Lys His His His His

Lys

<210> SEQ ID NO 24
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ggcucauugc uugugaaaau ccauu                                          25

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gcuugugaaa auccauucau gguua                                          25

<210> SEQ ID NO 26
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26 ccaucaugg uuaaccaauu ggcuu                                           25

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
cgaacuuguc acaggaaagc aaaau                                          25

<210> SEQ ID NO 28
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gcaaaauauu cuccugcgca aguau                                          25

<210> SEQ ID NO 29
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29

```
ccccauucca cuaugagcga gacaa                                              25

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ggcaaauaug cccagaaucu gcuua                                              25

<210> SEQ ID NO 31
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gcaaauaugc ccagaaucug cuuaa                                              25

<210> SEQ ID NO 32
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
cccagaaucu gcuuaagaag uugau                                              25

<210> SEQ ID NO 33
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ccagaaucug cuuaagaagu ugauu                                              25

<210> SEQ ID NO 34
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gcuuaagaag uugauuggcg gugau                                              25

<210> SEQ ID NO 35
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
```
cggugauguc acuccaguug accaa         25

<210> SEQ ID NO 36
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ggugauguca cuccaguuga ccaau         25

<210> SEQ ID NO 37
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ggaaaaccca uuagugccua cgcau         25

<210> SEQ ID NO 38
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cccauuagug ccuacgcauu uuuaa         25

<210> SEQ ID NO 39
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ccauuagugc cuacgcauuu uuaau         25

<210> SEQ ID NO 40
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ggauggaaua accaaacugg cugau         25

<210> SEQ ID NO 41
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
cgucgcagca cgugcugaug acgaa         25

<210> SEQ ID NO 42
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 42
gcugaugacg aaggcuucau cacau                                    25

<210> SEQ ID NO 43
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 43
cguuccauau ccuaagcaau cuauu                                    25

<210> SEQ ID NO 44
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 44
ccauauccua agcaaucuau uuuua                                    25

<210> SEQ ID NO 45
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 45
ccuaagcaau cuauuuuac uauua                                     25

<210> SEQ ID NO 46
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 46
ccuccucacu auuuuacucu uggau                                    25

<210> SEQ ID NO 47
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 47
cguuucugac uugucccuca aacaa                                    25

<210> SEQ ID NO 48
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gguaaggagu cacuugagaa cccaa                                            25

<210> SEQ ID NO 49
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ccaaccuaca uuuaccacuc cgcau                                            25

<210> SEQ ID NO 50
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ccuacauuua ccacuccgca uucau                                            25

<210> SEQ ID NO 51
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gcuauccaag gguuugccug uggau                                            25

<210> SEQ ID NO 52
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ggguuugccu guggaugugg ggcau                                            25

<210> SEQ ID NO 53
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gccuguggau guggggcauc auaua                                            25

```
<210> SEQ ID NO 54
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ggaugugggg caucauauac agcua                                           25

<210> SEQ ID NO 55
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ggcguagcuu acgccuacuu uggau                                           25

<210> SEQ ID NO 56
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gccuacuuug gaugugagga aggua                                           25

<210> SEQ ID NO 57
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ccuagagcua agucuguugu cucaa                                           25

<210> SEQ ID NO 58
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ccuuaacuuu gugggagagu ucguu                                           25

<210> SEQ ID NO 59
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
gggagaguuc guugucaacg auguu                                           25

<210> SEQ ID NO 60
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gccggcccau ucauggauaa ugcua                                           25

<210> SEQ ID NO 61
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ccggcccauu cauggauaau gcuau                                           25

<210> SEQ ID NO 62
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
cggcccauuc auggauaaug cuauu                                           25

<210> SEQ ID NO 63
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ggcccauuca uggauaaugc uauua                                           25

<210> SEQ ID NO 64
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
gcccauucau ggauaaugcu auuaa                                           25

<210> SEQ ID NO 65
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
cccauucaug gauaaugcua uuaau                                           25

<210> SEQ ID NO 66
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
gcuauuaaug uuggugguac aggau                                          25

<210> SEQ ID NO 67
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
cgccauuacu gcaccuuaug uaguu                                          25

<210> SEQ ID NO 68
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gcucacagcg uguuguacag aguuu                                          25

<210> SEQ ID NO 69
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
gcguguugua cagaguuuuu ccuua                                          25

<210> SEQ ID NO 70
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
cguguuguac agaguuuuuc cuuau                                          25

<210> SEQ ID NO 71
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ggcgacuuua ugucuacaau uauua                                          25

<210> SEQ ID NO 72
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 72
ccaaacugcu guuaguaagc uucua                                               25

<210> SEQ ID NO 73
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
gcuguuagua agcuucuaga uacau                                               25

<210> SEQ ID NO 74
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
gcaacauuua acuucuuguu agauu                                               25

<210> SEQ ID NO 75
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ccuaugugua cacuucacaa ggguu                                               25

<210> SEQ ID NO 76
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
ggaaccuauu acugugucac cacua                                               25

<210> SEQ ID NO 77
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
gguugaaacu guguggguc aacuu                                                25

<210> SEQ ID NO 78
<211> LENGTH: 25
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 78
gcaaacuaau augcauaguc cugau                                          25

<210> SEQ ID NO 79
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
ggugacuaug ucauuauuag ugaaa                                          25

<210> SEQ ID NO 80
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
gggaggugca ccuguaaaaa aagua                                          25

<210> SEQ ID NO 81
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
cgaguacaac auucaugcug uauua                                          25

<210> SEQ ID NO 82
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
gcuguauuag acacacuacu ugcuu                                          25

<210> SEQ ID NO 83
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ggaguuugcu gacguaguaa aggaa                                          25

<210> SEQ ID NO 84
<211> LENGTH: 25
<212> TYPE: RNA
<220> FEATURE:

```
<223> OTHER INFORMATION: Description of Artificial Sequence: Synthetic
      oligonucleotide

<400> SEQUENCE: 84
gcguggaaug ccgauuccag auuuu                                              25

<210> SEQ ID NO 85
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
ggaaugccga uuccagauuu ugauu                                              25

<210> SEQ ID NO 86
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
ccagauuuug auuuagacga uuuua                                              25

<210> SEQ ID NO 87
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
cgauuuuauu gacgcaccau gcuau                                              25

<210> SEQ ID NO 88
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
cccgucgagu gugacgagga guguu                                              25

<210> SEQ ID NO 89
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
cgagugugac gaggaguguu cugaa                                              25

<210> SEQ ID NO 90
<211> LENGTH: 25
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 90
ggcuucagau uuagaagaag gugaa                                         25

<210> SEQ ID NO 91
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
gcuucagauu uagaagaagg ugaau                                         25

<210> SEQ ID NO 92
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
cgacgagugg gcugcugcag uugau                                         25

<210> SEQ ID NO 93
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
cgagugggcu gcugcaguug augaa                                         25

<210> SEQ ID NO 94
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
gggcugcugc aguugaugaa gcguu                                         25

<210> SEQ ID NO 95
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
gcaagaagaa gcacaaccag uagaa                                         25

<210> SEQ ID NO 96
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 96
ccaguagaag uaccuguuga agaua                                          25

<210> SEQ ID NO 97
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
gcagguuguc auagcugaca ccuua                                          25

<210> SEQ ID NO 98
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
gguuauuaca gagugcguua ccaua                                          25

<210> SEQ ID NO 99
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ggcgguggua ucgcuggugc uauua                                          25

<210> SEQ ID NO 100
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
gcggugguau cgcuggugcu auuaa                                          25

<210> SEQ ID NO 101
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
cggugguauc gcuggugcua uuaau                                          25

<210> SEQ ID NO 102
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 102
gcuggugcua uuaaugcggc uucaa                                          25

<210> SEQ ID NO 103
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
gcggcuucaa aagggggcugu ccaaa                                         25

<210> SEQ ID NO 104
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
cggcuucaaa aggggcuguc caaaa                                          25

<210> SEQ ID NO 105
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
ggcuucaaaa ggggcuguuc aaaaa                                          25

<210> SEQ ID NO 106
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
gccguuacaa guaggagauu caguu                                          25

<210> SEQ ID NO 107
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
cguaggccca gaugcccgcg cuaaa                                          25

<210> SEQ ID NO 108
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
```
cccagaugcc cgcgcuaaac aggau                                    25

<210> SEQ ID NO 109
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
ggcuaugaau gcauaccuc uugua                                     25

<210> SEQ ID NO 110
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
ccagcugugu cuuuugauua ucuua                                    25

<210> SEQ ID NO 111
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
gcugugucuu uugauuaucu uauua                                    25

<210> SEQ ID NO 112
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
cgucguuaau ucccaagaug ucuau                                    25

<210> SEQ ID NO 113
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
ggcgcaauac guaaagcuaa agauu                                    25

<210> SEQ ID NO 114
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gcgcaauacg uaaagcuaaa gauua                                          25

<210> SEQ ID NO 115
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
cguaaagcua aagauuaugg uuuua                                          25

<210> SEQ ID NO 116
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gcuaaagauu augguuuuac uguuu                                          25

<210> SEQ ID NO 117
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
gcacagacaa cucugcuaac acuaa                                          25

<210> SEQ ID NO 118
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
ggaacaaggg uguugauuau acuaa                                          25

<210> SEQ ID NO 119
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
cgucuaagga cacuuuagau gauau                                          25

<210> SEQ ID NO 120
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
ggacacuuua gaugauaucu uacaa                                          25

```
<210> SEQ ID NO 121
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gcuaauaagu cuguuggua uauau                                          25

<210> SEQ ID NO 122
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gguauuauau cuaugccuuu gggau                                         25

<210> SEQ ID NO 123
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123 ccuugggau augugucuca ugguu                                          25

<210> SEQ ID NO 124
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gcccuacgug ugucuccuag cuaau                                         25

<210> SEQ ID NO 125
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
cccuacgugu gucuccuagc uaaua                                         25

<210> SEQ ID NO 126
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
ccuacgugug ucuccuagcu aauaa                                         25
```

```
<210> SEQ ID NO 127
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gcuaauaaag agcaagaagc uauuu                                               25

<210> SEQ ID NO 128
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
gcaagaagcu auuugaugu cugaa                                                25

<210> SEQ ID NO 129
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gcuauuuuga ugucugaaga cguua                                               25

<210> SEQ ID NO 130
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
cguuaaguua aacccuucag aagau                                               25

<210> SEQ ID NO 131
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
cguccgcacu aauggugguu acaau                                               25

<210> SEQ ID NO 132
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
cgcacuaaug gugguuacaa uucuu                                               25
```

```
<210> SEQ ID NO 133
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
ccugcauugg ucugaucaaa ccaua                                              25

<210> SEQ ID NO 134
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
ggauucacgc acgacacagc aguua                                              25

<210> SEQ ID NO 135
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
gcguuuucuu uaauggugcu gauau                                              25

<210> SEQ ID NO 136
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
cguuuucuuu aauggugcug auauu                                              25

<210> SEQ ID NO 137
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
gcagacaauu ugacugcuga ugaaa                                              25

<210> SEQ ID NO 138
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
ccuacuuucu uacacagauu cuauu                                              25

<210> SEQ ID NO 139
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
cgguuacuuc auaccgugcu ugcaa                                              25

<210> SEQ ID NO 140
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
gguuacuuca uaccgugcuu gcaaa                                              25

<210> SEQ ID NO 141
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
gcaugguuug gagagagugg ugcaa                                              25

<210> SEQ ID NO 142
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
gcuuguuguu acgugggugu gcaaa                                              25

<210> SEQ ID NO 143
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
cgugggugug caaacuguug aagau                                              25

<210> SEQ ID NO 144
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
gguugcugcu cucaggcaca ccaaa                                              25

<210> SEQ ID NO 145
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
gcugcucuca ggcacaccaa augaa                                         25

<210> SEQ ID NO 146
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
gcucucaggc acaccaaaug aaaaa                                         25

<210> SEQ ID NO 147
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ggugacaacc uccacggcgc cugau                                         25

<210> SEQ ID NO 148
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
gggcauugaa acggcuguug gccau                                         25

<210> SEQ ID NO 149
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
ggcauugaaa cggcuguugg ccauu                                         25

<210> SEQ ID NO 150
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gcauugaaac ggcuguuggc cauua                                         25

<210> SEQ ID NO 151
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 151
ccguuagcaa gacuucagac uggaa                                            25

<210> SEQ ID NO 152
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gcaagacuuc agacuggaag ugcaa                                            25

<210> SEQ ID NO 153
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
ggccaaaaau acaguagcga uugua                                            25

<210> SEQ ID NO 154
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gccaaaaaua caguagcgau uguaa                                            25

<210> SEQ ID NO 155
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ccaaaaauac aguagcgauu guaau                                            25

<210> SEQ ID NO 156
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
cguacgguau ucuuuggacg guaau                                            25

<210> SEQ ID NO 157
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 157
ggacgguaau uucagaacag agguu                                              25

<210> SEQ ID NO 158
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
cgguaauuuc agaacagagg uugau                                              25

<210> SEQ ID NO 159
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
cccgaccuau cugcuuucua uguua                                              25

<210> SEQ ID NO 160
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
ccgaccuauc ugcuuucuau guuaa                                              25

<210> SEQ ID NO 161
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
ccuaucugcu uucuauguua aggau                                              25

<210> SEQ ID NO 162
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
gcuuucuaug uuaaggaugg uaaau                                              25

<210> SEQ ID NO 163
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 163
ggauggUaaa uacuuuacaa gugaa                                           25

<210> SEQ ID NO 164
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
ccacccguaa cauauucacc agcua                                           25

<210> SEQ ID NO 165
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
cccguaacau auucaccagc uacaa                                           25

<210> SEQ ID NO 166
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ccguaacaua uucaccagcu acaau                                           25

<210> SEQ ID NO 167
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
cguaacauau ucaccagcua caauu                                           25

<210> SEQ ID NO 168
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ggacaaccug gcggugaugc uauua                                           25

<210> SEQ ID NO 169
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 169
ggcggugaug cuauuaguuu gaguu                                          25

<210> SEQ ID NO 170
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
gcggugaugc uauuaguuug aguuu                                          25

<210> SEQ ID NO 171
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
cggugaugcu auuaguuuga guuuu                                          25

<210> SEQ ID NO 172
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
ggugaugcua uuaguuugag uuuua                                          25

<210> SEQ ID NO 173
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
cggcgaugug uuguuggcug aguuu                                          25

<210> SEQ ID NO 174
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
gcugaguuug acacuuauga cccua                                          25

<210> SEQ ID NO 175
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 175
ggugccaugu auaaaggcaa accaa                                            25

<210> SEQ ID NO 176
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
gcaucuuaug auacuaaucu uaaua                                            25

<210> SEQ ID NO 177
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
cguagccccc auugaacucg aaaau                                            25

<210> SEQ ID NO 178
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
gcccccauug aacucgaaaa uaaau                                            25

<210> SEQ ID NO 179
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
cccccauuga acucgaaaau aaauu                                            25

<210> SEQ ID NO 180
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
ccuuucguga aggacaaugu caguu                                            25

<210> SEQ ID NO 181
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 181
cgugaaggac aaugucaguu ucguu                                          25

<210> SEQ ID NO 182
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
ggacaauguc aguuucguug cugau                                          25

<210> SEQ ID NO 183
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
cccuaaguau caagucauug ucuua                                          25

<210> SEQ ID NO 184
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
ccuaaguauc aagucauugu cuuaa                                          25

<210> SEQ ID NO 185
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
gcacaccguu gagucaggug auauu                                          25

<210> SEQ ID NO 186
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
cguugaguca ggugauauua acguu                                          25

<210> SEQ ID NO 187
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
```

```
ggugauauua acguuguugc agcuu                                              25
```

<210> SEQ ID NO 188
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188

```
gggcuucauu uuauuucaaa gaauu                                              25
```

<210> SEQ ID NO 189
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189

```
gcuaccacug cuguagguag uugua                                              25
```

<210> SEQ ID NO 190
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190

```
ccacugcugu agguaguugu auaaa                                              25
```

<210> SEQ ID NO 191
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191

```
ggcauauuga caggcuguuu uaguu                                              25
```

<210> SEQ ID NO 192
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192

```
gcauauugac aggcuguuuu aguuu                                              25
```

<210> SEQ ID NO 193
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
gcuuccacua gcuuacuuua gugau                                              25

<210> SEQ ID NO 194
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
ccacuagcuu acuuuaguga uucaa                                              25

<210> SEQ ID NO 195
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
ccacagaggu uaaagugagu gcuuu                                              25

<210> SEQ ID NO 196
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
ggcguuguga cagguaaugu uguaa                                              25

<210> SEQ ID NO 197
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
gcguugugac agguaauguu guaaa                                              25

<210> SEQ ID NO 198
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
cguugugaca gguaauguug uaaaa                                              25

<210> SEQ ID NO 199
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
gcacugcugc uguugauuua aguau                                              25

<210> SEQ ID NO 200
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
gcugcuguug auuuaaguau ggaua                                    25

<210> SEQ ID NO 201
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
ccguguggau uggaaaucaa cccua                                    25

<210> SEQ ID NO 202
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
cgguuguuac uuauguuaug cacaa                                    25

<210> SEQ ID NO 203
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
cccaagguuu gaaaaguuc uacaa                                     25

<210> SEQ ID NO 204
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
ccaagguuug aaaaguucu acaaa                                     25

<210> SEQ ID NO 205
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
gcuugugacg gucuugcuuc agcuu                                    25

```
<210> SEQ ID NO 206
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
gcgcaaaccg uucugcaaug uguaa                                           25

<210> SEQ ID NO 207
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
cgcaaaccgu ucugcaaugu guaau                                           25

<210> SEQ ID NO 208
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
gcaaaccguu cugcaaugug uaauu                                           25

<210> SEQ ID NO 209
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
gcaaugugua auggugcuu gauua                                            25

<210> SEQ ID NO 210
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
ggugcuugau uagccaagau uccau                                           25

<210> SEQ ID NO 211
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
ccauaacuca cuacccagcu cuuaa                                           25
```

```
<210> SEQ ID NO 212
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
gguucaaaca caucuuagcc acuau                                              25

<210> SEQ ID NO 213
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
ggcagguaca uugcauuauu ucuuu                                              25

<210> SEQ ID NO 214
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
ccauauuugu agacuggcgg ucaua                                              25

<210> SEQ ID NO 215
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
cggucauaca auuaugcugu gucua                                              25

<210> SEQ ID NO 216
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
gcugugucua gugccuucug guuau                                              25

<210> SEQ ID NO 217
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
gcuuuuacgc aaguuuuauc agcau                                              25

<210> SEQ ID NO 218
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
gcaaguuuua ucagcaugua aucaa                                              25

<210> SEQ ID NO 219
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
gcauguaauc aaugguugca aagau                                              25

<210> SEQ ID NO 220
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
gcucugcuau aagaggaacc gacuu                                              25

<210> SEQ ID NO 221
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
cgacuuacua gaguugaagc uucua                                              25

<210> SEQ ID NO 222
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
gcuucuaccg uugucugugg uggaa                                              25

<210> SEQ ID NO 223
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
cgguauuuca uucugucgua ggcau                                              25

<210> SEQ ID NO 224
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
gguauuucau ucugucguag gcaua                                             25

<210> SEQ ID NO 225
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
ggggaauacc uucaucugug aagaa                                             25

<210> SEQ ID NO 226
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ccuucaucug ugaagaaguc gcaaa                                             25

<210> SEQ ID NO 227
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
gcccuacgca ggccuauuaa cgcua                                             25

<210> SEQ ID NO 228
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
cgcaggccua uuaacgcuac ggaua                                             25

<210> SEQ ID NO 229
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
cgcuacggau agaucacauu auuau                                             25

<210> SEQ ID NO 230
<211> LENGTH: 25
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 230
ggauagauca cauuauuaug uggau                                  25

<210> SEQ ID NO 231
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
cguuacaguu aaagagacug uuguu                                  25

<210> SEQ ID NO 232
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
ccucugcgcu uuuacaaauc uagau                                  25

<210> SEQ ID NO 233
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ggucuguaaa acuacuacug guaua                                  25

<210> SEQ ID NO 234
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
gcuaggucug cauguguuua uuauu                                  25

<210> SEQ ID NO 235
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
ggugauucua gugaaaucgc cacua                                  25

<210> SEQ ID NO 236
<211> LENGTH: 25
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 236
cgccacuaaa auguuugauu ccuuu                                               25

<210> SEQ ID NO 237
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
cgcuguauaa ugucacacgc gauaa                                               25

<210> SEQ ID NO 238
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
cgugauggcg uaaggcgagg cgaua                                               25

<210> SEQ ID NO 239
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
cguaaggcga ggcgauaacu uccau                                               25

<210> SEQ ID NO 240
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
ggcgauaacu uccauagugu cuuaa                                               25

<210> SEQ ID NO 241
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
ccauaguguc uuaacaacau ucauu                                               25

<210> SEQ ID NO 242
<211> LENGTH: 25
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 242
cggcuucagu uaaccaaauu gucuu                                          25

<210> SEQ ID NO 243
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
ccaaauuguc uugcguaauu cuaau                                          25

<210> SEQ ID NO 244
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
cgacagauuc gcauugcaug ccgua                                          25

<210> SEQ ID NO 245
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
gcauugcaug ccguaagugu aauuu                                          25

<210> SEQ ID NO 246
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
gcaugccgua aguguaauuu agcuu                                          25

<210> SEQ ID NO 247
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
ccucaaagcu acgcgcuaau gauaa                                          25

<210> SEQ ID NO 248
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 248
gcuacgcgcu aaugauaaua ucuua                                              25

<210> SEQ ID NO 249
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
cgcuaaugau aauaucuuau caguu                                              25

<210> SEQ ID NO 250
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
gcuaaugaua auaucuuauc aguua                                              25

<210> SEQ ID NO 251
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ccgcaucuug gacuuuaaag uucuu                                              25

<210> SEQ ID NO 252
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
ccugaugaua agugcuuugc uaaua                                              25

<210> SEQ ID NO 253
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
gcuuugcuaa uaagcaccgg uccuu                                              25

<210> SEQ ID NO 254
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
gcaccggucc uucacacaau gguau                                          25

<210> SEQ ID NO 255
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
ccgguccuuc acacaauggu aucau                                          25

<210> SEQ ID NO 256
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
ggugcucgca uuccagacgu accua                                          25

<210> SEQ ID NO 257
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
gcucgcauuc cagacguacc uacua                                          25

<210> SEQ ID NO 258
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
cgcauuccag acguaccuac uacau                                          25

<210> SEQ ID NO 259
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
gcauuccaga cguaccuacu acauu                                          25

<210> SEQ ID NO 260
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 260
ccagacguac cuacuacauu ggcuu                                           25

<210> SEQ ID NO 261
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
gcauucuucc aucugagugc acuau                                           25

<210> SEQ ID NO 262
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
gggccguaug acaccauacu gccau                                           25

<210> SEQ ID NO 263
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
ccguaugaca ccauacugcc augau                                           25

<210> SEQ ID NO 264
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
ccauacugcc augauccuac uguuu                                           25

<210> SEQ ID NO 265
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
ggccucaugu ucguuacgac uugua                                           25

<210> SEQ ID NO 266
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
```
gccucauguu cguuacgacu uguau                                              25

<210> SEQ ID NO 267
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
cgacuuguau gaugguaaca uguuu                                              25

<210> SEQ ID NO 268
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
ccacaaaugg cucgugggcc auuuu                                              25

<210> SEQ ID NO 269
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
ggccauuuuu aaugaccacc aucuu                                              25

<210> SEQ ID NO 270
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
gccauuuuua augaccacca ucuua                                              25

<210> SEQ ID NO 271
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
ccauuuuuaa ugaccaccau cuuaa                                              25

<210> SEQ ID NO 272
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
ccaucuuaau agaccuggug ucuau            25

<210> SEQ ID NO 273
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
ccuggugucu auuguggcuc ugauu            25

<210> SEQ ID NO 274
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
ggugucuauu guggcucuga uuuua            25

<210> SEQ ID NO 275
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
gcaguaucac uguuccagcc uauua            25

<210> SEQ ID NO 276
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276 ccauuacuu auuccaauu gacua              25

<210> SEQ ID NO 277
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
ccucauuggu cuuggguaua gguuu            25

<210> SEQ ID NO 278
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
ccugacuuug cucuucuauu auauu            25

<210> SEQ ID NO 279
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gcucuucuau uauauuaaua aagua                                              25

<210> SEQ ID NO 280
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
gcuguuguug cugcuguucu uaaua                                              25

<210> SEQ ID NO 281
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
ccugcauuua uuaugcaugu uucuu                                              25

<210> SEQ ID NO 282
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
ccaggacgcu gccucuaaua ucuuu                                              25

<210> SEQ ID NO 283
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
ggacgcugcc ucuaauaucu uuguu                                              25

<210> SEQ ID NO 284
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
cgcugccucu aauaucuuug uuauu                                              25

<210> SEQ ID NO 285
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
gcugccucua auaucuuugu uauua                                              25

<210> SEQ ID NO 286
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ccucuaauau cuuuguuauu aacaa                                              25

<210> SEQ ID NO 287
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
gcagcucuua gaaacucuuu aacua                                              25

<210> SEQ ID NO 288
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
ccuauucacg auuuuugggg uuguu                                              25

<210> SEQ ID NO 289
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
gguuguuuaa caaguauaag uacuu                                              25

<210> SEQ ID NO 290
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
gccgcuuauc gugaagcugc agcau                                              25

-continued

```
<210> SEQ ID NO 291
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
gcgagacugg uagugaucuu cuuua                                              25

<210> SEQ ID NO 292
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
ccucuggcgu guugcaaagc gguuu                                              25

<210> SEQ ID NO 293
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
gcguguugca aagcgguuug gugaa                                              25

<210> SEQ ID NO 294
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
cguguugcaa agcgguuugg ugaaa                                              25

<210> SEQ ID NO 295
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
gguuaccugc gguagcauga cucuu                                              25

<210> SEQ ID NO 296
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
cgguagcaug acucuuaaug gucuu                                              25

<210> SEQ ID NO 297
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
gguagcauga cucuuaaugg ucuuu                                          25

<210> SEQ ID NO 298
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
ccuaauuaug augccuuguu gauuu                                          25

<210> SEQ ID NO 299
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
cgcuccagca aacuugcgug uuguu                                          25

<210> SEQ ID NO 300
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
ggucaugcca ugcaaggcac ucuuu                                          25

<210> SEQ ID NO 301
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
ggcgcagcau uuaguguguu agcau                                          25

<210> SEQ ID NO 302
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
gcauuuagug uguuagcaug cuaua                                          25

<210> SEQ ID NO 303
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ccgacuggua cauucacugu uguaa                                               25

<210> SEQ ID NO 304
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
cgacugguac auucacuguu guaau                                               25

<210> SEQ ID NO 305
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
cgcccuaacu acacaauuaa ggguu                                               25

<210> SEQ ID NO 306
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
ccgguucagc auugauggu acuau                                                25

<210> SEQ ID NO 307
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
gcaccaaguu caguuaacag acaaa                                               25

<210> SEQ ID NO 308
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
gcuuggcuuu acgcagcaau acuua                                               25

<210> SEQ ID NO 309
<211> LENGTH: 25
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 309
gcagcaauac uuaaugguug cgcuu                                         25

<210> SEQ ID NO 310
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
ggcguugcua uugaacagcu gcuuu                                         25

<210> SEQ ID NO 311
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
gcguugcuau ugaacagcug cuuua                                         25

<210> SEQ ID NO 312
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
cguugcuauu gaacagcugc uuuau                                         25

<210> SEQ ID NO 313
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
ggaagaugaa uucacaccug aggau                                         25

<210> SEQ ID NO 314
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
ccugaggaug uuaauaugca gauua                                         25

<210> SEQ ID NO 315
<211> LENGTH: 25
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 315
gguuaugcag aguggguguga gaaaa                                              25

<210> SEQ ID NO 316
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
ggugugagaa aaguuacaua uggua                                               25

<210> SEQ ID NO 317
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
cgacccuugu cucaaccuau gugau                                               25

<210> SEQ ID NO 318
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
cccuugucuc aaccuaugug auaau                                               25

<210> SEQ ID NO 319
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
ccacuaaauu uacuuugugg aacua                                               25

<210> SEQ ID NO 320
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
cccacacagu uguccacu cuuau                                                 25

<210> SEQ ID NO 321
<211> LENGTH: 25
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 321
ccacacaguu guucccacuc uuauu                                          25

<210> SEQ ID NO 322
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
ggccuucguu auguuguugg uuaaa                                          25

<210> SEQ ID NO 323
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
cguuauguug uugguuaaac acaaa                                          25

<210> SEQ ID NO 324
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
gccuguggcu auuuguuuga cuuau                                          25

<210> SEQ ID NO 325
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
gcaaacauag ucuacgagcc cacua                                          25

<210> SEQ ID NO 326
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
cgucagcgcu gauugcaguu gcaaa                                          25

<210> SEQ ID NO 327
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 327
gcugauugca guugcaaauu ggcuu                                              25

<210> SEQ ID NO 328
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
ggcuugcccc cacuaaugcu uauau                                              25

<210> SEQ ID NO 329
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
cccacuaaug cuuauaugcg cacua                                              25

<210> SEQ ID NO 330
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
gguguaaugu gguuguacac uuaua                                              25

<210> SEQ ID NO 331
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
gcauuggaga agccucaagc cccau                                              25

<210> SEQ ID NO 332
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
ccggaaguga agaugauacu uuuau                                              25

<210> SEQ ID NO 333
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
cggaagugaa gaugauacuu uuauu                                    25

<210> SEQ ID NO 334
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
ggaagugaag augauacuuu uauua                                    25

<210> SEQ ID NO 335
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
gcuuagagca ccuaugggug ucuau                                    25

<210> SEQ ID NO 336
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
gcaccuaugg gugucuauga cuuua                                    25

<210> SEQ ID NO 337
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
gcuaacaauc uaacugcacc uagaa                                    25

<210> SEQ ID NO 338
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
gcaccuagaa auucuuggga ggcua                                    25

<210> SEQ ID NO 339
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 339
gggaggcuau ggcucugaac uuuaa                                           25

<210> SEQ ID NO 340
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
gguugcugcu augcagucua aacuu                                           25

<210> SEQ ID NO 341
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
gcagucuaaa cuuacagauc uuaaa                                           25

<210> SEQ ID NO 342
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
ccaacaguua cacuuagagg cuaau                                           25

<210> SEQ ID NO 343
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
gggcuuucug uguuaaaugc cauaa                                           25

<210> SEQ ID NO 344
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
ggcuuucugu guuaaaugcc auaau                                           25

<210> SEQ ID NO 345
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
```
gcagcaacag accccaguga ggcuu                                              25

<210> SEQ ID NO 346
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
gcuagugaua uuuuugacac uccua                                              25

<210> SEQ ID NO 347
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
ccuagcguac uucaagcuac ucuuu                                              25

<210> SEQ ID NO 348
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
gcgcagaaag ccuaucagga agcua                                              25

<210> SEQ ID NO 349
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
cgcagaaagc cuaucaggaa gcuau                                              25

<210> SEQ ID NO 350
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
ggacucuggu gacaccucac cacaa                                              25

<210> SEQ ID NO 351
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
ggugacaccu caccacaagu ucuua                                              25

<210> SEQ ID NO 352
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
ccucaccaca aguucuuaag gcuuu                                              25

<210> SEQ ID NO 353
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
ggcuuugcag aaggcuguua auaua                                              25

<210> SEQ ID NO 354
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
gcagaaggcu guuaauauag cuaaa                                              25

<210> SEQ ID NO 355
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
gcuaaaaacg ccuaugagaa ggaua                                              25

<210> SEQ ID NO 356
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
ggauaaggca guggcccgua aguua                                              25

<210> SEQ ID NO 357
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
gcaguggccc guaaguuaga acgua                                              25

<210> SEQ ID NO 358
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
ggcuaugacu ucuauguaua agcaa                                          25

<210> SEQ ID NO 359
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
gcaaaaauug ucagugcuau gcaaa                                          25

<210> SEQ ID NO 360
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
gcuaugcaaa cuauguuguu uggua                                          25

<210> SEQ ID NO 361
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
gcaaacuaug uuguuggua ugauu                                           25

<210> SEQ ID NO 362
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
gcuucaaaua aacuucgcgu uguaa                                          25

<210> SEQ ID NO 363
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
ccgucuggaa ucagguaguc acaua                                          25

```
<210> SEQ ID NO 364
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
cgucuggaau cagguaguca cauau                                              25

<210> SEQ ID NO 365
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
cccucgcuua acuacgcugg ggcuu                                              25

<210> SEQ ID NO 366
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
ccucgcuuaa cuacgcuggg gcuuu                                              25

<210> SEQ ID NO 367
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
ggggcuuugu gggacauuac aguua                                              25

<210> SEQ ID NO 368
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
gggcuuugug ggacauuaca guuau                                              25

<210> SEQ ID NO 369
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369 ggcuugugg gacauuacag uuaua                                               25
```

```
<210> SEQ ID NO 370
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
gcuugugggg acauuacagu uauaa                                          25

<210> SEQ ID NO 371
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
gggcauccac uucugccguu aaguu                                          25

<210> SEQ ID NO 372
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
ccacuucugc cguuaaguug caaaa                                          25

<210> SEQ ID NO 373
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
ccguuaaguu gcaaaauaau gagau                                          25

<210> SEQ ID NO 374
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
ggucaagagc aaacuaacug uaaua                                          25

<210> SEQ ID NO 375
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
gggucguaaa augcugaugg cucuu                                          25

<210> SEQ ID NO 376
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
cguaaaaugc ugauggcucu ucuuu                                               25

<210> SEQ ID NO 377
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
gcugauggcu cuucuuucug auaau                                               25

<210> SEQ ID NO 378
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
ggcucuucuu ucugauaaug ccuau                                               25

<210> SEQ ID NO 379
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
gcgcguguug aagguaagga cggau                                               25

<210> SEQ ID NO 380
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
cgcguguuga agguaaggac ggauu                                               25

<210> SEQ ID NO 381
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
gcguguugaa gguaaggacg gauuu                                               25

<210> SEQ ID NO 382
<211> LENGTH: 25
```

<212> TYPE: RNA
<213> ORGANIZM: Artificial Sequence
<220> FEATURE:
<223> OTHER INFORMATION: Description of Artificial Sequence: Synthetic
oligonucleotide

<400> SEQUENCE: 382
gcaaauucuu gauugcggga ccaaa                                   25

<210> SEQ ID NO 383
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 383
ggaccaaaag gaccugaaau ccgau                                   25

<210> SEQ ID NO 384
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 384
gggcacauug cugcgacugu uagau                                   25

<210> SEQ ID NO 385
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 385
ggcacauugc ugcgacuguu agauu                                   25

<210> SEQ ID NO 386
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 386
gcgacuguua gauugcaagc ugguu                                   25

<210> SEQ ID NO 387
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 387
gcaagcuggu ucuaacaccg aguuu                                   25

<210> SEQ ID NO 388
<211> LENGTH: 25
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 388
gguucuaaca ccgaguuugc cucua                                              25

<210> SEQ ID NO 389
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
ccuaaaacug guacagguau agcua                                              25

<210> SEQ ID NO 390
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
gguacaggua uagcuauauc uguua                                              25

<210> SEQ ID NO 391
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
gcuauaucug uuaaaccaga gagua                                              25

<210> SEQ ID NO 392
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
ccgugcgcau auagaacauc cugau                                              25

<210> SEQ ID NO 393
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
ccuguaaugu cugucaauau uggau                                              25

<210> SEQ ID NO 394
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 394
gccccaaucu aaagauucca auuuu                                              25

<210> SEQ ID NO 395
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
ccccaaucua aagauuccaa uuuuu                                              25

<210> SEQ ID NO 396
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
cccaaucuaa agauuccaau uuuuu                                              25

<210> SEQ ID NO 397
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
ccaaucuaaa gauuccaauu uuuua                                              25

<210> SEQ ID NO 398
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
cgggguucua uuguaaaugc ccgaa                                              25

<210> SEQ ID NO 399
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399 ggggguucuau uguaaaugcc cgaau                                             25

<210> SEQ ID NO 400
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 400 gguucuauu guaaaugccc gaaua                                              25

<210> SEQ ID NO 401
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
cgaauagaac ccguucaag ugguu                                              25

<210> SEQ ID NO 402
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
gggcauuuga caucugcaac uauaa                                             25

<210> SEQ ID NO 403
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
ggcuaagguu gcugguauug gaaaa                                             25

<210> SEQ ID NO 404
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
gcuaagguug cugguauugg aaaau                                             25

<210> SEQ ID NO 405
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
gguauuggaa aauacuacaa gacua                                             25

<210> SEQ ID NO 406
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 406
ggaaaauacu acaagacuaa uacuu				25

<210> SEQ ID NO 407
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
ccaagggcau cauuuagacu ccuau				25

<210> SEQ ID NO 408
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
cguuaagagg cauacuaugg agaau				25

<210> SEQ ID NO 409
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
gcauacuaug gagaauuaug aacua				25

<210> SEQ ID NO 410
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
ccaugauuuc uucaucuuug augua				25

<210> SEQ ID NO 411
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
ccucauauug uacgucagcg uuuaa				25

<210> SEQ ID NO 412
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 412
cgucagcguu uaacugagua cacua                                           25

<210> SEQ ID NO 413
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
gcccugaggc acuugauca aaaua                                            25

<210> SEQ ID NO 414
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
gcuuaaggcu aucuuaguga aguau                                           25

<210> SEQ ID NO 415
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
gcugugaugu uaccuacuuu gaaaa                                           25

<210> SEQ ID NO 416
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
ccuacuuuga aaauaaacuc ugguu                                           25

<210> SEQ ID NO 417
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
ccaguguuau ugguguuuau cauaa                                           25

<210> SEQ ID NO 418
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 418
cgccaagcua ucuuaaacac uguua                                         25

<210> SEQ ID NO 419
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
gccaagcuau cuuaaacacu guuaa                                         25

<210> SEQ ID NO 420
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
ccaagcuauc uuaaacacug uuaaa                                         25

<210> SEQ ID NO 421
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
gcuaucuuaa acacuguuaa auuuu                                         25

<210> SEQ ID NO 422
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
gcucacacua gacaaccagg accuu                                         25

<210> SEQ ID NO 423
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
ccaggaccuu aauggcaagu gguau                                         25

<210> SEQ ID NO 424
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
```
ggaccuuaau ggcaaguggu augau                                         25

<210> SEQ ID NO 425
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
ccuuaauggc aagugguaug auuuu                                         25

<210> SEQ ID NO 426
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
gcaaguggua ugauuuggu gacuu                                          25

<210> SEQ ID NO 427
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
gguaugauuu uggugacuuc guaau                                         25

<210> SEQ ID NO 428
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
gguucaggag uagcuauagu ugaua                                         25

<210> SEQ ID NO 429
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
gcuauaguug auagcuacua uucuu                                         25

<210> SEQ ID NO 430
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
cgauugucug gccgcugaga cacau					25

<210> SEQ ID NO 431
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
cgcugagaca cauagggauu gugau					25

<210> SEQ ID NO 432
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
gcugagacac auagggauug ugauu					25

<210> SEQ ID NO 433
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
gguacaacuc uuugagaagu acuuu					25

<210> SEQ ID NO 434
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
cgcaaauugc guuaauugua cugau					25

<210> SEQ ID NO 435
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
ccguugugug uuacauugug cuaau					25

<210> SEQ ID NO 436
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
cguugugugu uacauugugc uaauu					25

<210> SEQ ID NO 437
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
gcuaauuuca auguauuguu ugcua                                              25

<210> SEQ ID NO 438
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
gccuaagacu uguuucggac ccaua                                              25

<210> SEQ ID NO 439
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
cggacccaua guccgaaaga ucuuu                                              25

<210> SEQ ID NO 440
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
gccauuugua guaucuugug guuau                                              25

<210> SEQ ID NO 441
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
gguuaucacu acaaagaauu agguu                                              25

<210> SEQ ID NO 442
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
gguuuaguca ugaauaugga uguua                                              25

<210> SEQ ID NO 443
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
ccagccaugc acauugccuc cucua                                           25

<210> SEQ ID NO 444
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
gcacauugcc uccucuaacg cuuuu                                           25

<210> SEQ ID NO 445
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
gccuccucua acgcuuuucu ugauu                                           25

<210> SEQ ID NO 446
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
ccuccucuaa cgcuuuucuu gauuu                                           25

<210> SEQ ID NO 447
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
gcuuuucuug auuugaggac aucau                                           25

<210> SEQ ID NO 448
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
gcugcacuua caacgguuu gacuu                                            25

```
<210> SEQ ID NO 449
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
ggccuggcaa uuuuaaccaa gacuu                                              25

<210> SEQ ID NO 450
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
ccaagacuuc uaugauuucg uggua                                              25

<210> SEQ ID NO 451
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
gcucaaacau uuuuucuuug cucaa                                              25

<210> SEQ ID NO 452
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
gcucaagaug guaaugcugc uauua                                              25

<210> SEQ ID NO 453
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
gguaaugcug cuauuacaga uuaua                                              25

<210> SEQ ID NO 454
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
gcuauuacag auuauaauua cuauu                                              25

<210> SEQ ID NO 455
```

<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 455
gccuacuaug ugugacauca aacaa                                        25

<210> SEQ ID NO 456
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 456
ccuacuaugu gugacaucaa acaaa                                        25

<210> SEQ ID NO 457
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 457
gcauggaagu uguaaacaag uacuu                                        25

<210> SEQ ID NO 458
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 458
ggaaguugua aacaaguacu ucgaa                                        25

<210> SEQ ID NO 459
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 459
cgaaaucuau gacggugguu gucuu                                        25

<210> SEQ ID NO 460
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 460
cgguggungu cuuaaugcuu cugaa                                        25

<210> SEQ ID NO 461
<211> LENGTH: 25

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
gcuucugaag ugguuguuaa uaauu                                              25

<210> SEQ ID NO 462
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
gccauccuuu uaauaaguuu ggcaa                                              25

<210> SEQ ID NO 463
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
ccauccuuuu aauaaguuug gcaaa                                              25

<210> SEQ ID NO 464
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
cgugucuauu augagagcau gucuu                                              25

<210> SEQ ID NO 465
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
gcaggcgugu ccauacuuag cacaa                                              25

<210> SEQ ID NO 466
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
cgccaguacc aucagaaaau gcuua                                              25

<210> SEQ ID NO 467
<211> LENGTH: 25
<212> TYPE: RNA
```

<213> ORGANISM: Artificial Sequence
<220> FEATURE:
<223> OTHER INFORMATION: Description of Artificial Sequence: Synthetic
    oligonucleotide

<400> SEQUENCE: 467
gccaguacca ucagaaaaug cuuaa                                          25

<210> SEQ ID NO 468
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 468
cguggagcga cuugcgucau uggua                                          25

<210> SEQ ID NO 469
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 469
ggagcgacuu gcgucauugg uacua                                          25

<210> SEQ ID NO 470
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 470
gcgacuugcg ucauugguac uacaa                                          25

<210> SEQ ID NO 471
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 471
cgacuugcgu cauugguacu acaaa                                          25

<210> SEQ ID NO 472
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 472
gcgucauugg uacuacaaag uucua                                          25

<210> SEQ ID NO 473
<211> LENGTH: 25
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 473
gguggcuggg auuucaugcu uaaaa                                               25

<210> SEQ ID NO 474
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
ggcugggauu ucaugcuuaa aacau                                               25

<210> SEQ ID NO 475
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
gcugggauuu caugcuuaaa acauu                                               25

<210> SEQ ID NO 476
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
ggguugggau uacccuaagu gugau                                               25

<210> SEQ ID NO 477
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
gguugggauu acccuaagug ugaua                                               25

<210> SEQ ID NO 478
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
ccuaagugug auagagcuau gccua                                               25

<210> SEQ ID NO 479
<211> LENGTH: 25
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 479
ccuaauaugu guagaaucuu cgcuu                                              25

<210> SEQ ID NO 480
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
cgcuucacuc auauuagcuc guaaa                                              25

<210> SEQ ID NO 481
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
gggacagauu uuaucgcuug gcaaa                                              25

<210> SEQ ID NO 482
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
ggacagauuu uaucgcuugg caaau                                              25

<210> SEQ ID NO 483
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
ggcaaaugag ugugcucagg ugcua                                              25

<210> SEQ ID NO 484
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
gcaaaugagu gugcucaggu gcuaa                                              25

<210> SEQ ID NO 485
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 485
gguuacuacg ucaaaccugg aggua                                          25

<210> SEQ ID NO 486
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
ccacugcaua ugccaauagu gucuu                                          25

<210> SEQ ID NO 487
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
ggagcacuag cccagacccc aaauu                                          25

<210> SEQ ID NO 488
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
gcccagaccc caaauuuguu gauaa                                          25

<210> SEQ ID NO 489
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
cccagacccc aaauuuguug auaaa                                          25

<210> SEQ ID NO 490
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
ccagacccca aauuuguuga uaaau                                          25

<210> SEQ ID NO 491
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 491 gcuuucuua auaagcacuu uucua                                       25

<210> SEQ ID NO 492
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
cggugucguu ugcuauaaua gugau                                      25

<210> SEQ ID NO 493
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
ggugucguuu gcuauaauag ugauu                                      25

<210> SEQ ID NO 494
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
gcuauaauag ugauuaugca gcuaa                                      25

<210> SEQ ID NO 495
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
gcagcuaagg guuacauugc uggaa                                      25

<210> SEQ ID NO 496
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
ggguuacauu gcuggaauac agaau                                      25

<210> SEQ ID NO 497
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 497
gguuacauug cuggaauaca gaauu                                         25

<210> SEQ ID NO 498
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
ggaaacgcug uauuaucaga acaau                                         25

<210> SEQ ID NO 499
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
cgcuguauua ucagaacaau gucuu                                         25

<210> SEQ ID NO 500
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
gcuguauuau cagaacaaug ucuuu                                         25

<210> SEQ ID NO 501
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
gcugggugga aaccgaucug aagaa                                         25

<210> SEQ ID NO 502
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
cgaucugaag aaagggccac augaa                                         25

<210> SEQ ID NO 503
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
gccacaugaa uucguucac agcau                                              25

<210> SEQ ID NO 504
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
ccacaugaau ucguucaca gcaua                                              25

<210> SEQ ID NO 505
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
gcuuuauauu aaggauggcg acgau                                             25

<210> SEQ ID NO 506
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
ggauggcgac gaugguuacu uccuu                                             25

<210> SEQ ID NO 507
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
ggcgacgaug guuacuuccu uccuu                                             25

<210> SEQ ID NO 508
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
gcgacgaugg uuacuuccuu ccuua                                             25

<210> SEQ ID NO 509
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
cgacgauggu uacuuccuuc cuuau                                          25

<210> SEQ ID NO 510
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
ccuuauccag acccuucaag aauuu                                          25

<210> SEQ ID NO 511
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
ccuucaagaa uuuugucugc cgguu                                          25

<210> SEQ ID NO 512
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
gguugcuuug uagaugauau cguua                                          25

<210> SEQ ID NO 513
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
gcgguuugug ucuuuggcua uagau                                          25

<210> SEQ ID NO 514
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
gcuauagaug cuuacccucu cacaa                                          25

<210> SEQ ID NO 515
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
cccucucaca aagcaugaag auaua                                          25

<210> SEQ ID NO 516
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
gcaugaagau auagaauacc agaau                                  25

<210> SEQ ID NO 517
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
ccagaaugua uucuggucu acuua                                   25

<210> SEQ ID NO 518
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
gggucuacuu acaguauaua gaaaa                                  25

<210> SEQ ID NO 519
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
ggucuacuua caguauauag aaaaa                                  25

<210> SEQ ID NO 520
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
gcuugacagu uauucuguca ugcua                                  25

<210> SEQ ID NO 521
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
ccuaccacuu ugcaggcugu cgguu                                  25

<210> SEQ ID NO 522
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
gcaggcuguc gguucaugcg uugua                                         25

<210> SEQ ID NO 523
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
ccacauaaga ugguuuuguc uguuu                                         25

<210> SEQ ID NO 524
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
ccacuuugcg cuaauggucu uguau                                         25

<210> SEQ ID NO 525
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
gcgcuaaugg ucuuguauuc ggcuu                                         25

<210> SEQ ID NO 526
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
cgcuaauggu cuuguauucg gcuua                                         25

<210> SEQ ID NO 527
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
gcuaaugguc uuguauucgg cuuau                                         25

```
<210> SEQ ID NO 528
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
ggugauuaca cccuugccaa uacua                                          25

<210> SEQ ID NO 529
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
ccaauacuac aacagaacca cucaa                                          25

<210> SEQ ID NO 530
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
ccaccacuca aucguaauua uguuu                                          25

<210> SEQ ID NO 531
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
ccacucaauc guaauuaugu uuuua                                          25

<210> SEQ ID NO 532
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
gguuaucaua uaaccaaaaa uagua                                          25

<210> SEQ ID NO 533
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
gcgcauugau uauagugaug cugua                                          25

<210> SEQ ID NO 534
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
cgcauugauu auagugaugc uguau                                              25

<210> SEQ ID NO 535
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
gcuguauccu acaagucuag uacaa                                              25

<210> SEQ ID NO 536
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
ccuacaaguc uaguacaacg uauaa                                              25

<210> SEQ ID NO 537
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
cguauaaacu gacuguaggu gacau                                              25

<210> SEQ ID NO 538
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
ggcuaccuug acggcgccca caauu                                              25

<210> SEQ ID NO 539
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
gguauguuaa aauuacuggg uugua                                              25

<210> SEQ ID NO 540
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
gccaacuucc aaaaaucagg uuaua                                        25

<210> SEQ ID NO 541
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 541
ccaaaaauca gguuauagua aauau                                        25

<210> SEQ ID NO 542
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
gcacguguug uuuauacagc auguu                                        25

<210> SEQ ID NO 543
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
cgcagcuguu gaugcuuugu gugaa                                        25

<210> SEQ ID NO 544
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
gcagcuguug augcuuugug ugaaa                                        25

<210> SEQ ID NO 545
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545 gcuugugug aaaaagcuuu uaaau                                         25

<210> SEQ ID NO 546
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 546
gcuuuuaaau auugaacau ugcua                                          25

<210> SEQ ID NO 547
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
cguguugagu gcuaugacag guuua                                          25

<210> SEQ ID NO 548
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
gguuaguaug ugcacuaauu augau                                          25

<210> SEQ ID NO 549
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
gcacuaauua ugaucuuuca auuau                                          25

<210> SEQ ID NO 550
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
gcacaguugc cagcuccuag gacuu                                          25

<210> SEQ ID NO 551
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
ccagcuccua ggacuuuguu gacua                                          25

<210> SEQ ID NO 552
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 552
ggacuuuguu gacuagaggc acauu                                            25

<210> SEQ ID NO 553
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
gcacugugag cgcucuuguc uacaa                                            25

<210> SEQ ID NO 554
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
gcgcucuugu cuacaauaau aaauu                                            25

<210> SEQ ID NO 555
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
gcuuuaaaau acucuauaag ggcaa                                            25

<210> SEQ ID NO 556
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
cgcaugaugc uagcucugcc auuaa                                            25

<210> SEQ ID NO 557
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
gcaugaugcu agcucugcca uuaau                                            25

<210> SEQ ID NO 558
<211> LENGTH: 25
<212> TYPE: RNA
<213> ORGANISM: Artificial Sequence
<220> FEATURE:
```

<223> OTHER INFORMATION: Description of Artificial Sequence: Synthetic
     oligonucleotide

<400> SEQUENCE: 558
gccauuaaua gaccacaacu cacau                                          25

<210> SEQ ID NO 559
<211> LENGTH: 25
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 559
ccauuaauag accacaacuc acauu                                          25

<210> SEQ ID NO 560
<211> LENGTH: 25
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 560
ccacaacuca cauuugugaa gaauu                                          25

<210> SEQ ID NO 561
<211> LENGTH: 25
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 561
ccggcaugga guaaggcagu cuuua                                          25

<210> SEQ ID NO 562
<211> LENGTH: 25
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 562
cggcauggag uaaggcaguc uuuau                                          25

<210> SEQ ID NO 563
<211> LENGTH: 25
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 563
ggcauggagu aaggcagucu uuauu                                          25

<210> SEQ ID NO 564
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 564
gcauggagua aggcagucuu uauuu                                              25

<210> SEQ ID NO 565
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
ccucacaggg uucagaauac cagua                                              25

<210> SEQ ID NO 566
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
gcacaugcua acaacauuaa cagau                                              25

<210> SEQ ID NO 567
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
gcaaucacuc gugcccaaaa aggua                                              25

<210> SEQ ID NO 568
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
gcccaaaaag guauucuuug uguua                                              25

<210> SEQ ID NO 569
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 569
cccaaaaagg uauucuuugu guuau                                              25

<210> SEQ ID NO 570
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 570
ggcacucuuu gaguccuuag aguuu                                          25

<210> SEQ ID NO 571
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
gcacucuuug aguccuuaga guuua                                          25

<210> SEQ ID NO 572
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
ccuuagaguu uacugaauug ucuuu                                          25

<210> SEQ ID NO 573
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
ccuuuuuaaa gauugcucua gagaa                                          25

<210> SEQ ID NO 574
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
ggccucucac cugcuuaugc accaa                                          25

<210> SEQ ID NO 575
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
gcgugaaucu uaauuuaccc gcaaa                                          25

<210> SEQ ID NO 576
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 576
cgugaaucuu aauuuacccg caaau                                          25

<210> SEQ ID NO 577
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
cgcaaauguc ccauacucuc guguu                                          25

<210> SEQ ID NO 578
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
gcaaaugucc cauacucucg uguua                                          25

<210> SEQ ID NO 579
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
cguguuauuu ccaggauggg cuuua                                          25

<210> SEQ ID NO 580
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
gggcuuuaaa cucgaugcaa caguu                                          25

<210> SEQ ID NO 581
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
ggcaaguucg aagcuggaua ggcuu                                          25

<210> SEQ ID NO 582
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
```

```
ggugcucaug cuucccguaa ugcau                                          25
```

<210> SEQ ID NO 583
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583

```
ccaaugugcc ucuacaauua ggauu                                          25
```

<210> SEQ ID NO 584
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584

```
gguguuguag acacugagug gggua                                          25
```

<210> SEQ ID NO 585
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585

```
cguccuccac caggugaaca guuua                                          25
```

<210> SEQ ID NO 586
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586

```
cguuuguuug uugggcucau ggcuu                                          25
```

<210> SEQ ID NO 587
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 587

```
ggcuuugaau uaacgucugc aucau                                          25
```

<210> SEQ ID NO 588
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588 gcuugaauu aacgucugca ucaua 25

<210> SEQ ID NO 589
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
cgucugcauc auacuuugc aagau 25

<210> SEQ ID NO 590
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
gcaucauacu uuugcaagau aggua 25

<210> SEQ ID NO 591
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
gcagcguacu cuucaccucu gcaau 25

<210> SEQ ID NO 592
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
gcguacucuu caccucugca aucuu 25

<210> SEQ ID NO 593
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 593
cguacucuuc accucugcaa ucuua 25

<210> SEQ ID NO 594
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
gcaaucuuau gccugcugga cucau 25

<210> SEQ ID NO 595
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
gccugcugga cucauuccug cgguu                                         25

<210> SEQ ID NO 596
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
ccugcuggac ucauuccugc gguua                                         25

<210> SEQ ID NO 597
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597
ggacucauuc cugcgguuau gauua                                         25

<210> SEQ ID NO 598
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
ccugcgguua ugauuauguc uacaa                                         25

<210> SEQ ID NO 599
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 599
gguuaugauu augucuacaa cccuu                                         25

<210> SEQ ID NO 600
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
cgauguucaa caguggqguu augua                                         25

```
<210> SEQ ID NO 601
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
cgaucguuau ugcucugucc aucaa                                         25

<210> SEQ ID NO 602
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
gcucaugugg cuucuaauga ugcaa                                         25

<210> SEQ ID NO 603
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
gcaauaauga cucguuguuu agcua                                         25

<210> SEQ ID NO 604
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
cguuguuuag cuauucauuc uuguu                                         25

<210> SEQ ID NO 605
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
ccuuauaucu cacaugaaaa gaaau                                         25

<210> SEQ ID NO 606
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
gcgcaacguc guacgugcug cucuu                                         25
```

<210> SEQ ID NO 607
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 607
cgguucauuu gacaaagucu augau                                              25

<210> SEQ ID NO 608
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 608
gguucauuug acaaagucua ugaua                                              25

<210> SEQ ID NO 609
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 609
ggcauuauuu ugaugcacag cccuu                                              25

<210> SEQ ID NO 610
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 610
ggacauggcc ucaagauuug cugau                                              25

<210> SEQ ID NO 611
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 611
gcacgcuuuu cauacaccag cauau                                              25

<210> SEQ ID NO 612
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 612
cgcuuuucau acaccagcau augau                                              25

<210> SEQ ID NO 613

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
ccuuuaccau ucuuuuauua uucua                                        25

<210> SEQ ID NO 614
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
gguaauggua guaugauaga ggaua                                        25

<210> SEQ ID NO 615
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
gguaguauga uagaggauau ugauu                                        25

<210> SEQ ID NO 616
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
ggauauugau uauguacccc uaaaa                                        25

<210> SEQ ID NO 617
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 617
ccccuaaaau cugcagucug uauua                                        25

<210> SEQ ID NO 618
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
gguguuauaa gaccuuugau auuua                                        25

<210> SEQ ID NO 619
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
ccauuuuauu gguguugagg gugaa                                              25

<210> SEQ ID NO 620
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
ccacuuugcc uacuaauaua gcuuu                                              25

<210> SEQ ID NO 621
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621
gcgugcugua cgcucgcauc ccgau                                              25

<210> SEQ ID NO 622
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
cgugcuguac gcucgcaucc cgauu                                              25

<210> SEQ ID NO 623
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 623
cccgauuuca aauugcuaca caauu                                              25

<210> SEQ ID NO 624
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624
ccgauuucaa auugcuacac aauuu                                              25

<210> SEQ ID NO 625
<211> LENGTH: 25
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 625
cgauuucaaa uugcuacaca auuua        25

<210> SEQ ID NO 626
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 626
gcuacacaau uuacaagcag acauu        25

<210> SEQ ID NO 627
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 627
gcuacaaguu cguccuuugg gauua        25

<210> SEQ ID NO 628
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 628
ccuuugggau uaugaacgua gcaau        25

<210> SEQ ID NO 629
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 629
gggauuauga acguagcaau auuua        25

<210> SEQ ID NO 630
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 630
ggauuaugaa cguagcaaua uuuau        25

<210> SEQ ID NO 631
<211> LENGTH: 25
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 631
cguagcaaua uuuaugguac ugcua                                              25

<210> SEQ ID NO 632
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632
gcaauauuua ugguacugcu acuau                                              25

<210> SEQ ID NO 633
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
cccaaugcca ucuuuauuuc ugaua                                              25

<210> SEQ ID NO 634
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
gccaucuuua uuucugauag aaaaa                                              25

<210> SEQ ID NO 635
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 635
ccaucuuuau uucugauaga aaaau                                              25

<210> SEQ ID NO 636
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
cccuuguaug guagguccug auuau                                              25

<210> SEQ ID NO 637
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 637
ccgugauagu gauguuguua aacaa                                              25

<210> SEQ ID NO 638
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
ggaaaacuau gcuuugagc acgua                                               25

<210> SEQ ID NO 639
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
cguuaggcgg ucuucacuug cuuau                                              25

<210> SEQ ID NO 640
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 640
ggcggucuuc acuugcuuau ugguu                                              25

<210> SEQ ID NO 641
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 641
gcggucuuca cuugcuuauu gguuu                                              25

<210> SEQ ID NO 642
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 642
cggucuucac uugcuuauug guuua                                              25

<210> SEQ ID NO 643
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 643
ggucuucacu ugcuuauugg uuuau                                          25

<210> SEQ ID NO 644
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
gcuuauuggu uuauacaaga agcaa                                          25

<210> SEQ ID NO 645
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
ggaaggucau auuauuaugg aagaa                                          25

<210> SEQ ID NO 646
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 646
gcuaaaaggu agcucaacua uucau                                          25

<210> SEQ ID NO 647
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 647
gguagcucaa cuauucauaa cuauu                                          25

<210> SEQ ID NO 648
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648
gcucaacuau ucauaacuau uuuau                                          25

<210> SEQ ID NO 649
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 649
ggcuuuuaag gcgguguguu cuguu                                          25

<210> SEQ ID NO 650
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
gcuuuuaagg cggguguguuc uguua                                         25

<210> SEQ ID NO 651
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 651
ggcggugugu ucuguuauag auuua                                          25

<210> SEQ ID NO 652
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
gcgguguguu cuguuauaga uuuaa                                          25

<210> SEQ ID NO 653
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
cggguguguc uguuauagau uuaaa                                          25

<210> SEQ ID NO 654
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 654
gcuugacgac uuuguuauga uuuua                                          25

<210> SEQ ID NO 655
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 655
cguaguaucc aagguuguca agguu                                           25

<210> SEQ ID NO 656
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
gguugucaag guuccuauug acuua                                           25

<210> SEQ ID NO 657
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657
gguuccuauu gacuuaacaa ugauu                                           25

<210> SEQ ID NO 658
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 658
cccucgacuc caggcuucug cagau                                           25

<210> SEQ ID NO 659
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 659
ccucgacucc aggcuucugc agauu                                           25

<210> SEQ ID NO 660
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 660
gccaucccuc uuuaaaguuc aaaau                                           25

<210> SEQ ID NO 661
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 661
```
cccucuuuaa aguucaaaau guaaa                                    25

<210> SEQ ID NO 662
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
cgcggugugc acaugaacau cgcua                                    25

<210> SEQ ID NO 663
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
gcggugugca caugaacauc gcuaa                                    25

<210> SEQ ID NO 664
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
cggugugcac augaacaucg cuaaa                                    25

<210> SEQ ID NO 665
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 665
ggugugcaca ugaacaucgc uaaau                                    25

<210> SEQ ID NO 666
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 666
gccaguauuu aaauacuugc acauu                                    25

<210> SEQ ID NO 667
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 667
ccaguauuua aauacuugca cauua       25

<210> SEQ ID NO 668
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 668
gccugccaau augcguguua uacau       25

<210> SEQ ID NO 669
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
ccugccaaua ugcguguuau acauu       25

<210> SEQ ID NO 670
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 670
cguguuauac auuuuggcgc ugguu       25

<210> SEQ ID NO 671
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 671
gccauuauua uagauaauga uuuaa       25

<210> SEQ ID NO 672
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 672
ccauuauuau agauaaugau uuaaa       25

<210> SEQ ID NO 673
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 673
cgugucagau gcugacauaa cuuua       25

<210> SEQ ID NO 674
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 674
gcugacauaa cuuuauuugg agauu                                             25

<210> SEQ ID NO 675
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
ccgacaugua ugauccuacu acuaa                                             25

<210> SEQ ID NO 676
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 676
ccuacuacua agaauguaac aggua                                             25

<210> SEQ ID NO 677
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 677
gguaguaaug agucaaaggc uuuau                                             25

<210> SEQ ID NO 678
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 678
gcuuuauucu uuacuuaccu gugua                                             25

<210> SEQ ID NO 679
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 679
ccuguguaac cucauuaaua auaau                                             25

```
<210> SEQ ID NO 680
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 680
ggugggucug uugcuauuaa aauaa                                              25

<210> SEQ ID NO 681
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 681
gcuauuaaaa uaacagaaca cucuu                                              25

<210> SEQ ID NO 682
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 682
ggagcguuga acuuuaugaa cuuau                                              25

<210> SEQ ID NO 683
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 683
gggaaaauuu gcuuggugga cuguu                                              25

<210> SEQ ID NO 684
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 684
ggaaaauuug cuugguggac uguuu                                              25

<210> SEQ ID NO 685
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 685
gcaaaugcau ccucaucuga aggau                                              25
```

```
<210> SEQ ID NO 686
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 686
gguauuaauu acuuggguac uauua                                         25

<210> SEQ ID NO 687
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 687
ggguacuauu aaagaaaaua uagau                                         25

<210> SEQ ID NO 688
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 688
gguggugcua ugcacgccaa cuaua                                         25

<210> SEQ ID NO 689
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 689
ggugcuaugc acgccaacua uauau                                         25

<210> SEQ ID NO 690
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 690
gcuaugcacg ccaacuauau auuuu                                         25

<210> SEQ ID NO 691
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
cgccaacuau auauuuugga gaaau                                         25

<210> SEQ ID NO 692
```

<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 692
gccaacuaua uauuuggag aaauu    25

<210> SEQ ID NO 693
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 693
ccacuccuau gaaucugagu acuua    25

<210> SEQ ID NO 694
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 694
ggagagucaa auuaacgaac ucgua    25

<210> SEQ ID NO 695
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 695
ggguaaguua cuuauccgug acaau    25

<210> SEQ ID NO 696
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 696
ccgugacaau gauacacuca guguu    25

<210> SEQ ID NO 697
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 697
cgugacaaug auacacucag uguuu    25

<210> SEQ ID NO 698
<211> LENGTH: 25

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
ggcugacggu auuauauacc cucaa                                       25

<210> SEQ ID NO 699
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
gguauuauau acccucaagg ccgua                                       25

<210> SEQ ID NO 700
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
gccguacaua uucuaacaua acuau                                       25

<210> SEQ ID NO 701
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
cccuaucagg gagaccaugg ugaua                                       25

<210> SEQ ID NO 702
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
ccuaucaggg agaccauggu gauau                                       25

<210> SEQ ID NO 703
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703
gggagaccau ggugauaugu auguu                                       25

<210> SEQ ID NO 704
<211> LENGTH: 25
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 704
ggagaccaug gugauaugua uguuu                                            25

<210> SEQ ID NO 705
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
ccaucuacca gcgcuacuau acgaa                                            25

<210> SEQ ID NO 706
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
ccagcgcuac uauacgaaaa auuua                                            25

<210> SEQ ID NO 707
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 707
gggccgcuuc uucaaucaua cucua                                            25

<210> SEQ ID NO 708
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 708
gcccgaugga uguggcacuu uacuu                                            25

<210> SEQ ID NO 709
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 709
cccgauggau guggcacuuu acuua                                            25

<210> SEQ ID NO 710
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 710
ggauguggca cuuuacuuag agcuu                                             25

<210> SEQ ID NO 711
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
ggcacuuuac uuagagcuuu uuauu                                             25

<210> SEQ ID NO 712
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
ccugcuggca auccuauac uucuu                                              25

<210> SEQ ID NO 713
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 713
gcaacagauu guucugaugg caauu                                             25

<210> SEQ ID NO 714
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 714
cguaaugcca gucugaacuc uuuua                                             25

<210> SEQ ID NO 715
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 715
ccagucugaa cucuuuaag gagua                                              25

<210> SEQ ID NO 716
<211> LENGTH: 25
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 716
cguaacugca ccuuuaugua cacuu                                              25

<210> SEQ ID NO 717
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 717
gcaccuuuau guacacuuau aacau                                              25

<210> SEQ ID NO 718
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 718
cgaagaugag auuuuagagu gguuu                                              25

<210> SEQ ID NO 719
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 719
gcucaaggug uucaccucuu cucau                                              25

<210> SEQ ID NO 720
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 720
ccucuucuca ucucgguaug uugau                                              25

<210> SEQ ID NO 721
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 721
gguauguuga uuuguacggc ggcaa                                              25

<210> SEQ ID NO 722
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 722
ccguuaacuu uccuguugga uuuuu                                               25

<210> SEQ ID NO 723
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 723
ggauuuuucu guugaugguu auaua                                               25

<210> SEQ ID NO 724
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 724
cgcagagcua uagacugugg uuuua                                               25

<210> SEQ ID NO 725
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 725
gcagagcuau agacuguggu uuuaa                                               25

<210> SEQ ID NO 726
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 726
gcuauagacu gugguuuuaa ugauu                                               25

<210> SEQ ID NO 727
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 727
ccacugcuca uaugaauccu ucgau                                               25

<210> SEQ ID NO 728
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 728
ccuucgaugu ugaaucugga guuua                                           25

<210> SEQ ID NO 729
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 729
cgaagcaaaa ccuucuggcu caguu                                           25

<210> SEQ ID NO 730
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 730
ggcugaaggu guugaaugug auuuu                                           25

<210> SEQ ID NO 731
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 731
gcugaaggug uugaauguga uuuuu                                           25

<210> SEQ ID NO 732
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 732
ggcacaccuc cucagguuua uaauu                                           25

<210> SEQ ID NO 733
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 733
gcacaccucc ucagguuuau aauuu                                           25

<210> SEQ ID NO 734
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 734
ccucagguuu auaauuucaa gcguu    25

<210> SEQ ID NO 735
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 735
gguuuauaau uucaagcguu ugguu    25

<210> SEQ ID NO 736
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 736
gcguuugguu uuuaccaauu gcaau    25

<210> SEQ ID NO 737
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 737
cguuugguuu uuaccaauug caauu    25

<210> SEQ ID NO 738
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 738
gguuuuuacc aauugcaauu auaau    25

<210> SEQ ID NO 739
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 739
gcuuucacuu uuuucuguga augau    25

<210> SEQ ID NO 740
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 740
gcugguccaa uaucccaguu uaauu                                         25

<210> SEQ ID NO 741
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 741
gguccaauau cccaguuuaa uuaua                                         25

<210> SEQ ID NO 742
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 742
ccaguuuaau uauaaacagu ccuuu                                         25

<210> SEQ ID NO 743
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 743
ccuuuucuaa ucccacaugu uugau                                         25

<210> SEQ ID NO 744
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 744
ccuuacuacu auuacuaagc cucuu                                         25

<210> SEQ ID NO 745
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 745
ccucaguuag ugaacgcuaa ucaau                                         25

<210> SEQ ID NO 746
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 746
cgcuaaucaa uacucacccu gugua                           25

<210> SEQ ID NO 747
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 747
gcuaaucaau acucacccug uguau                           25

<210> SEQ ID NO 748
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 748
gggaagacgg ugauuauuau aggaa                           25

<210> SEQ ID NO 749
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 749
ggaagacggu gauuauuaua ggaaa                           25

<210> SEQ ID NO 750
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 750
cggugauuau uauaggaaac aacua                           25

<210> SEQ ID NO 751
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 751
ggugauuauu auaggaaaca acuau                           25

<210> SEQ ID NO 752
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 752
ggcuggcuug uugcuagugg cucaa                           25

<210> SEQ ID NO 753
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 753
gcuuguugcu aguggcucaa cuguu                                          25

<210> SEQ ID NO 754
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 754
gcaauuacag augggcuuug guauu                                          25

<210> SEQ ID NO 755
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 755
gggcuuuggu auuacaguuc aauau                                          25

<210> SEQ ID NO 756
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 756
gcuugaauuu gcuaaugaca caaaa                                          25

<210> SEQ ID NO 757
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 757
gcaauugcgu ggaauauucc cucua                                          25

<210> SEQ ID NO 758
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 758
cguggaauau ucccucuaug guguu                                          25

<210> SEQ ID NO 759
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 759
gguguucgac agcagcgcuu uguuu                                             25

<210> SEQ ID NO 760
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 760
gcuauuauuc ugaugauggc aacua                                             25

<210> SEQ ID NO 761
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 761
cccguucuac gcgaucaaug cuuaa                                             25

<210> SEQ ID NO 762
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 762
gguugugucc uaggacuugu uaauu                                             25

<210> SEQ ID NO 763
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 763
ccucuuuguu cguagaggac ugcaa                                             25

<210> SEQ ID NO 764
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 764
gcgcuuggca uccauugcuu uuaau                                             25

```
<210> SEQ ID NO 765
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 765
gguugaucaa cuuaauagua guuau                                             25

<210> SEQ ID NO 766
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 766 ccuuggugu gacucaggag uacau                                              25

<210> SEQ ID NO 767
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 767
ccauggugcc aauuuacgcc aggau                                             25

<210> SEQ ID NO 768
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 768
ggugccaauu uacgccagga ugauu                                             25

<210> SEQ ID NO 769
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 769
cgccaggaug auucuguacg uaauu                                             25

<210> SEQ ID NO 770
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 770
gccaggauga uucuguacgu aauuu                                             25

<210> SEQ ID NO 771
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 771
ggaugauucu guacguaauu uguuu                                              25

<210> SEQ ID NO 772
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 772
cguaauuugu uugcgagcgu gaaaa                                              25

<210> SEQ ID NO 773
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 773
gcgagcguga aaagcucuca aucau                                              25

<210> SEQ ID NO 774
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 774
ccagguuuug gaggugacuu uaauu                                              25

<210> SEQ ID NO 775
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 775
ggcagucgua gugcacguag ugcua                                              25

<210> SEQ ID NO 776
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 776
gcagucguag ugcacguagu gcuau                                              25

<210> SEQ ID NO 777
<211> LENGTH: 25
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 777
cguagugcua uugaggauuu gcuau                                         25

<210> SEQ ID NO 778
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 778
gcugauccug guuauaugca agguu                                         25

<210> SEQ ID NO 779
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 779
gguuauaugc aagguuacga ugauu                                         25

<210> SEQ ID NO 780
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 780
gguccagcau cagcucguga ucuua                                         25

<210> SEQ ID NO 781
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 781
ccagcaucag cucgugaucu uauuu                                         25

<210> SEQ ID NO 782
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 782
gcucgugauc uuauuugugc ucaau                                         25

<210> SEQ ID NO 783
<211> LENGTH: 25
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 783
ggauguuaau auggaagccg cguau                                         25

<210> SEQ ID NO 784
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 784
gguguuggcu ggacugcugg cuuau                                         25

<210> SEQ ID NO 785
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 785
gcuggacugc uggcuuaucc uccuu                                         25

<210> SEQ ID NO 786
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 786
gcuggcuuau ccuccuuugc ugcua                                         25

<210> SEQ ID NO 787
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 787
gcugcuauuc cauuugcaca gagua                                         25

<210> SEQ ID NO 788
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 788
cgguguuggc auuacucaac agguu                                         25

<210> SEQ ID NO 789
<211> LENGTH: 25
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 789
gguucuuuca gagaaccaaa agcuu                                          25

<210> SEQ ID NO 790
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 790
ccaaaagcuu auugccaaua aguuu                                          25

<210> SEQ ID NO 791
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 791
ggagcuaugc aaacaggcuu cacua                                          25

<210> SEQ ID NO 792
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 792
gcuaugcaaa caggcuucac uacaa                                          25

<210> SEQ ID NO 793
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 793
gcaaacaggc uucacuacaa cuaau                                          25

<210> SEQ ID NO 794
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 794
gcuucacuac aacuaaugaa gcuuu                                          25

<210> SEQ ID NO 795
<211> LENGTH: 25
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 795
gcuaucuaau acuuuggug cuauu                                              25

<210> SEQ ID NO 796
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 796
ggcacaaucc aagcguucug gauuu                                             25

<210> SEQ ID NO 797
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 797
gcacaaucca agcguucugg auuuu                                             25

<210> SEQ ID NO 798
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 798
cccuagcaac cacauugagg uuguu                                             25

<210> SEQ ID NO 799
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 799
ccuagcaacc acauugaggu uguuu                                             25

<210> SEQ ID NO 800
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 800
ccacauugag guuguuucug cuuau                                             25

<210> SEQ ID NO 801
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 801
cccuacuaau uguauagccc cuguu                                              25

<210> SEQ ID NO 802
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 802
ccuacuaauu guauagcccc uguua                                              25

<210> SEQ ID NO 803
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 803
gccccuguua auggcuacuu uauua                                              25

<210> SEQ ID NO 804
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 804
ccuguuaaug gcuacuuuau uaaaa                                              25

<210> SEQ ID NO 805
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 805
ggucauauac uggcucgucc uucua                                              25

<210> SEQ ID NO 806
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 806
ccuuaaugag ucuuacauag accuu                                              25

<210> SEQ ID NO 807
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 807
ggcaauuaua cuuauuacaa caaau                                        25

<210> SEQ ID NO 808
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 808
ggccguggua cauuuggcuu gguuu                                        25

<210> SEQ ID NO 809
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 809
gcugggcuug uugccuuagc ucuau                                        25

<210> SEQ ID NO 810
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 810
gcacugguug uggcacaaac uguau                                        25

<210> SEQ ID NO 811
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 811
gguuguggca caaacuguau gggaa                                        25

<210> SEQ ID NO 812
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 812
ggcacaaacu guaugggaaa acuua                                        25

<210> SEQ ID NO 813
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 813
gcacaaacug uaugggaaaa cuuaa                                                25

<210> SEQ ID NO 814
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 814
ggaaaacuua aguguaaucg uuguu                                                25

<210> SEQ ID NO 815
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 815
cguuguugug auagauacga ggaau                                                25

<210> SEQ ID NO 816
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 816
ccgcauaagg uucauguuca cuaau                                                25

<210> SEQ ID NO 817
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 817
cgcauaaggu ucauguucac uaauu                                                25

<210> SEQ ID NO 818
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 818
gcauaagguu cauguucacu aauua                                                25

<210> SEQ ID NO 819
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 819
gguugcaugc uuagggcuug uauua                                           25

<210> SEQ ID NO 820
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 820
ccaagcugau acagcugguc uuuau                                           25

<210> SEQ ID NO 821
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 821
gcugauacag cuggucuuua uacaa                                           25

<210> SEQ ID NO 822
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 822
cgaauugacg ucccaucugc agaau                                           25

<210> SEQ ID NO 823
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 823
cccugugcug uggaacuguc agcua                                           25

<210> SEQ ID NO 824
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 824
ccugugcugu ggaacuguca gcuau                                           25

<210> SEQ ID NO 825
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 825
gcuguggaac ugucagcuau ccuuu				25

<210> SEQ ID NO 826
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 826
gcuauccuuu gcugguuaua cugaa				25

<210> SEQ ID NO 827
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 827
gcugguuaua cugaaucugc uguua				25

<210> SEQ ID NO 828
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 828
gguuauacug aaucugcugu uaauu				25

<210> SEQ ID NO 829
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 829
gccaaacagg acgcagcuca gcgaa				25

<210> SEQ ID NO 830
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 830
ccaaacagga cgcagcucag cgaau				25

<210> SEQ ID NO 831
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 831
gguugcuaca uaaggaugga ggaau				25

<210> SEQ ID NO 832
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 832
cggcacucaa guuuauucgc gcaaa                                           25

<210> SEQ ID NO 833
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 833
ccaacacacu augucagggu uacau                                           25

<210> SEQ ID NO 834
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 834
ggguuacauu uucagaccccc aacau                                          25

<210> SEQ ID NO 835
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 835
gguaucuacg uucgggucau cauuu                                           25

<210> SEQ ID NO 836
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 836
gccaaccugu uucugaguac cauau                                           25

<210> SEQ ID NO 837
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 837
ccaaccuguu ucugaguacc auauu                                           25

```
<210> SEQ ID NO 838
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 838
ccauauuacu cuagcuuugc uaaau                                             25

<210> SEQ ID NO 839
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 839
gcuaaaucuc acugaugaag auuua                                             25

<210> SEQ ID NO 840
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 840
cgccuugcug cgcaaaacuc uuguu                                             25

<210> SEQ ID NO 841
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 841
gcugcgcaaa acucuuguuc uuaau                                             25

<210> SEQ ID NO 842
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 842
cgcaaaacuc uuguucuuaa ugcau                                             25

<210> SEQ ID NO 843
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 843
ggauuggcuu cucguucagg gauuu                                             25
```

<210> SEQ ID NO 844
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 844
gcuucucguu cagggauuuu cccuu                                              25

<210> SEQ ID NO 845
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 845
cguucaggga uuucccuuu accau                                               25

<210> SEQ ID NO 846
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 846
cccuuuacca uaguggccuc ccuuu                                              25

<210> SEQ ID NO 847
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 847
ccuuuaccau aguggccucc cuuua                                              25

<210> SEQ ID NO 848
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 848
cgcaauuaca ucauuacaau gccau                                              25

<210> SEQ ID NO 849
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 849
ccucaacaaa uguuuguuac uccuu                                              25

<210> SEQ ID NO 850

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 850 ccaucgguc uuccaaucag gguaa                                          25

<210> SEQ ID NO 851
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 851
gguaauaaac aaauuguuca uucuu                                         25

<210> SEQ ID NO 852
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 852
ggcuuucucg gcgucuuuau uuaaa                                         25

<210> SEQ ID NO 853
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 853
ccuauuauua cugcuacguc aagau                                         25

<210> SEQ ID NO 854
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 854
ccuuguucug uauaacuuuu uauua                                         25

<210> SEQ ID NO 855
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 855
gguguacauu auccaacugg aaguu                                         25

<210> SEQ ID NO 856
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 856
ccucauaaua cuuugguuug uagau                                            25

<210> SEQ ID NO 857
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 857
ccaaaccauu auuauuaga aacuu                                             25

<210> SEQ ID NO 858
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 858
gcguugcagc uguucucguu guuuu                                            25

<210> SEQ ID NO 859
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 859
cguugcagcu guucucguug uuuuu                                            25

<210> SEQ ID NO 860
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 860
gcagcuguuc ucguuguuuu uauuu                                            25

<210> SEQ ID NO 861
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 861
ccacuuauau agagugcacu uauau                                            25

<210> SEQ ID NO 862
<211> LENGTH: 25
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 862
gcacuuauau uagccguuuu aguaa                                   25

<210> SEQ ID NO 863
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 863
ccguuuuagu aagauuagcc uaguu                                   25

<210> SEQ ID NO 864
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 864
cguuuuagua agauuagccu aguuu                                   25

<210> SEQ ID NO 865
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 865
cgcgcgauuc aguccucuu cacau                                    25

<210> SEQ ID NO 866
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 866
gcgcgauuca guccucuuc acaua                                    25

<210> SEQ ID NO 867
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 867
cgcgauucag uccucuuca cauaa                                    25

<210> SEQ ID NO 868
<211> LENGTH: 25
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 868
gcgauucagu uccucuucac auaau                                             25

<210> SEQ ID NO 869
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 869
cgccccgagc ucgcuuaucg uuuaa                                             25

<210> SEQ ID NO 870
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 870
cguuuaagca gcucugcgcu acuau                                             25

<210> SEQ ID NO 871
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 871
ggaucccgug uagaggcuaa uccau                                             25

<210> SEQ ID NO 872
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 872
gaucccgugu agaggcuaau ccauu                                             25

<210> SEQ ID NO 873
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 873
ggacauaugg aaaacgaacu auguu                                             25

<210> SEQ ID NO 874
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 874
ccguaguaug ugcuauaaca cucuu                                    25

<210> SEQ ID NO 875
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 875
ggcuuuccuu acggcuacua gauua                                    25

<210> SEQ ID NO 876
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 876 gcuuccuua cggcuacuag auuau                                     25

<210> SEQ ID NO 877
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 877
gcuacuagau uaugugugca augua                                    25

<210> SEQ ID NO 878
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 878
cccuguuagu ucagcccgca uuaua                                    25

<210> SEQ ID NO 879
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 879
cccaucccgu aguaugacug ucuau                                    25

<210> SEQ ID NO 880
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 880
ggccaucuuc cauggcgcua ucaau                                    25

<210> SEQ ID NO 881
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 881
gccaucuucc auggcgcuau caaua                                    25

<210> SEQ ID NO 882
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 882
ccaucuucca uggcgcuauc aauau                                    25

<210> SEQ ID NO 883
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 883
ccaauugauc uagcuuccca gauaa                                    25

<210> SEQ ID NO 884
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 884
ggcauuguag cagcuguuuc agcua                                    25

<210> SEQ ID NO 885
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 885
gcauuguagc agcuguuuca gcuau                                    25

<210> SEQ ID NO 886
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 886
gcuguuucag cuaugaugug gauuu                                    25

<210> SEQ ID NO 887
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 887
ggauuuccua cuuugugcag aguau                                    25

<210> SEQ ID NO 888
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 888
cggcuguuua ugagaacugg aucau                                    25

<210> SEQ ID NO 889
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 889
ccaguguaac ugcuguugua accaa                                    25

<210> SEQ ID NO 890
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 890
ccaccucaaa auggcuggca ugcau                                    25

<210> SEQ ID NO 891
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 891
gcaugcauuu cggugcuugu gacua                                    25

<210> SEQ ID NO 892
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 892
cggugcuugu gacuacgaca gacuu                                         25

<210> SEQ ID NO 893
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 893
gcuugugacu acgacagacu uccua                                         25

<210> SEQ ID NO 894
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 894
gcuuuaaaaa uggugaagcg gcaaa                                         25

<210> SEQ ID NO 895
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 895
ggaacuaauu ccggcguugc cauuu                                         25

<210> SEQ ID NO 896
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 896
ccggcguugc cauuuaccau agaua                                         25

<210> SEQ ID NO 897
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 897
cggcguugcc auuuaccaua gauau                                         25

<210> SEQ ID NO 898
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 898
```
ggcguugcca uuuaccauag auaua                                       25

<210> SEQ ID NO 899
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 899
gcguugccau uuaccauaga uauaa                                       25

<210> SEQ ID NO 900
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 900
gcagguaauu acaggagucc gccua                                       25

<210> SEQ ID NO 901
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 901
gguaauuaca ggaguccgcc uauua                                       25

<210> SEQ ID NO 902
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 902
ggaguccgcc uauuacggcg gauau                                       25

<210> SEQ ID NO 903
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 903
gccuauuacg gcggauauug aacuu                                       25

<210> SEQ ID NO 904
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 904
ggcggauauu gaacuugcau ugcuu                                        25

<210> SEQ ID NO 905
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 905
gcauugcuuc gagcuuaggc ucuuu                                        25

<210> SEQ ID NO 906
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 906
gcuucgagcu uaggcucuuu aguaa                                        25

<210> SEQ ID NO 907
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 907
ggcagggugu accucuuaau gccaa                                        25

<210> SEQ ID NO 908
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 908
gcagggugua ccucuuaaug ccaau                                        25

<210> SEQ ID NO 909
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 909
ggguauuggc ggagacagga cagaa                                        25

<210> SEQ ID NO 910
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 910
gguauuggcg gagacaggac agaaa                                        25

<210> SEQ ID NO 911
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 911
ggcggagaca ggacagaaaa auuaa                                   25

<210> SEQ ID NO 912
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 912
gcggagacag gacagaaaaa uuaau                                   25

<210> SEQ ID NO 913
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 913
cggagacagg acagaaaaau uaaua                                   25

<210> SEQ ID NO 914
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 914
ggacagaaaa auuaauaccg ggaau                                   25

<210> SEQ ID NO 915
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 915
gcagcacucc cauuccgggc uguua                                   25

<210> SEQ ID NO 916
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 916
ccgggcuguu aaggauggca ucguu                                   25

<210> SEQ ID NO 917
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 917
cgggcuguua aggauggcau cguuu                                       25

<210> SEQ ID NO 918
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 918
ggauggcauc guuugggucc augaa                                       25

<210> SEQ ID NO 919
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 919
ggcgccacug augcuccuuc aacuu                                       25

<210> SEQ ID NO 920
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 920
gcgccacuga ugcuccuuca acuuu                                       25

<210> SEQ ID NO 921
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 921
cgccacugau gcuccuucaa cuuuu                                       25

<210> SEQ ID NO 922
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 922
gggacgcgga acccuaacaa ugauu                                       25

```
<210> SEQ ID NO 923
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 923
ccgguacuaa gcuuccuaaa aacuu                                          25

<210> SEQ ID NO 924
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 924
ccacauugag gggacuggag gcaau                                          25

<210> SEQ ID NO 925
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 925
gggacuggag gcaauaguca aucau                                          25

<210> SEQ ID NO 926
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 926
ggaggcaaua gucaaucauc uucaa                                          25

<210> SEQ ID NO 927
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 927
cggagcagua ggaggugauc uacuu                                          25

<210> SEQ ID NO 928
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 928
ggagcaguag gaggugaucu acuuu                                          25

<210> SEQ ID NO 929
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 929
ccuugaucuu cugaacagac uacaa                                               25

<210> SEQ ID NO 930
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 930
ggcaaaguaa agcaaucgca gccaa                                               25

<210> SEQ ID NO 931
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 931
gcaaaguaaa gcaaucgcag ccaaa                                               25

<210> SEQ ID NO 932
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 932
cgcagccaaa aguaaucacu aagaa                                               25

<210> SEQ ID NO 933
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 933
gcgccacaag cgcacuucca ccaaa                                               25

<210> SEQ ID NO 934
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 934
cgccacaagc gcacuuccac caaaa                                               25

<210> SEQ ID NO 935
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 935
gcacuuccac caaaaguuuc aacau                                              25

<210> SEQ ID NO 936
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 936
cgcggaccag gagaccucca gggaa                                              25

<210> SEQ ID NO 937
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 937
gcggaccagg agaccuccag ggaaa                                              25

<210> SEQ ID NO 938
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 938
ccuccaggga aacuuuggug aucuu                                              25

<210> SEQ ID NO 939
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 939
ccagggaaac uuuggugauc uucaa                                              25

<210> SEQ ID NO 940
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 940
ccccaaauug cugagcuugc uccua                                              25

<210> SEQ ID NO 941
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 941
gcuugcuccu acagccagug cuuuu                                              25

<210> SEQ ID NO 942
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 942
ccuacagcca gugcuuuuau gggua                                              25

<210> SEQ ID NO 943
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 943
gcuuuuaugg guaugucgca auuua                                              25

<210> SEQ ID NO 944
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 944
cgcaauuuaa acuuacccau cagaa                                              25

<210> SEQ ID NO 945
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 945
gcaacccugu guacuuccuu cggua                                              25

<210> SEQ ID NO 946
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 946
ccuucgguac aguggagcca uuaaa                                              25

<210> SEQ ID NO 947
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 947
gguuggagcu ucuugagcaa aauau                                              25

<210> SEQ ID NO 948
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 948
ggagcuucuu gagcaaaaua uugau                                              25

<210> SEQ ID NO 949
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 949
ggaaaagaaa caaaaggcac caaaa                                              25

<210> SEQ ID NO 950
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 950
cguccaagug uucagccugg uccaa                                              25

<210> SEQ ID NO 951
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 951
ccaaugauug auguuaacac ugauu                                              25

<210> SEQ ID NO 952
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 952
cccagaaucu gcuuaagaag uug                                                23

<210> SEQ ID NO 953
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 953
gcccauucau ggauaaugcu auu                                            23

<210> SEQ ID NO 954
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 954
cccauucaug gauaaugcua uua                                            23

<210> SEQ ID NO 955
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 955
cgccauuacu gcaccuuaug uag                                            23

<210> SEQ ID NO 956
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 956
guguuguaca gaguuuuucc uua                                            23

<210> SEQ ID NO 957
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 957
ggcgacuuua ugucuacaau uau                                            23

<210> SEQ ID NO 958
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 958
cuguuaguaa gcuucuagau aca                                            23

<210> SEQ ID NO 959
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 959
aacauuuaac uucuuguuag auu                     23

<210> SEQ ID NO 960
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 960
cugugucuuu ugauuaucuu auu                     23

<210> SEQ ID NO 961
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 961
cgcaauacgu aaagcuaaag auu                     23

<210> SEQ ID NO 962
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 962
ggguguugau uauacuaaga agu                     23

<210> SEQ ID NO 963
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 963
gacacuuuag augauaucuu aca                     23

<210> SEQ ID NO 964
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 964
cgcacuaaug gugguuacaa uuc                     23

<210> SEQ ID NO 965
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 965
uacuuucuua cacagauucu auu                                          23

<210> SEQ ID NO 966
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 966
gaccuaucug cuuucuaugu uaa                                          23

<210> SEQ ID NO 967
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 967
gugaugcuau uaguuugagu uuu                                          23

<210> SEQ ID NO 968
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 968
aucuuaugau acuaaucuua aua                                          23

<210> SEQ ID NO 969
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 969
ccccauugaa cucgaaaaua aau                                          23

<210> SEQ ID NO 970
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 970
cccauugaac ucgaaaauaa auu                                          23

<210> SEQ ID NO 971
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 971
cccuaaguau caagucauug ucu                                          23

<210> SEQ ID NO 972
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 972
ggcuucauuu uauuucaaag aau                                          23

<210> SEQ ID NO 973
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 973
cacuagcuua cuuuagugau uca                                          23

<210> SEQ ID NO 974
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 974
cccaagguuu gaaaaaguuc uac                                          23

<210> SEQ ID NO 975
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 975
aagguuugaa aaaguucuac aaa                                          23

<210> SEQ ID NO 976
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 976
cagguacauu gcauuauuuc uuu                                          23

<210> SEQ ID NO 977
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 977
```
gcgcuuuuac aaaucuagau aag                                              23

<210> SEQ ID NO 978
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 978
ggcuucaguu aaccaaauug ucu                                              23

<210> SEQ ID NO 979
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 979
cgcauugcau gccguaagug uaa                                              23

<210> SEQ ID NO 980
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 980
cucaaagcua cgcgcuaaug aua                                              23

<210> SEQ ID NO 981
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 981
ccgcaucuug gacuuuaaag uuc                                              23

<210> SEQ ID NO 982
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 982
cucuucuauu auauuaauaa agu                                              23

<210> SEQ ID NO 983
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 983
ugccucuaau aucuuuguua uua                              23

<210> SEQ ID NO 984
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 984
cucuaauauc uuuguuauua aca                              23

<210> SEQ ID NO 985
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 985
cagcucuuag aaacucuuua acu                              23

<210> SEQ ID NO 986
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 986
cggaagugaa gaugauacuu uua                              23

<210> SEQ ID NO 987
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 987
aagugaagau gauacuuuua uua                              23

<210> SEQ ID NO 988
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 988
ggcuaugacu ucuauguaua agc                              23

<210> SEQ ID NO 989
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 989
uacagguaua gcuauaucug uua                              23

<210> SEQ ID NO 990
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 990
ccccaaucua aagauuccaa uuu                                            23

<210> SEQ ID NO 991
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 991
cccaaucuaa agauuccaau uuu                                            23

<210> SEQ ID NO 992
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 992
cugugauguu accuacuuug aaa                                            23

<210> SEQ ID NO 993
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 993
cccaguguua uugguguuua uca                                            23

<210> SEQ ID NO 994
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 994
caguguuauu gguguuuauc aua                                            23

<210> SEQ ID NO 995
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 995
uacaacucuu ugagaaguac uuu                                            23

<210> SEQ ID NO 996
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 996
cuccucuaac gcuuuucuug auu                                              23

<210> SEQ ID NO 997
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 997
uacuaugugu gacaucaaac aaa                                              23

<210> SEQ ID NO 998
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 998
ugggauuuca ugcuuaaaac auu                                              23

<210> SEQ ID NO 999
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 999
gggauuucau gcuuaaaaca uug                                              23

<210> SEQ ID NO 1000
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1000
cacugcauau gccaauagug ucu                                              23

<210> SEQ ID NO 1001
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1001
gggugcuaau ggcaacaaga uug                                              23

-continued

```
<210> SEQ ID NO 1002
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1002
ccccaaauuu guugauaaau acu                                               23

<210> SEQ ID NO 1003
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1003
cgguugcuuu guagaugaua ucg                                               23

<210> SEQ ID NO 1004
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1004
uugcuuugua gaugauaucg uua                                               23

<210> SEQ ID NO 1005
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1005
cucucacaaa gcaugaagau aua                                               23

<210> SEQ ID NO 1006
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1006
gucuacuuac aguauauaga aaa                                               23

<210> SEQ ID NO 1007
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1007
accacucaau cguaauuaug uuu                                               23

<210> SEQ ID NO 1008
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1008
uacaagucua guacaacgua uaa                                              23

<210> SEQ ID NO 1009
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1009
cacuaauuau gaucuuucaa uua                                              23

<210> SEQ ID NO 1010
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1010
auggaguaag gcagucuuua uuu                                              23

<210> SEQ ID NO 1011
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1011
cacaugcuaa caacauuaac aga                                              23

<210> SEQ ID NO 1012
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1012
gcccaaaaag guauucuuug ugu                                              23

<210> SEQ ID NO 1013
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1013
cacucuuuga guccuuagag uuu                                              23

<210> SEQ ID NO 1014
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1014
cugcgguuau gauuaugucu aca                                              23

<210> SEQ ID NO 1015
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1015
cgguucauuu gacaaagucu aug                                              23

<210> SEQ ID NO 1016
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1016
uucauuugac aaagucuaug aua                                              23

<210> SEQ ID NO 1017
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1017
uaguaugaua gaggauauug auu                                              23

<210> SEQ ID NO 1018
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1018
guguuauaag accuuugaua uuu                                              23

<210> SEQ ID NO 1019
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1019
gggauuauga acguagcaau auu                                              23

<210> SEQ ID NO 1020
<211> LENGTH: 23
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 1020
gccaucuuua uuucugauag aaa                                              23

<210> SEQ ID NO 1021
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1021
aucuuuauuu cugauagaaa aau                                              23

<210> SEQ ID NO 1022
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1022
ccgugauagu gauguuguua aac                                              23

<210> SEQ ID NO 1023
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1023
gucuucacuu gcuuauuggu uua                                              23

<210> SEQ ID NO 1024
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1024
cucaacuauu cauaacuauu uua                                              23

<210> SEQ ID NO 1025
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1025
uuccuauuga cuuaacaaug auu                                              23

<210> SEQ ID NO 1026
<211> LENGTH: 23
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1026
cucuuuaaag uucaaaaugu aaa                                              23

<210> SEQ ID NO 1027
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1027
ugccaauaug cguguuauac auu                                              23

<210> SEQ ID NO 1028
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1028
gacauguaug auccuacuac uaa                                              23

<210> SEQ ID NO 1029
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1029
gagcguugaa cuuuaugaac uua                                              23

<210> SEQ ID NO 1030
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1030
ggguacuauu aagaaaaua uag                                               23

<210> SEQ ID NO 1031
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1031
ggccguacau auucuaacau aac                                              23

<210> SEQ ID NO 1032
<211> LENGTH: 23
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1032
gccguacaua uucuaacaua acu                                              23

<210> SEQ ID NO 1033
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1033
cacuuuacuu agagcuuuuu auu                                              23

<210> SEQ ID NO 1034
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1034
caccuuuaug uacacuuaua aca                                              23

<210> SEQ ID NO 1035
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1035
ccgaagauga gauuuuagag ugg                                              23

<210> SEQ ID NO 1036
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1036
ugguccaaua ucccaguuua auu                                              23

<210> SEQ ID NO 1037
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1037
cccaguuuaa uuauaaacag ucc                                              23

<210> SEQ ID NO 1038
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1038
uugaucaacu uaauaguagu uau                                          23

<210> SEQ ID NO 1039
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1039
caggaugauu cuguacguaa uuu                                          23

<210> SEQ ID NO 1040
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1040
augauucugu acguaauuug uuu                                          23

<210> SEQ ID NO 1041
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1041
cagguuuugg aggugacuuu aau                                          23

<210> SEQ ID NO 1042
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1042
ggcuucacua caacuaauga agc                                          23

<210> SEQ ID NO 1043
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1043
ccccuguuaa uggcuacuuu auu                                          23

<210> SEQ ID NO 1044
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1044
cccuguuaau ggcuacuuua uua                                           23

<210> SEQ ID NO 1045
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1045
cacaaacugu augggaaaac uua                                           23

<210> SEQ ID NO 1046
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1046
gccgcauaag guucauguuc acu                                           23

<210> SEQ ID NO 1047
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1047
cugcgcaaaa cucuuguucu uaa                                           23

<210> SEQ ID NO 1048
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1048
cgcaaaacuc uuguucuuaa ugc                                           23

<210> SEQ ID NO 1049
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1049
ggcuuucucg gcgucuuuau uua                                           23

<210> SEQ ID NO 1050
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1050
uuguucugua uaacuuuuua uua                                              23

<210> SEQ ID NO 1051
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1051
gacauaugga aaacgaacua ugu                                              23

<210> SEQ ID NO 1052
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1052
ggcauuguag cagcuguuuc agc                                              23

<210> SEQ ID NO 1053
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1053
gccuauuacg gcggauauug aac                                              23

<210> SEQ ID NO 1054
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1054
ccgguacuaa gcuuccuaaa aac                                              23

<210> SEQ ID NO 1055
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1055
gaggcaauag ucaaucaucu uca                                              23

<210> SEQ ID NO 1056
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1056
gagcuucuug agcaaaauau uga                                         23

<210> SEQ ID NO 1057
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1057
cgcaauacgu aaagcuaaag auuau                                       25

<210> SEQ ID NO 1058
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1058
gggguugauu auacuaagaa guuu                                        24

<210> SEQ ID NO 1059
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1059
ggguguugau uauacuaaga aguuu                                       25
```

SIRNA/NANOPARTICLE FORMULATIONS FOR TREATMENT OF MIDDLE-EAST RESPIRATORY SYNDROME CORONAVIRAL INFECTION

CROSS-REFERENCE TO RELATED PATENT APPLICATIONS

This application is a U.S. national phase application of, and claims the benefit of and priority to, International Patent Application No. PCT/US2016/050590, filed Sep. 7, 2016, which claims the benefit of and priority to U.S. Provisional Patent Application No. 62/215,565, filed Sep. 8, 2015. The disclosures of these applications are expressly incorporated herein by reference in their entireties.

SEQUENCE LISTING

The instant application contains a Sequence Listing that has been submitted electronically in ASCII format and is hereby incorporated by reference in its entirety. Said ASCII copy, created on Sep. 26, 2018, is named SIR-014_P001-US_SL.txt and is 251,342 bytes in size.

FIELD OF INVENTION

The present invention provides a pharmaceutical product composition of matter comprising siRNA sequences targeting genes or single-stranded viral RNAs of Middle-East Respiratory Syndrome Corona Virus (MERS-CoV), and nanoparticle carrier systems such as Histidine-Lysine copolymers (HKP), or Spermine-Liposome conjugates (SLiC), or a lung tissue targeted moiety, such as a peptide, a nucleotide, a small molecule, and an antibody. The present invention also involves in methods of use for this pharmaceutical product, including formulations of siRNA/nanoparticle carrier, their process development and specific delivery routes and regimens. This invention presents a novel therapeutic agent for treatment of MERS-CoV infection.

BACKGROUND

MERS-CoV Virus Disease: Biology and Pathology

Middle East respiratory syndrome (MERS) is a highly lethal respiratory disease caused by a novel single-stranded, positive-sense RNA betacoronavirus, MERS-CoV. Dromedary camels, hosts for MERS-CoV, are implicated in direct or indirect transmission to human beings, although the exact mode of transmission is unknown. Recent studies support that camels serve as the primary source of the MERS-CoV infecting humans, while bats may be the ultimate reservoir of the virus. The virus was first isolated from a patient who died from a severe respiratory illness in June, 2012, in Jeddah, Saudi Arabia. As of May 31, 2015, 1180 laboratory-confirmed cases (483 deaths; 40% mortality) have been reported to WHO (Zumbla A. et al. 2015). The Centers for Disease Control and Prevention (CDC) has labelled it as a transmissible disease from human-to-humans. (Jalal S. 2015). Although most cases of MERS have occurred in Saudi Arabia and the United Arab Emirates, cases have been reported in Europe, the USA, and Asia in people who travelled from the Middle East or their contacts. Clinical features of MERS range from asymptomatic or mild disease to acute respiratory distress syndrome and multiorgan failure, resulting in death, especially in individuals with underlying comorbidities. No specific drug treatment exists for MERS and infection prevention, and control measures are crucial to prevent spread in health-care facilities (Zumbla A. Et al 2015). Clinical severity of the disease observed in humans may be explained the ability of MERS-CoV to replicate in the lower respiratory tract (de Wit E, et al. 2013) and is also related to MERS-CoV's ability to infect a broad range of cells with dipeptidyl peptidase 4 receptor (DPP4) expression, evade the host innate immune response, and induce cytokine dysregulation (Chan J F, 2015).

MERS-CoV is an enveloped single-stranded positive sense RNA virus with a genome of 30,119 nt. The genome structure of MERS-CoV is similar to other coronaviruses, with the 5' two-thirds of the genome encoding the non-structural proteins (NSPs) required for viral genome replication, the remaining 3' third of the genome encoding the structural genes that make up the virion (spike, envelope, membrane, and nucleocapsid proteins), and four accessory genes interspersed within the structural gene region. At the 5' end of the genome, there is a leader sequence (67nt), which is followed by an untranslated region (UTR). At the 3' end of the RNA genome there is another UTR, followed by a poly (A) sequence of variable length. Transcription-regulatory sequences (TRS 5' AACGAA 3') are found at the 3' end of the leader sequence and at different positions upstream of genes in the genomic 3'-proximal domain of MERS-CoV. The MERS-CoV genome contains at least 10 predicted open reading frames (ORFs): ORF1a, ORF1b, S, 3, 4a, 4b, 5, E, M and N with sixteen predicted nonstructural proteins being encoded by ORF1a/b. Several unique group-specific ORFs that are not essential for virus replication are encoded by MERS-CoV. The functions of these group-specific ORFs are unknown; however, by analogy to other coronaviruses, they may encode structural proteins or interferon antagonist genes (Totura A L, Baric R S, 2012). Open reading frames ORF2, -6, -7 and-8a are translated from subgenomic mRNAs predicted to encode the four canonical structural genes: a 180/90-kDa spike glycoprotein (S), a~23-kDa membrane glycoprotein (M), a small envelope protein (E) and a~50-kDa nucleocapsidprotein (N), respectively (Abdel-Moneim A S. 2014).

Similar to other RNA viruses, coronavirus replicate in the host cytoplasm. The replication process is initiated by the viral particle after binding with specific cellular receptors, known as S-protein mediated binding. The receptor for MERS-CoV was recently identified as dipeptidyl peptidase 4 (DDP4, also known as CD26), a protein with diverse functions in glucose homeostasis, T-cell activation, neurotransmitter function, and modulation of cardiac signaling. DPP4 is expressed in a variety of cell types, including endothelial cells (kidney, lung, small intestine, spleen) hepatocytes, enterocytes, activated leukocytes, testes, prostate and cells of the renal glomeruli and proximal tubules. DPP4 recognition is mediated by the receptor-binding domain (RBD, amino acids E367-Y606) (Pascal K, et al. 2015). Following virus entry, the coronavirus genome, a positive sense, capped and polyadenylated RNA strand, is directly translated, resulting in the synthesis of coronavirus replicase gene-encoded NSPs. Coronavirus NSPs are translated as two large polyproteins harboring proteolytic enzymes, namely papain-like and chymotrypsin-like proteinases that extensively process coronavirus polyproteins to liberate up to 16 NSPs (nsp 1-16) (Lundin A. et al. 2014). After entering into the cell, the virus specially modulates the innate immune response, antigen presentation, and mitogen-activated protein kinase.

Current Prophylaxis and Therapeutics

Although the emergence of highly pathogenic MERS-CoV highlights an urgent need for potent therapeutic and prophylactic agents, no approved antiviral treatments for any human coronavirus infections are currently available. Supportive treatment with extracorporeal membrane oxygenation and dialysis is often required in patients with organ failure. Recently, tremendous efforts have been made in the search for an effective anti-MERS-CoV agent, and a number of antiviral agents have been identified. For example, some compounds with inhibitory activities in the low micromolar range on MERS-CoV replication in cell cultures have been identified from the libraries of FDA-approved drugs. de Wilde A H. and colleges identified four compounds (chloroquine, chlorpromazine, loperamide, and lopinavir) inhibiting MERS-CoV replication in the low-micromolar range (50% effective concentrations [EC(50)s], 3 to 8 µM) (de Wilde A H et al. 2014).

Antivirals with potent in vitro activities also include neutralizing monoclonal antibodies, antiviral peptides, interferons, mycophenolic acid. It was reported that rhesus macaques treated with a cocktail of IFN-a2b with ribavirin, a nucleoside analog, exhibited reduced MERS-CoV replication and an improved clinical outcome (Falzarano D, et al. 2013). Lu L. and colleges designed and synthesized a peptide (HR2P) derived from the HR2 domain in the S2 subunit of the spike (S) protein of the MERS-CoV EMC/2012 strain. They found that HR2P could bind with the HR1 domain to form a stable six-helix bundle and thus inhibit viral fusion core formation and S protein-mediated cell-cell fusion. HR2P was demonstrated to potently inhibit infection by both pseudotyped and live MERS-CoV in different cell lines. After modification of the HR2P peptide by introducing Glu (E) and Lys (K) residues at the i to i+4 or i to i+3 arrangements, it was found that one of these HR2P analogous peptides, HR2P-M2, exhibited significantly improved stability, solubility and antiviral activity. HR2P-M2 peptide could potently inhibit infection by pseudoviruses expressing MERS-CoV S protein with or without mutation in the HR1 region, suggesting that it could be effective against most currently available MERS-CoV mutants. It was demonstrated that the HR2P-M2 peptide administered via the intranasal route could protect Ad5-hDPP4-transduced mice from challenge by MERS-CoV strains with or without mutations in the HR1 region, indicating that this peptide could be used as a nasal spray to protect high-risk populations, including healthcare workers, MERS patients' family members, and those having close contacts with the patients, from MERS-CoV infection. Intranasal application of the peptide to MERS-CoV-infected patients may suppress viral replication in epithelial cells of the respiratory tract and thus reduce the release of virions, thereby preventing the spreading of MERS-CoV to other people (Lu L. et al. 2015).

Another approach is passive administration of sera from convalescent human MERS patients or other animals to exposed or infected patients. The vast majority of camels in the Middle East have been infected with MERS-CoV, and some contain high titers of antibody to the virus. It was shown that this antibody is protective if delivered either prophylactically or therapeutically to mice infected with MERS-CoV, indicating that this may be a useful intervention in infected patients (Zhao J, et al. 2015).

In April 2014, three studies conducted by separate laboratories around the world reported the development of fully human neutralizing mAbs against MERS-CoV. All these mAbs target the RBD (receptor-binding domain) of the MERS-CoV S1 glycoprotein and they were identified from non-immune human antibody libraries. Among these antibodies, three highly potent mAbs (m336, m337, m338) were identified from a very large phage-displayed antibody Fab library that was generated by using B cells from the blood of 40 healthy donors. This library was panned against recombinant MERS-CoV RBD to enrich for high affinity binders. The three identified mAbs, all derived from the VH gene 1-69, which has been the source of many other antiviral antibodies, exhibited exceptionally potent activity and neutralized pseudotyped MERS-CoV with 50% inhibitory concentration (IC50), ranging from 0.005 to 0.017 mg/ml. The most potent mAb, m336, inhibited>90% MERS-CoV pseudovirus infection (IC90) in DPP4-expressing Huh-7 cells at a concentration of 0.039 mg/ml. Similarly, m336 showed the most potent live MERS-CoV neutralizing activity in inhibiting the formation of MERS-CoV-induced CPE during live MERS-CoV infection of permissive Vero E6 cells, with an IC50 of 0.07 mg/ml.

In vivo studies have shown that this mAb is very effective in protecting MERS-CoV-susceptible animals from viral challenge (unpublished data), suggesting that the m336m mAb is a very promising drug candidate for the urgent treatment of MERS-CoV-infected patients (Tianlei Ying et al. 2015). Lu L. et colleges performed in vitro studies demonstrating that the combination of HR2P-M2 peptide with m336 mAb exhibited a strong synergistic effect against MERS-CoV infection (unpublished data). This observation suggests that intranasal administration of HR2P-M2 peptide combined with intravenous administration of m336 mAb may be a powerful strategy for treatment of MERS patients (Lu L. et al. 2015).

Jiang and colleges also identified two potent RBD-specific neutralizing mAbs, MERS-4 and MERS-27, by using a non-immune yeast-displayed scFv library to screen against the recombinant MERS-CoV RBD. The most potent mAb, MERS-4, neutralized the pseudotyped MERS-CoV infection in DPP4-expressing Huh-7 cells with an IC50 of 0.056 mg/ml and inhibited the formation of MERS-CoV-induced CPE during live MERS-CoV infection of permissive Vero E6 cells with an IC50 of 0.5 mg/ml. Tang et colleges identified neutralizing mAbs by using a non-immune phage-displayed scFv library. The panning was performed by sequentially using MERS-CoV spike-containing paramagnetic proteoliposomes and MERS-CoV S glycoprotein-expressing 293T cells as antigens. A panel of 7 anti-S1 scFvs was identified and expressed in both scFv-Fc and IgG1 formats, and their neutralizing activity against pseudotyped MERS-CoV in DPP4-expressing 293T cells, as well as live MERS-CoV infection in Vero cells, was measured. The most potent antibody, 3B11, neutralized live MERS-CoV in the plaque reduction neutralization tests with an IC50 of 1.83 mg/ml and 3.50 mg/ml in the scFv-Fc and IgG format, respectively (Tianlei Ying et al. 2015).

Fully Human Antibody and Humanized Mouse Model

Pascal K. and colleges used the VelocImmune platform (a mouse that expresses human antibody-variable heavy chains and κ light chains) to generate a panel of fully human, noncompeting monoclonal antibodies that bind to MERS-CoV S protein and inhibit entry into target cells. It was showed that two of these antibodies (REGN3051 and REGN3048) can potently neutralize pseudoparticles generated with all clinical MERS-CoV S RBD variants isolated to date. Authors demonstrated that the fully human VelocImmune antibodies neutralize infectious MERS-CoV significantly more efficient than published monoclonals isolated using traditional methods. They also developed a novel humanized model for MERS-CoV infection. They replaced the 79 kb of the mouse Dpp4 gene with 82 kb of its human ortholog. The resulting mice express fully human DPP4 under the control of the mouse regulatory elements, to preserve the proper expression regulation and protein tissue distribution and showed that these antibodies can prevent and treat MERS-CoV infection in vivo (Pascal K E et al. 2015).

Coronaviruses

Coronaviruses are enveloped viruses and their positive strand RNA genome, the largest of all RNA viruses, encodes for as many as 16 non-structural proteins (NSPs), 4 major structural proteins, and up to 8 accessory proteins. Many of these proteins provide essential, frequently enzymatic, functions during the viral life cycle, such as coronavirus protease or RNA-dependent RNA polymerase (RdRp) activities. For example, the spike (S) protein mediates binding of different HCoVs to their specific cellular receptors, an event associated with preferential virus tropism for either ciliated or non-ciliated cells of the airway epithelium. The S protein also mediates fusion between lipids of the viral envelope and the host cell plasma membrane or membranes of endocytic vesicles to promote delivery of viral genomic RNA into the cytoplasm. Following virus entry, the coronavirus genome, a positive sense, capped and polyadenylated RNA strand, is directly translated, resulting in the synthesis of coronavirus replicase gene-encoded NSPs. Coronavirus NSPs are translated as two large polyproteins harboring proteolytic enzymes, namely papain-like and chymotrypsin-like proteinases that extensively process coronavirus polyproteins to liberate up to 16 NSPs (nsp 1-16). These proteolytic functions are considered essential for coronavirus replication. Likewise, the coronavirus RdRp activities, which reside in nsp8 and nsp12, are considered essential for coronavirus replication. Coronaviruses encode an array of RNA-processing enzymes. These include a helicase activity linked to an NTPase activity in nsp13, a 3'-5'-exonuclease activity linked to a N7-methyltransferase activity in nsp14, an endonuclease activity in nsp15, and a 2'-O-methyltransferase activity in nsp16.

Like all positive strand RNA viruses, coronaviruses synthesize viral RNA at organelle-like structures in order to compartmentalize this critical step of the viral life cycle to a specialized environment that is enriched in replicative viral and host-cell factors, and at the same time protected from antiviral host defense mechanisms. There is now a growing body of knowledge concerning the involvement, rearrangement and requirement of cellular membranes for RNA synthesis of a. number of positive-strand RNA viruses, including coronaviruses. Three coronaviral NSPs, i.e., nsp3, nsp4, and nsp6 are thought to participate in formation of these sites for viral RNA synthesis. In particular, these proteins contain multiple trans-membrane domains that are thought to anchor the coronavirus replication complex through recruitment of intracellular membranes to form a reticulovesicular network (RVN) of modified, frequently paired, membranes that includes convoluted membranes and double membrane vesicles (DVM) interconnected via the outer membrane with the rough ER.

Culture Systems

MERS-CoV can replicate in different mammalian cell lines. In humans, it can replicate in the respiratory tract (lung adenocarcinoma cell line A549, embryonic fibroblast cell line HFL and polarized airway epithelium cell line Calu-3), kidney (embryonic kidney cell line; HEK), liver cells (hepatocellular carcinoma cell line; Huh-7), and the intestinal tract (colorectal adenocarcinoma cell line; Caco-2). MERS-CoV can also infect cell lines originating from primates, pigs, bats, civet cats and rabbits (Chan et al. 2013).

Additional Mouse Models

Zhao J and colleges described a novel approach to developing a mouse model for MERS by transducing mice with a recombinant, nonreplicating adenovirus expressing the hDPP4 receptor. After infection with MERS-CoV, mice develop an interstitial pneumonia. Similar to infected patients, Ad5-hDPP4-transduced mice with normal immune systems developed mild disease whereas immunocompromised mice, like patients with underlying diseases, were more profoundly affected. It was shown that these transduced, infected mice can be used to determine antivirus immune responses and to evaluate anti-MERS-CoV vaccines and therapies (Zhao J, et al. 2014).

Two Mouse Models have been developed Pascal K et al. In the first, a modified adenovirus expressing huDPP4 was administered intranasally to mice leading to huDPP4 expression in all cells of the lung, not just those that natively express DPP4. In this model, mice showed transient huDPP4 expression and mild lung disease. In the second model, a transgenic mouse was produced to expresses huDPP4 in all cells of the body, which in not physiologically relevant. In this model, MERS-CoV infection leads to high levels of viral RNA and inflammation in the lungs, and also significant inflammation and viral RNA in the brains of infected mice. However, no previous reports have documented tropism of MERS-CoV to the brains of an infected host, suggesting that studying pathogenesis of MERS-CoV in this model is limited.

RNAi and siRNA

RNA interference (RNAi) is a sequence-specific RNA degradation process that provides a direct way to knock-down, or silence, theoretically any gene. In naturally occurring RNA interference, a double stranded RNA is cleaved by an RNase III/helicase protein, Dicer, into small interfering RNA (siRNA) molecules, a dsRNA of 19-23 nucleotides (nt) with 2-nt overhangs at the 3' ends. These siRNAs are incorporated into a multicomponent-ribonuclease called RNA-induced-silencing-complex (RISC). One strand of siRNA remains associated with RISC, and guides the complex towards a cognate RNA that has sequence complementary to the guider ss-siRNA in RISC. This siRNA-directed endonuclease digests the RNA, thereby inactivating it. Studies have revealed that the use of chemically synthesized 21-25-nt siRNAs exhibit RNAi effects in mammalian cells, and the thermodynamic stability of siRNA hybridization (at terminals or in the middle) plays a central role in determining the molecule's function.

Importantly, it is presently not possible to predict with high degree of confidence which of many possible candidate siRNA sequences potentially targeting an mRNA sequence of a disease gene will, in fact, exhibit effective RNAi activity. Instead, individually specific candidate siRNA polynucleotide or oligonucleotide sequences must be generated and tested to determine whether the intended interference with expression of a targeted gene has occurred.

Target Selection

MERS-CoV is enveloped single-stranded positive-sense RNA viruses, belonging to genus Betacoronavirus. The length of the genome is around 30 k nt. The genome contains 10 predicted open reading frames (ORFs): ORF1a, ORF1b, Spike (S) Protein, 3, 4a, 4b, 5, Envelope (E) Protein, Membrane (M) Protein and Nucleocapsid (N) Protein, with 5' two third of the genome (ORF1a, ORF1b) encoding 16 non-structure proteins (nsp1-16), and rest 3' third of the genome encoding 4 structure proteins (S, E, M and N proteins).

The spike (S) protein of MERS-CoV is a glycoprotein with a molecular weight of 180/190 kDa, which is an important determinant of virus virulence and host range. Trimers of S protein form the spikes on the MERS-CoV envelope, which are responsible for the receptor binding and membrane fusion. Similar to the HIV envelope (env) and influenza hemagglutinin (HA), S proteins of MERS-CoV are Class I viral fusion proteins, which requires the protease cleavage between the S1 and S2 domains to allow the conformational changes in S2, and initiate the virus entry and syncytia formation. Dipeptidyl peptidase 4 (DDP4, or CD26), a protein with diverse functions in glucose homeostasis, T-cell activation, etc., has been identified as the receptor of MERS-CoV on the host cells. The recognition of DPP4 is mediated by the receptor-binding domain (RBD, aa E367-Y606) of the S protein. DPP4 is expressed in a variety of cell types. It has been discovered on the human cell surface in the airways (such as the lungs) and kidneys recently.

After entry into the cell, two polyproteins, pp1a and pp1ab of MERS-CoV express and undergo cotranslational proteolytic processing into the proteins that form the viral replication complex. During this processing, the activity of nsp-3, papain-like protease ($PL^{pro}$) and nsp-5, 3C-like proteinase ($3CL^{pro}$) are critical for the generation of 16 non-structural proteins from the polyprotein. However, based on the MERS-CoV genome sequences analysis and calculation, we found several siRNA candidates (MPL1-6) match $PL^{pro}$ as the target, but no good candidate matches $3CL^{pro}$. Meanwhile, the recent studies showed that MERS-CoV $PL^{pro}$ also has the function to inhibit the innate immune response to viral infection by decreasing the levels of ubiquitinated and ISGylated host cell proteins and down-regulating the cytokines, such as CCLS and IFN-β in stimulated cells.

MERS-CoV RNA-dependent RNA polymerase (RdRp), encoding by nsp-12, is the most important component of viral replication complex. This complex is responsible for both the transcription of the nested subgenomic mRNAs and the replication of the genomic positive-strand RNA. Both processes take place in the cytoplasm. In the viral mRNA transcription, the negative-strand RNAs generate from genomic RNA at first, and then transcribe a set of 3'-coterminal nested subgenomic mRNAs by the replication complex, with a common 5' "leader" sequence (67nt) derived from the 5' end of the genome. The newly synthetic genomic RNAs are produced by the taking the negative-strand RNAs as the template.

BRIEF DESCRIPTION OF THE FIGURES

FIG. 1. The genome structure of MERS-CoV MERS-CoV is enveloped single-stranded positive-sense RNA viruses, belonging to genus Betacoronavirus, with a genome of ~30K nt. The genome contains 10 predicted open reading frames (ORFs): ORF1a, ORF1b, Spike (S) Protein, 3, 4a, 4b, 5, Envelope (E) Protein, Membrane (M) Protein and Nucleocapsid (N) Protein with 16 predicted nonstructural proteins being encoded by ORF1a/b.

FIG. 2. The life cycle of MERS. After binding to the receptor, viral RNA and proteins of MERS-CoV are synthesized entirely in the cytoplasm. Two polyproteins, pp1a and pp1ab undergo cotranslational proteolytic processing into the proteins that form the viral replication complex. This complex is used to produce the negative-strand RNA from genomic RNA, and transcribe a 3'-coterminal set of nested subgenomic mRNAs from the negative-strand RNA, which have a common 5' "leader" sequence derived from the 5' end of the genome. This viral replication complex is also used to produce the positive-strand genomic RNA taking the negative-strand RNA as the template.

FIG. 3. Special design of siRNA sequences targeting critical viral genes: Papain like protein ($PL^{pro}$) specific siRNA, total 6 active siRNAs (MPL1-6); RNA dependent RNA protease (RDRP) specific siRNA, total 5 active siRNAs (MRR1-5) and Spike protein specific siRNA, total 8 active siRNAs (MSP1-8). FIG. 3 discloses SEQ ID NOS 1-2, 132, 4-12, 700, and 13-18, respectively, in order of columns.

FIG. 4. Histidine-Lysine co-polymer enhances topical and subcutaneous siRNA deliveries in vivo. The self-assembled HKP/siRNA nanoparticles (average 150 nm in diameter) can be dissolved in aqueous solution, can be lyophilized into dry powder, and can be redissovled and mixed with methylcellulose, or with RNAse free water. HKP/siRNA nanoparticle delivery to mouse respiratory track: upper airway, bronchi, alveoli.

FIG. 5. Comparison of target knockdown of lung endogenous gene among HKP, DOTAP and D5W after oral tracheal deliveries of siRNA with three different dosing regimens. HKP demonstrated the efficient siRNA-mediated knockdown of the target gene at the 20 μg dose.

FIG. 6. Intraperitoneal delivery of HKP-siRNA nanoparticle formulation demonstrated a prophylactic effect against H1N1 in the viral challenged mice (n=10). The evidence of the anti-influenza efficacy achieved by HKP-siRNA respiratory delivery support our notion that the similar approach can also be applied for anti-MERS siRNA therapeutics. The HKP-siRNA combination (siRNA103-siRNA105 with a 1:1 ratio) at a concentration of 40 μg/2ml was intraperitoneally administrated on day 1, 2, 3, 4 and 5 (2.5 mg/kg/day). The viral challenges through intranasal administrations of 2x LD50 H1N1 (A/Puerto Rico/8/1934) were conducted on day 2 ( ) for the virus only, Ribavirin and siRNA treatment groups. Ribavirin as a positive control was administered through gavages of 200u1 to provide 75 mg/kg/day dosing over days 1-5 ( ). The prophylactic efficacy of HKP-siRNA formulation is clearly better than that of Ribavirin.

FIG. 7. Intraperitoneal delivery of PAA-siRNA formulation demonstrated a therapeutic efficacy against H1N1 in the viral challenged mice (n=15). The viral challenges through intranasal administrations of 1x LD50 H1N1 (A/California/04/2009) were conducted on day 1 ( ) for the virus only, Tamiflu® and siRNA treatment groups. The H1N1 challenged mice were treated with various dosages of PAA-siRNA combination (siRNA89-siRNA103 with a 1:1 ratio), 1 mg/kg, 5 mg/kg and 10 mg/kg, through intraperitoneal administration daily, from day 2 to day 6 ( ). Adapting the same route and dosing regimen, 25 mg/kg Tamiflu® ID was also administrated daily on the H1N1 infected mice. The therapeutic efficacy of 10 mg/kg/day of PAA-siRNA combination resulted in almost equal anti-influenza activity to that of 25 mg/kg/day of Tamiflu® treatment.

FIG. 8. Scheme of the Basic Synthesis Routes and Structure of Spermine-Liposome Conjugates (SLiC) A. The synthesis route for each of the five molecules are listed with the specific liposome chain, such as, $R_1$, $R_2$, $R_3$, $R_4$ and $R_5$, conjugated at the location of $R_1H$, $R_2H$, $R_3H$, $R_4H$ and $R_5H$ respectively. B. The structures of the five SLiC species are illustrated with a spermine head and two lipid legs.

FIG. 9. Target Gene Silencing by SLiC Liposome-Mediated siRNA Delivery In Vivo. TM4-packaged siRNA specific to cyclophilin-B was selected for being tested in a Balb/c mouse model through a respiratory route of delivery. In addition to Blank control and empty TM4 control, a HKP package cyclophilin-B siRNA was used as a positive control. Three different dosage: 25, 40 and 50 μg were tested. Both 40 and 50 μg siRNA dosages achieved significant target gene silencing (N=3,*P<0.05).

FIG. 10. Evaluation of the cytokine response in the mouse lung after HKP-siRNA nanoparticles delivery. HKP-siRNA at different dosages were oraltracheally administrated in the mouse lungs. The total lung tissue were harvested for protein isolation and cytokine measurements by ELISA assay.

FIG. 11. A. Standard curve to measure protein concentration was prepared according to in-house SOP (Lowry Method); B. Total protein concentration was determined in each sample.

FIG. 12. A. Standard curve to measure TNF-α concentration was prepared according to in-house SOP (Lowry Method); B. TNF-α concentration in each sample was determined and normalized to total protein.

FIG. 13. A. Standard curve to measure IL-6 concentration was prepared according to in-house SOP (Lowry Method); B. IL-6 concentration in each sample was determined and normalized to total protein.

FIG. 14. A. Standard curve to measure IFN-α concentration was prepared according to in-house SOP (Lowry Method); B. IFN-α concentration in each sample was determined and normalized to total protein.

FIG. 15. The HKP siRNA nanoparticle aqueous solution and SLiC siRNA nanoparticle aqueous solution will be administrated through airway, using an ultrasound nebulizer generated aerosol which will have water solution particle size with broad spectrum allowing whole lung distribution.

DESCRIPTION OF THE INVENTION

The present invention provides siRNA molecules that inhibit MERS-CoV gene expression, compositions containing the molecules, and methods of using the molecules and compositions to prevent or treat MERS in a subject, such as a human patient.

SiRNA Molecules

As used herein, an "siRNA molecule" or an "siRNA duplex" is a duplex oligonucleotide, that is a short, double-stranded polynucleotide, that interferes with the expression of a gene in a cell, after the molecule is introduced into the cell, or interferes with the expression of a viral gene. For example, it targets and binds to a complementary nucleotide sequence in a single stranded (ss) target RNA molecule. SiRNA molecules are chemically synthesized or otherwise constructed by techniques known to those skilled in the art. Such techniques are described in U.S. Pat. Nos. 5,898,031, 6,107,094, 6,506,559, 7,056,704 and in European Pat. Nos. 1214945 and 1230375, which are incorporated herein by reference in their entireties. By convention in the field, when an siRNA molecule is identified by a particular nucleotide sequence, the sequence refers to the sense strand of the duplex molecule.

One or more of the ribonucleotides comprising the molecule can be chemically modified by techniques known in the art. In addition to being modified at the level of one or more of its individual nucleotides, the backbone of the oligonucleotide can be modified. Additional modifications include the use of small molecules (e.g. sugar molecules), amino acids, peptides, cholesterol, and other large molecules for conjugation onto the siRNA molecule.

The siRNA molecules of the invention target a conserved region of the genome of a MERS-CoV. As used herein, "target" or "targets" means that the molecule binds to a complementary nucleotide sequence in a MERS-CoV gene, which is an RNA molecule, or it binds to mRNA produced by the gene. This inhibits or silences the expression of the viral gene and/or its replication. As used herein, a "conserved region" of a MERS-CoV gene is a nucleotide sequence that is found in more than one strain of the virus, is identical among the strains, rarely mutates, and is critical for viral infection and/or replication and/or release from the infected cell.

In one embodiment, the siRNA molecule is a double-stranded oligonucleotide with a length of about 17 to about 27 base pairs. In one aspect of this embodiment, the molecule is a double-stranded oligonucleotide with a length of 19 to 25 base pairs. In another aspect of this embodiment, the molecule is a couple-stranded oligonucleotide with a length of 19 to 25 base pairs. In still another aspect of this embodiment, it is a double-stranded oligonucleotide with a length of 25 base pairs. In all of these aspects, the molecule may have blunt ends at both ends, or sticky ends with overhangs at both ends (unpaired bases extending beyond the main strand), or a blunt end at one end and a sticky end at the other. In one particular aspect, it has blunt ends at both ends. In another particular aspect, the molecule has a length of 25 base pairs (25 mer) and has blunt ends at both ends.

In one embodiment, the conserved MERS-CoV genomic regions are the gene sequences coding for the MERS-CoV proteins Papain-like protease (PL$^{pro}$), RNA-dependent RNA polymerase (RdRp), and Spike protein. The genomic locations of such genes are shown in FIG. 3. In one embodiment, the siRNA molecule targets PL$^{pro}$ virus gene expression. In another embodiment, the siRNA molecule targets RdRp viral gene expression. In still another embodiment, the siRNA molecule targets Spike viral gene expression.

Particular siRNA sequences that represent some of the siRNA molecules of the invention are disclosed in Tables 1-3. In one embodiment, the siRNA molecules are disclosed in Table 3. In one particular embodiment, the siRNA molecules are the following:

| | | |
|---|---|---|
| MPL1: | CGCAAUACGUAAAGCUAAAGAUUAU, | (SEQ ID NO: 1) |
| MPL2: | GGGUGUUGAUUAUACUAAGAAGUUU, | (SEQ ID NO: 2) |
| MPL3: | CGCAUAAUGGUGGUUACAAUUCUU, | (SEQ ID NO: 3) |
| MPL4: | GGCUUCAUUUUAUUUCAAAGAAUUU, | (SEQ ID NO: 4) |
| MPL5: | GCGCUUUUACAAAUCUAGAUAAGUU, | (SEQ ID NO: 5) |
| MPL6: | CGCAUUGCAUGCCGUAAGUGUAAUU, | (SEQ ID NO: 6) |
| MRR1: | CCCAGUGUUAUUGGUGUUUAUCAUA, | (SEQ ID NO: 7) |
| MRR2: | GGGAUUUCAUGCUUAAAACAUUGUA, | (SEQ ID NO: 8) |
| MRR3: | GGGUGCUAAAUGGCAACAAGAUUGUU, | (SEQ ID NO: 9) |
| MRR4: | CCCCAAAUUUGUUGAUAAAAUACUAU, | (SEQ ID NO: 10) |
| MRR5: | CGGUUGCUUUGUAGAUGAUAUCGUU, | (SEQ ID NO: 11) |
| MSP1: | GGCCGUACAUAUUCUAACAUAACUA, | (SEQ ID NO: 12) |
| MSP2: | GGCCGUACAUAUUCUAACAUAACUA, | (SEQ ID NO: 12) |
| MSP3: | CCGAAGAUGAGAUUUUAGAGUGGUU, | (SEQ ID NO: 13) |
| MSP4: | CCCAGUUUAAUUAUAAACAGUCCUU, | (SEQ ID NO: 14) |
| MSP5: | GGCUUCACUACAACUAAUGAAGCUU, | (SEQ ID NO: 15) |
| MSP6: | CCCCUGUUAAUGGCUACUUUAUUAA, | (SEQ ID NO: 16) |

```
MSP7:  CCCUGUUAAUGGCUACUUUAUUAAA,   (SEQ ID NO: 17)
and

MSP8:  GCCGCAUAAGGUUCAUGUUCACUAA.   (SEQ ID NO: 18)
```

In one embodiment, the targeted conserved regions of the genome comprise gene sequences coding for the following MERS-CoV proteins: Papain-like protease (PL$^{pro}$), RNA-dependent RNA polymerase (RdRp), and Spike protein. In one aspect of this embodiment, the siRNA molecules target PL$^{pro}$ viral gene expression. Such siRNA molecules include the following:

```
MPL1:  CGCAAUACGUAAAGCUAAAGAUUAU,   (SEQ ID NO: 1)

MPL2:  GGGUGUUGAUUAUACUAAGAAGUUU,   (SEQ ID NO: 2)

MPL3:  CGCAUAAUGGUGGUUACAAUUCUU,    (SEQ ID NO: 3)

MPL4:  GGCUUCAUUUUAUUUCAAAGAAUUU,   (SEQ ID NO: 4)

MPL5:  GCGCUUUUACAAAUCUAGAUAAGUU,   (SEQ ID NO: 5)
and

MPL6:  CGCAUUGCAUGCCGUAAGUGUAAUU.   (SEQ ID NO: 6)
```

In another aspect of this embodiment, the siRNA molecules target RdRp viral gene expression. Such siRNA molecules include the following:

The siRNA molecules of the invention also include ones derived from those listed in Tables 1-3 and otherwise herein. The derived molecules can have less than the 25 base pairs shown for each molecule, down to 17 base pairs, so long as the "core" contiguous base pairs remain. That is, once given the specific sequences shown herein, a person skilled in the art can synthesize molecules that, in effect, "remove" one or more base pairs from either or both ends in any order, leaving the remaining contiguous base pairs, creating shorter molecules that are 24, 23, 22, 21, 20, 19, 18, or 17 base pairs in length, if starting with the 25 base pair molecule. For example, the derived molecules of the 25 mer molecules disclosed in Tables 1-3 include: a) 24 contiguous base pairs of any one or more of the molecules; b) 23 contiguous base pairs of any one or more of the molecules; c) 22 contiguous base pairs of any one or more of the molecules; b) 21 contiguous base pairs of any one or more of the molecules; d) 20 contiguous base pairs of any one or more of the molecules; e) 19 contiguous base pairs of any one or more of the molecules; f) 18 contiguous base pairs of any one or more of the molecules; and g) 17 contiguous base pairs of any one or more of the molecules. It is not expected that molecules shorter than 17 base pairs would have sufficient activity or sufficiently low off-target effects to be pharmaceutically useful; however, if any such constructs did, they would be equivalents within the scope of this invention.

Alternatively, the derived molecules can have more than the 25 base pairs shown for each molecule, so long as the initial 25 contiguous base pairs remain. That is, once given the specific sequences disclosed herein, a person skilled in the art can synthesize molecules that, in effect, "add" one or more base pairs to either or both ends in any order, creating molecules that are 26 or more base pairs in length and containing the original 25 contiguous base pairs.

The siRNA molecule may further comprise an immune stimulatory motif. Such motifs can include specific RNA sequences such as 5'-UGUGU-3' (Judge et al., Nature Biotechnology 23, 457-462 (1 Apr. 2005)), 5'-GUCCUUCAA-3' (Hornung et al., Nat. Med. 11,263-270(2005). See Kim et al., Mol Cell 24; 247-254 (2007). These articles are incorporated herein by reference in their entireties. These are siRNA sequences that specifically activate immune responses through Toll-like receptor (TLR) activation or through activation of key genes such as RIG-I or PKR. In one embodiment, the motif induces a TH1 pathway immune response. In another embodiment, the motif comprises 5'-UGUGU-3', 5'-GUCCUUCAA-3', 5'-GGGxGG-3' (where x is A, T, G and C), or CpG motifs 5'-GTCGTT-3'.

Pharmaceutical Compositions

The invention includes a pharmaceutical composition comprising an siRNA molecule that targets a conserved region of the genome of a MERS-CoV and a pharmaceutically acceptable carrier. In one embodiment, the carrier condenses the molecules to form a nanoparticle. Alternatively, the composition may be formulated into nanoparticles. The compositions may be lyophilized into a dry powder. In one particular embodiment, the pharmaceutically acceptable carrier comprises a polymeric nanoparticle or a liposomal nanoparticle.

In one embodiment, the composition comprises at least two different siRNA molecules that target one or more conserved regions of the genome of a MERS-CoV and a pharmaceutically acceptable carrier. In one aspect of this embodiment, the gene sequences in the conserved regions of the MERS-CoV are critical for the viral infection of a mammal. In one aspect of this embodiment, mammal is a human, mouse, ferret, or monkey. The composition can include one or more additional siRNA molecules that target still other conserved regions of the MERS-CoV genome. In one aspect of this embodiment, a pharmaceutically acceptable carrier comprises a polymeric nanoparticle or a liposomal nanoparticle.

```
MRR1:  CCCAGUGUUAUUGGUGUUUAUCAUA,   (SEQ ID NO: 7)

MRR2:  GGGAUUUCAUGCUUAAAACAUUGUA,   (SEQ ID NO: 8)

MRR3:  GGGUGCUAAUGGCAACAAGAUUGUU,   (SEQ ID NO: 9)

MRR4:  CCCCAAAUUUGUUGAUAAAUACUAU,   (SEQ ID NO: 10)
and

MRR5:  CGGUUGCUUUGUAGAUGAUAUCGUU.   (SEQ ID NO: 11)
```

In still another aspect of this embodiment, the siRNA molecules target Spike viral gene expression. Such siRNA molecules include the following:

```
MSP1:  GGCCGUACAUAUUCUAACAUAACUA,   (SEQ ID NO: 12)

MSP2:  GGCCGUACAUAUUCUAACAUAACUA,   (SEQ ID NO: 12)

MSP3:  CCGAAGAUGAGAUUUUAGAGUGGUU,   (SEQ ID NO: 13)

MSP4:  CCCAGUUUAAUUAUAAACAGUCCUU,   (SEQ ID NO: 14)

MSP5:  GGCUUCACUACAACUAAUGAAGCUU,   (SEQ ID NO: 15)

MSP6:  CCCCUGUUAAUGGCUACUUUAUUAA,   (SEQ ID NO: 16)

MSP7:  CCCUGUUAAUGGCUACUUUAUUAAA,   (SEQ ID NO: 17)
and

MSP8:  GCCGCAUAAGGUUCAUGUUCACUAA.   (SEQ ID NO: 18)
```

In a further aspect of this embodiment, the siRNA molecules are two or more of the following:

```
MPL1:  CGCAAUACGUAAAGCUAAAGAUUAU,   (SEQ ID NO: 1)

MPL2:  GGGUGUUGAUUAUACUAAGAAGUUU,   (SEQ ID NO: 2)

MPL3:  CGCAUAAUGGUGGUUACAAUUCUU,    (SEQ ID NO: 3)
```

```
MPL4:  GGCUUCAUUUUAUUUCAAAGAAUUU,          (SEQ ID NO: 4)

MPL5:  GCGCUUUUACAAAUCUAGAUAAGUU,          (SEQ ID NO: 5)

MPL6:  CGCAUUGCAUGCCGUAAGUGUAAUU,          (SEQ ID NO: 6)

MRR1:  CCCAGUGUUAUUGGUGUUUAUCAUA,          (SEQ ID NO: 7)

MRR2:  GGGAUUUCAUGCUUAAAACAUUGUA,          (SEQ ID NO: 8)

MRR3:  GGGUGCUAAUGGCAACAAGAUUGUU,          (SEQ ID NO: 9)

MRR4:  CCCCAAAUUUGUUGAUAAAUACUAU,          (SEQ ID NO: 10)

MRR5:  CGGUUGCUUUGUAGAUGAUAUCGUU,          (SEQ ID NO: 11)

MSP1:  GGCCGUACAUAUUCUAACAUAACUA,          (SEQ ID NO: 12)

MSP2:  GGCCGUACAUAUUCUAACAUAACUA,          (SEQ ID NO: 12)

MSP3:  CCGAAGAUGAGAUUUAGAGUGGUU,           (SEQ ID NO: 13)

MSP4:  CCCAGUUUAAUUAUAAACAGUCCUU,          (SEQ ID NO: 14)

MSP5:  GGCUUCACUACAACUAAUGAAGCUU,          (SEQ ID NO: 15)

MSP6:  CCCCUGUUAAUGGCUACUUUAUUAA,          (SEQ ID NO: 16)

MSP7:  CCCUGUUAAUGGCUACUUUAUUAAA,          (SEQ ID NO: 17)
and

MSP8:  GCCGCAUAAGGUUCAUGUUCACUAA.          (SEQ ID NO: 18)
```

In another embodiment, the composition comprises an siRNA cocktail, MST$^{PR1}$, wherein a first siRNA molecule comprises MPL1: CGCAAUACGUAAAGC-UAAAGAUUAU (SEQ ID NO: 1) and a second siRNA molecule comprises MRR1: CCCAGUGUUAUUGGU-GUUUAUCAUA (SEQ ID NO: 7).

In another embodiment, the composition comprises an siRNA cocktail, MST$^{PR2}$, wherein a first siRNA molecule comprises MPL2: GGGGUUGAUUAUAC-UAAGAAGUUU (SEQ ID NO: 19) and a second siRNA molecule comprises MRR2: GGGAUUUCAUGC-UUAAAACAUUGUA (SEQ ID NO: 8).

In another embodiment, the composition comprises an siRNA cocktail, MST$^{RS2}$, wherein a first siRNA molecule comprises MRR2: GGGAUUUCAUGCUUAAAACAUU-GUA (SEQ ID NO: 20) and a second siRNA molecule comprises MSP2: GGCCGUACAUAUUCUAA-CAUAACUA (SEQ ID NO: 12).

In another embodiment, the composition comprises an siRNA cocktail, MST$^{RS1}$, wherein a first siRNA molecule comprises MRR1: CCCAGUGUUAUUGGUGUUUAU-CAUA (SEQ ID NO: 21) and a second siRNA molecule comprises MSP1: GGCCGUACAUAUUCUAA-CAUAACUA (SEQ ID NO: 12).

In another embodiment, the composition comprises at least three different siRNA molecules that target one or more conserved regions of the genome of a MERS-CoV and a pharmaceutically acceptable carrier. In one aspect of this embodiment, the pharmaceutically acceptable carrier comprises a polymeric nanoparticle or a liposomal nanoparticle.

In another embodiment, the composition comprises an siRNA cocktail, MSTP$^{RS1}$, wherein a first siRNA molecule comprises MPL1: CGCAAUACGUAAAGC-UAAAGAUAU (SEQ ID NO: 22), a second siRNA molecule comprises MRR1: CCCAGUGUUAUUGGU-GUUUAUCAUA (SEQ ID NO: 7), and a third siRNA molecule comprises MSP1: GGCCGUACAUAUUCUAA-CAUAACUA (SEQ ID NO: 12).

In another embodiment, the composition comprises an siRNA cocktail, MST$^{PRS2}$, wherein a first siRNA molecule comprises MPL2: GGGUGUUGAUUAUAC-UAAGAAGUUU (SEQ ID NO: 2) a second siRNA molecule comprises MRR2: GGGAUUUCAUGCUUAAAA-CAUUGUA (SEQ ID NO: 8), and a third siRNA molecule comprises MSP2: GGCCGUACAUAUUCUAA-CAUAACUA (SEQ ID NO: 12).

In one aspect of all of these embodiments, the siRNA molecules comprise 25 mer blunt-end siRNA molecules and the carrier comprises a Histidine-Lysine copolymer or Spermine-Lipid Conjugate and cholesterol.

Pharmaceutically Acceptable Carriers

Pharmaceutically acceptable carriers include saline, sugars, polypeptides, polymers, lipids, creams, gels, micelle materials, and metal nanoparticles. In one embodiment, the carrier comprises at least one of the following: a glucose solution, a polycationic binding agent, a cationic lipid, a cationic micelle, a cationic polypeptide, a hydrophilic polymer grafted polymer, a non-natural cationic polymer, a cationic polyacetal, a hydrophilic polymer grafted polyacetal, a ligand functionalized cationic polymer, a ligand functionalized-hydrophilic polymer grafted polymer, and a ligand functionalized liposome. In another embodiment, the polymers comprise a biodegradable histidine-lysine polymer, a biodegradable polyester, such as poly(lactic acid) (PLA), poly(glycolic acid) (PGA), and poly(lactic-co-glycolic acid) (PLGA), a polyamidoamine (PAMAM) dendrimer, a cationic lipid, or a PEGylated PEI. Cationic lipids include DOTAP, DOPE, DC-Chol/DOPE, DOTMA, and DOTMA/DOPE. In still another embodiment, the carrier is a histidine-lysine copolymer that forms a nanoparticle with the siRNA molecule, wherein the diameter of the nanoparticle is about 100 nm to about 400 nm.

In one embodiment, the carrier is a polymer. In one aspect of this embodiment, the polymer comprises a histidine-lysine copolymer (HKP). Such copolymers are described in U.S. Pat. Nos. 7,070,807 B2, 7,163,695 B2, and 7,772,201 B2, which are incorporated herein by reference in their entireties. In one aspect of this embodiment, the HKP comprises the structure (R)K(R)-K(R)-(R)K(X), where R=KHHHKHHHKHHHKHHHK (SEQ ID NO: 23), K=lysine, and H=histidine.

In another embodiment, the carrier is a liposome. In one aspect of this embodiment, the liposome comprises a cationic lipid conjugated with cholesterol. In a further aspect, the cationic lipid comprises a spermine head and one or two oleyl alcoholic tails. Examples of such molecules are disclosed in FIG. 8. In a further aspect, the liposome comprises Spermine-Liposome-Cholesterol conjugate (SLiC).

Methods of Use

The invention also includes methods of using the siRNA molecules and pharmaceutical compositions containing them to prevent or treat MERS-CoV disease. A therapeutically effective amount of the composition of the invention is administered to a subject. In one embodiment, the subject is a mammal such as a mouse, ferret, monkey, or human. In one aspect of this embodiment, the mammal is a laboratory animal, such as a rodent. In another aspect of this embodiment, the mammal is a non-human primate, such as a monkey. In still another aspect of this embodiment, the mammal is a human. As used herein, a "therapeutically effective amount" is an amount that prevents, reduces the severity of, or cures MERS disease. Such amounts are determinable by persons skilled in the art, given the teachings contained herein. In one embodiment, a therapeutically effective amount of the pharmaceutical composition administered to a human comprises about 1 mg of the siRNA molecules per kilogram of body weight of the human to about 5 mg of the siRNA molecules per kilogram of body weight of the human. Routes of administration are also determinable by persons skilled in the art, given the teachings contained herein. Such routes include intranasal administration and airway instillation, such as through use of an airway nebulizer. Such routes also include intraperitoneal, intravenous, and subcutaneous administration.

EXAMPLES

We selected Papain-like protease (PL$^{PRO}$), RNA-dependent RNA polymerase (RdRp), Spike(S) protein and some of other structure genes (such as M and N protein) and non-structure genes (such as nsp-2, nsp-10 and nsp-15) of MERS-CoV as the targets for an siRNA cocktail-mediated therapeutic approach. The present invention provides siRNA molecules that target a conserved region of MERS-CoV, wherein the siRNA molecules inhibit expression of those genes of MERS-CoV. In a preferred embodiment, the molecule comprises a double-stranded sequence of 17, 18, 19, 20, 21, 22, 23, 24 or 25 nucleotides in length. In one aspect of this embodiment, the siRNA molecule has blunt ends, or has 3' overhangs of one or more nucleotides on both sides of the double-stranded region. The siRNA cocktail of the invention contains two, three, four, or more sequences targeting those genes of MERS-CoV.

Example 1

MERS-CoV Viral Structure and Protein Function

MERS-CoV is enveloped single-stranded positive sense RNA viruses with genomes of 30,119 nt. The genome structure of MERS-CoV is similar to other coronaviruses, with the 5' two-thirds of the genome encoding the nonstructural proteins (NSPs) required for viral genome replication, the remaining 3' third of the genome encoding the structural genes that make up the virion (spike, envelope, membrane, and nucleocapsid proteins), and four accessory genes interspersed within the structural gene region (FIG. 1A). At the 5' end of the genome there is a leader sequence (67nt), which is followed by an untranslated region (UTR). At the 3' end of the RNA genome there is another UTR, followed by a poly(A) sequence of variable length. Transcription-regulatory sequences (TRS 5' AACGAA 3') are found at the 3' end of the leader sequence and at different positions upstream of genes in the genomic 3'-proximal domain of MERS-CoV. The MERS-CoV genome contains at least 10 predicted open reading frames (ORFs): ORF1a, ORF1b, S, 3, 4a, 4b, 5, E, M and N with sixteen predicted nonstructural proteins being encoded by ORF1a/b. Several unique group-specific ORFs that are not essential for virus replication are encoded by MERS-CoV. The functions of these group-specific ORFs are unknown; however, by analogy to other coronaviruses, they may encode structural proteins or interferon antagonist genes. Open reading frames ORF2, -6, -7 and-8a are translated from subgenomic mRNAs predicted to encode the four canonical structural genes: a 180/90-kDa spike glycoprotein (S), a~23-kDa membrane glycoprotein(M), a small envelope protein (E) and a~50-kDa nucleocapsidprotein (N), respectively (FIG. 1B-C).

Example 2

MERS-CoV Viral Genes and RNAs

Similar to other RNA viruses, coronavirus replicate in the host cytoplasm. The replication process is initiated by the viral particle after binding with specific cellular receptors, known as S-protein mediated binding. The receptor for MERS-CoV was recently identified as dipeptidyl peptidase 4 (DDP4, also known as CD26), a protein with diverse functions in glucose homeostasis, T-cell activation, neurotransmitter function, and modulation of cardiac signaling. DPP4 is expressed in a variety of cell types, including endothelial cells (kidney, lung, small intestine, spleen) hepatocytes, enterocytes, activated leukocytes, testes, prostate and cells of the renal glomeruli and proximal tubules. DPP4 recognition is mediated by the receptor-binding domain (RBD, amino acids E367-Y606). Following virus entry, the coronavirus genome, a positive sense, capped and polyadenylated RNA strand, is directly translated, resulting in the synthesis of coronavirus replicase gene-encoded NSPs. Coronavirus NSPs are translated as two large polyproteins harboring proteolytic enzymes, namely papain-like and chymotrypsin-like proteinases that extensively process coronavirus polyproteins to liberate up to 16 NSPs (nsp 1-16). After entering into the cell the virus specially modulates the innate immune response, antigen presentation, mitogen-activated protein kinase (FIG. 2).

Example 3

Design siRNA Targeting Key Genes of MERS-CoV

Using our specific algorithm, we have designed multiple siRNA sequences, including both 25-mer and 23-mer oligos. Table I. siRNA sequences, 25-mer blunt-end oligos and 23-mer sticky-end oligos, targeting various viral RNA Table II. siRNA sequences, 25-mer blunt-end oligos and 23-mer sticky-end oligos, targeting various viral RNA Table III. We selected the most potent siRNA oligos, 25-mer blunt-end oligos and 23-mer sticky-end oligos, targeting various viral proteins and genes. As demonstrated in the FIG. 3, we are specifically targeting critical viral genes: Papain like protein (PL$^{pro}$) specific siRNA, total 6 active siRNAs (MPL1-6); RNA dependent RNA protease (RDRP) specific siRNA, total 5 active siRNAs (MRR1-5) and Spike protein specific siRNA, total 8 active siRNAs (MSP1-8).

Example 4

Cell Culture Based Screening for Potent Anti-MERS CoV siRNA Oligos

Firstly, to identify the most potent siRNA for silencing MERS-CoV genes in Vero cell culture experiments, we used psiCheck plasmid carrying MERS-CoV gene sequences.
Secondly, we used Vero cell infected with real MERS-CoV to test the selected siRNA for their anti-MERS CoV infecting activity.
A. Subcloning MERS-CoV virus gene fragments as surrogates for siRNA potency examination in Vero cells In order to investigate the degrading effect of siRNA candidates on targeted MERS-CoV genes, we used a dual luciferase reporter vector, psiCHECK-2, with gene fragments of Papain like viral protein (nsp5), Conoravirus endopeptidase C30 (nsp6), RNA synthesis protein (nsp10), RNA-dependent RNA polymerase (nsp12), and structure proteins S, E, M and N. psiCHECK-2 Vectors are designed to provide a quantitative and rapid approach for initial optimization of RNA interference (RNAi). The vectors enable monitoring of changes in expression of a target gene fused to a reporter gene. The DNA fragments of nsp5, nsp6, nsp10, nsp12 and structure proteins S, E, M and N were amplified by PCR with specific primers to those genes, and then cloned into the multiple cloning sites of psiCHECK-2 Vector. In this vector, *Renilla* Luciferase is used as a primary reporter gene, and the siRNA targeting genes located downstream of the *Renilla* translational stop codon.

Vero cells were seeded in 96-well plates and incubated for 12 h. The reporter plasmids (recombinant vectors) psi-nsp5, psi-nsp6, psi-nsp10, psi-nsp12, psi-S, psi-E, psi-M and psi-N, and siRNA candidates were co-transfected into Vero cells using Lipofectamine 2000 in the DMEM without FBS. The blank psi vector is taken as a negative control. Six hours post-transfection, the media was replaced with the DMEM supplemented with 10% FBS. 18, 24, 36 and 48 h post-transfection the activity of the firefly luminescence and *Renilla* Luciferase in each well was detected using the Dual Luciferase Kit. The siRNA candidates dramatically decreased luciferase activity which indicates that siRNA could greatly inhibit the expression of the target genes of MERS-CoV were selected for the assay of infection with MERS-CoV in vitro.

B. Infection of Vero cells with MERS-CoV To investigate whether the real MERS-CoV mRNAs for nsp5, nsp6, nsp10, nsp12 and structure proteins S, E, M and N can be directly degraded by the specific mechanism of RNA interference (RNAi), Vero cells were seeded in 24-well plate and transfected with selected therapeutic single siRNA or siRNA combination candidates using Lipofectamine 2000 in the DMEM without FBS when cell monolayer reached 80% confluency. The transfection efficacy control is Cy3 labeled siRNA. PBS was taken as a negative control. An siRNA with the sequence unrelated to MERS-CoV was used as another negative control. 24 h post-transfection the media containing the transfection reagent was replaced with fresh media supplemented with 2% FBS, and cells were infected with MERS-CoV. One hour post-infection, the inoculation solution was replaced with DMEM supplemented with 10% FBS. 24 h post-infection, cells were harvested for RNA isolation and 5'-rapid amplification of cDNA ends (5'-RACE). In the other parallel experiment, at 24, 48 and 72 h post-infection, the cell supernatants were harvested for viral titer determination. All experiments were performed under Biosafety level-2 condition.

The viral RNA were extracted from the cell supernatants, and the one-step quantitative real-time PCR were performed with forward, reverse primers and TaqMan probe specific to the MERS-CoV isolate FRA/UAE spike protein. The total RNA from the harvested cells was extracted, and 5'-RACE assays were carried out with gene-specific primers for cDNA products of nsp5, nsp6, nsp10, nsp12 and structure proteins S, E, M and N. The single siRNAs or siRNA combinations with high protection efficiency were selected for in vivo studies.

Example 5

HKP/siRNA nanoparticle and pulmonary delivery

Histidine-Lysine co-polymer (HKP) siRNA nanoparticle formulations can be established by mixing together aqueous solutions of HKP and siRNA in 4:1 ratio by a molecular weight (N/P). A typical HKP/siRNA formulation will provide nanoparticles in average size in 150 nm in diameter (FIG. 4A). The self-assembled HKP/siRNA nanoparticles can be resuspended in aqueous solution, lyophilized into dry powder, and then resuspended in RNase free water (FIG. 4B). After oral-trachial administration of HKP/siRNA ( ) nanoparticles to the mouse respiratory track we were able to observe fluorescent siRNA in the upper (bronchi), and lower airway (alveoli) (FIG. 4C). We compared the efficacy of RNAi of cyclophiline B in the lung after oraltrachial deliveries of three different doses of siRNA with HKP, DOTAP and D5W. HKP-mediated delivery demonstrated the efficient RNAi of the target gene at the 20 µg dose (FIG. 5).

Example 6

HKP/siRNA Formulation for Intraperitoneal Delivery

During evaluation of prophylaxis and therapeutic benefit of siRNA inhibitors against influenza infection, we tested HKP/siRNA formulation through intraperitoneal administration, using different dosage and regimens. Based on the observations of these treatment results, we found that the prophylactic effect of HKP/siRNA (two siRNAs arespecific to influenza genes) exceed the effect of Ribovirin (FIG. 6). Similarly, the therapeutic effect of HKP/siRNA (two siRNAs are specific to influenza genes) is greater than Tamiflu® effect (FIG. 7). Due to the fact that both influenza and MERS infections occur in the human respiratory system, we are envisioning that the similar therapeutic approach, such as the HKP/siRNA therapeutics, can be applied for treatment of MERS since we observed the positive therapeutic benefit.

Example 7

SLiC/siRNA Nanoparticle

SLiC Liposome Preparation. Regular methods were tried at first to prepare liposomes with newly synthesized SLiC molecules, such as thin film method, solvent injection and so on without much success. Norbert Maurer et al reported a method of liposome preparation in which siRNA or oligonucleotide solution was slowly added under vortexing to the 50% ethanol solution (v/v) of liposome and ethanol was later removed by dialysis. The nanoparticles thus derived were small in size and homogeneous. In this method, siRNA was directly wrapped by cationic lipids during formation of liposome, while in most other methods siRNA or nucleic acid molecules are loaded (or entrapped) into preformed liposome, such as Lipofectamine 2000.

Lipids dissolved in ethanol are in so-called metastable state in which liposomes are not very stable and tend to aggregate. We then prepared un-loaded or pre-formed liposomes using modified Norbert Maurer's method. We found that stable liposome solution could be made by simply diluting ethanol to the final concentration of 12.5% (v/v). Liposomes were prepared by addition of lipids (cationic SLiC/cholesterol, 50:50, mol %) dissolved in ethanol to sterile dd-H$_2$O. The ethanolic lipid solution needs to be added slowly under rapid mixing.

Slow addition of ethanol and rapid mixing were critical for the success in making SLiC liposomes, as the process allows formation of small and more homogeneous liposomes. Unlike conventional methods, in which siRNAs are loaded during the process of liposome formulation and ethanol or other solvent is removed at end of manufacturing, our SLiC liposomes were formulated with remaining ethanol still in the solution so that liposomes were thought to be still in metastable state. When siRNA solution was mixed/loaded with liposome solution cationic groups, lipids will interact with anionic siRNA and condense to form core. SLiC liposomes' metastable state helped or facilitated liposome structure transformation to entrap siRNA or nucleic acids more effectively. Because of the entrapment of siRNA, SLiC liposomes become more compact and homogeneous.

Physiochemical Characterization of SLiC Liposome. After the liposome formation, we have developed an array of assays to characterize the physicochemical properties of SLiC liposome, including particle size, surface potential, morphology study, siRNA loading efficiency and biological activity, etc. The particle size and zeta-potentials of SLiC liposomes were measured with Nano ZS Zeta Sizer (Malvern Instruments, UK). Each new SLiC liposome was tested for particle size and zeta-potential when ethanol contents changed from 50% to 25% and to 12.5%. Data were derived from formulations of different ethanol contents. All SLiC liposomes were prepared at 1 mg/ml in concentration and loaded with siRNA (2:1, w/w). Each of SLiC Liposomes was composed of cationic SLiC and cholesterol dissolved in ethanol at 12.5%, e.g. TM2 (12.5). The average particle sizes of three sequential measurements and the average zeta-potentials of three sequential measurements were illustrated in Table IV.

Further analysis of the physiochemical perimeters of the SLiC liposome suggested that ethanol concentrations were positively proportional to particle sizes (the lower of ethanol concentration, the smaller of particle sizes), but negatively proportional to zeta-potential (the lower of ethanol concentration, the higher of zeta-potential at the same time). The higher surface potential will render particles more stable in solution. In addition to stability in solution, data shown later also indicated that toxicity was lower with lower ethanol concentration, too. Therefore, to put all factors together, ethanol concentration of 12.5% (v/v) was selected as solvent to suspend cholesterol as well as SLiC into the master working stock solution before they were used to make liposome formulations.

In contrast to bare SLiC liposome formulation, liposomes particle sizes became much smaller when they were loaded with siRNA at 2:1 (w/w) resulting in particle sizes in the range of 110 to 190 nm in diameter and much lower PDI values. Conventional consideration of liposomal structure dictates that siRNA is loaded or interacted with cationic lipids through electrostatic forces and liposomes wraps siRNA to form spherical particles in shape in order to reduce surface tension. As the result, the liposomes particle sizes became much smaller after loaded with siRNA. Liposomes formulated with siRNA also have lower surface charge, which could be explained by neutralizing effect from loaded siRNA.

Example 8

Airway Delivery with Mouse Model

Human host-cell dipeptidyl peptidase 4 (hDPP4) has been shown to be the receptor of MERS-CoV. However, mouse is not a suitable small-animal model for MERS-CoV as it has no receptor being recognized and bound by the virus. In this study, the mice were sensitized to MERS-CoV infection by transduction with Adenoviral or Lentiviral vector expressing hDPP4 in the respiratory tract. This mouse model was used to investigate the efficiency of the siRNA on inhibiting the MERS-CoV infection in vivo. The siRNA combination candidate was delivered by encapsidated with HKP-SLiC nanoparticle system. We performed all mouse studies under Biosafety level-3 conditions.

All BALB/c mice were 18 weeks old and tested as specific pathogen-free at the beginning of this study. To develop the susceptibility to MERS-CoV, 30 mice of Adenoviral vector group and 30 mice of Lentiviral vector group were transduced with Adenoviral and Lentiviral vector expressing hDPP4, respectively. Another 20 mice were transduced with empty Adenoviral or Lentiviral vector as the control. For the Adenoviral vector group, hDDP4 gene was cloned into the Ad5. Then MLE 15 cells were transduced with Ad5-hDDP4 at an MOI of 20. The supernatant were collected at 48 h post-infection. The mice were transduced intranasally with $10^8$ pfu of Ad5-hDDP4. For the Lentiviral vector group, hDDP4 gene was cloned into the plasmid pWPXLd. Then, pWPXLd-hDPP4, along with packaging vector, psPAX2, and envelope vector, pMD2.G, was co-transfected into packaging cell line HEK 293T using calcium phosphate method. At 48 h post-transfection, the constructed viral vector was harvested and purified, and transducted with CHO cells. The lentivirus was harvested and concentrated. The mice were transduced intranasally with lentivirus expressing hDPP4 at titers of $10^8$ transducing units/ml (TU/ml).

After confirming the hDPP4 was expressed in the respiratory tract of the mice by western blot, the Adenoviral and Lentiviral vector groups were further divided into prophylactic, therapeutic and control subgroup with ten mice in each subgroup. Ten mice from Ad5-hDDP4 or psPAX2-hDDP4 prophylactic subgroup were intranasally inoculated with siRNA combination encapsidated with HKP-SLiC nanoparticle system 24 h before inoculation. 24 h later, all eighty mice including transduced with empty vector were infected intravenously with $10^5$ pfu of MERS-CoV. The prophylactic, therapeutic and control subgroup were intranasally inoculated with siRNA or PBS at 0, 24, 48, 72 and 96 h post-infection.

All mice were weighed and the survivors of each subgroup were counted daily. The nasal washes were collected at 1, 3, 5, 7, 9, and 14 day post-infection for the viral titration. Two infected mice from each group were sacrificed at 3 and 5 day post-infection, respectively. The tissue collection, including lung, trachea, spleen, liver, heart, brain and kidney, were collected for pathological and virological study.

To determine the viral titers, the tissue samples were homogenized in DMEM, and clarified by centrifugation. Both tissue suspensions and nasal washes were 10-fold serially diluted. The dilutions were added to the Vero cells monolayers grown in 96-well plates. The cytopathic effects (CPEs) were observed on day 3 post-infection, and the $TCID_{50}$ was calculated by the Reed-Muench method.

To investigate the efficiency of siRNA candidates in inhibiting viral gene expression, the total RNAs were extracted from the tissues and the one-step quantitative real-time PCR were performed with forward, reverse primers and TaqMan probe specific to the conserved region of nsp12 (RNA-dependent RNA polymerase) of MERS-CoV.

Example 9

Intraperitoneal siRNA Nanoparticle Solution

In vivo administration of siRNAs. The in vivo experiments were conducted using 6-8 week old female mice. For inoculation, allantoic fluid containing the virus at a dose of $5 \times 10^4$ $EID_{50}$/mL was used. The infectious activity of the virus in allantoic fluid was determined in vivo by titration of lethality. Titers of the virus were calculated using the Reed and Muench method. Non-infected mice that were kept in the same conditions as the infected animals were used as a negative control. Virus was administered to the animals intranasally under a light ether anesthesia. Each group of animals contained 15 mice. siRNA (1:1 ratio of siRNAs 89 and 103) complexed with PAA as described above, was administered to the animals at the dose of 1-10 mg/kg of body weight. siRNA was administered intraperitoneally (200 ul per injection). Control animals received PAA without siRNAs.

Animals were observed for 14 days post inoculation. The mortality of the animals in control and experimental groups was registered daily. The mortality percentage (M) was calculated in each group as: M=N/Nt where: N—the number of animals died within 14 days after infection; Nt—the total number of animals in the group. The index of protection (IP) was calculated as: IP=((Mc−Me)/Mc)×100%, where: Mc and Me—percentage of mortality in control and experimental groups, correspondingly. The median day of death (MDD) within 14 days was calculated as: MDD=(Σ N D)/Nt, where: N—the number of animals surviving D days; Nt—total number of animals in the group Tamiflu® (oseltamivir phosphate, Roche, Switzerland) was used as a reference compound. It was administered at a dose of 25 mg/kg by the same protocol.

The intraperitoneal administration could be a viable alternative, especially in patients with severe influenza with low gas-exchange volume and/or those on mechanical lung ventilation. Since siRNAs of the same length show similar properties (charge, hydrophobicity, molecular weight etc) and since siRNAs can be rapidly designed and manufactured, it is feasible that nanoparticle-mediated siRNA delivery may form an intermediate therapeutic strategy in treating rapidly emerging influenza virus strains with high mortality rates that do not respond to existing therapies, while vaccines to protect the general population are under development. The siRNA cocktail demonstrated herein may provide significant value as a prophylactic/therapeutic with broad anti-influenza strain coverage and this coverage may well extend to as yet unidentified Influenza strains that may emerge in the future. As stated in the Example 6, the therapeutic benefit we observed during the study using siRNA approach against influenza viral infection has provided a good example to follow: the HKP/siRNA nanoparticle delivery through IP route or respiratory route, targeting the conservative regions of the critical viral gene sequences, and siRNA cocktail design, etc.

We demonstrated in this study that polymeric nanoparticle-mediated delivery of a combination of two siRNAs, via IP administration, can result in a potent antiviral effect in the viral-challenged animals. Histidine Lysine Co-Polymer (HKP) nanoparticle-mediated siRNA delivery has been well validated through multiple routes with various animal models (17). We recently completed a full scale safety study for HKP-siRNA nanoparticle formulation via subcutaneous administration into both mouse and monkey models (data not shown). When HKP-siRNA103/105 formulation was IP administrated (10 mg/kg/day), a prophylactic and therapeutic benefit greater than that observed with Ribavirin (75 mg/kg/day) in protecting mice from exposure to a 2× LD50 dose of the virus. (Ribavirin is manufactured by multiple companies in the United States: Copegus produced by Genentech (member of the Roche group), Rebetol by Merck Sharp & Dome, a subsidary of Merck & Co., Inc., and Ribasphere by Kadmon Pharmaceuticals (orginaily by Three Rivers Pharmaceuticals which was acquired by Kadmon Pharmaceuticals). In addition, several companies, including Sandoz and Teva pharmaceuticals, produce generic ribavirin.) The data obtained suggests that IP injection of peptide nanoparticles containing siRNAs or of a polycationic delivery vehicle carrying siRNAs can both ameliorate the lethality induced by Influenza infection in mice and therefore may suggests the ability to overcome some of these barriers. The amphiphilic poly(allylamine) (PAA) formed polymeric micelles (PM) has been evaluated for siRNA delivery via the GI tract, resulting in efficient siRNA delivery and endosome/lysosome release. PAA and siRNA can be self-assembled into complexes with nano-sized diameters (150-300 nm) and cationic surface charge (+20 to 30 mV). When we IP administered PAA-siRNA89/103 formulation (10 mg/kg) a therapeutic antiviral activity was observed equivalent to that of Tamiflu (25 mg/kg). These results clearly demonstrated that polymeric nanoparticle delivery of siRNA combinations may provide a prophylactic/therapeutic response against newly emergent strains of influenza virus. A similar approach can be considered for a MERS siRNA therapy.

Example 10

Effects on Innate Immunity in Lung

To evaluate the cytokine response after HKP/siRNA formulation administration to the mouse airway, we collected the lung lavage samples from the Balb/c mice treated with intratracheal instillation of HKP/siRNA aqueous solution (the cohort and dosage described in Table A). The lavage samples were further measured for the TNF-α, IL-6 and IFN-α changes before and after the treatment using commercial available ELISA assay (FIG. 10). We first established a standard curve (using Lowry method) of the protein concentration and then measured the protein concentrations of each collected sample, where the STP705 stands for HKP/siRNA groups with different siRNA concentrations (FIG. 11). Based on the standard curves for TNF-α, IL-6 and IFN-α we established using the commercial kits (FIG. 12A, FIG. 13A and FIG. 14A), we measured the TNF-α, IL-6 and IFN-α cytokine levels of each collected samples (FIG. 12B, FIG. 13B and FIG. 14B). With comparisons between the normal mouse lungs and LPS treated mouse lungs, and HKP/siRNA treated lungs, we found that (1) HKP/siRNA treatment has little impact on the lung TNF-α level changes (FIG. 12B); (2) Various HKP/siRNA formulations with different siRNA concentrations can induce IL-6 level elevation (FIG. 13B); (3) There is no significant changes of the IFN-α levels with the HKP/siRNA formulation treatments.

TABLE A

Effect of siRNA-HKP nanoparticles on innate immunity at lung
Experiment design

| Group | Animal# | composition |
|---|---|---|
| 1, Normal | 5 | — |
| 2, Blank | 5 | 0.9% NS |
| 3, HKP | 5 | 160 μg HKP |
| 4, siRNA | 5 | 40 μg siRNA①+② |
| 5, HKP/siRNA high | 5 | 160 μg HKP + 40 μg siRNA |
| 6, HKP/siRNA low | 5 | 80 μg HKP + 20 μg siRNA |
| 7, HKP/siRNA | 5 | 20 μg STP705 |
| 8, LPS | 5 | 5 mg/kg |

Example 11

Non-Human Primate Study

Currently, there is neither an effective vaccine nor drug available for prophylatic or therapeutic strategy. Recently, rhesus macaque has been developed as a model for MERS-CoV using intratracheal inoculation. Similar to human, the infected monkeys showed clinical signs of disease, virus replication, and histological lesions, indicating that rhesus macaque is a good model for evaluation of vaccine and antiviral strategies against MERS-CoV infection.

To investigate the efficiency of the siRNA on protecting and healing from MERS-CoV infection, we plan to perform the non-human primate study in rhesus macaques. The siRNA cocktail candidate will be encapsidated with HKP-SLiC nanoparticle system, and administered intratracheally. This monkey study should be carried out under Biosafety Level-3 condition.

All rhesus monkeys should be 2-3 years old at the beginning of this study. At the beginning, all monkeys need to be tested negative for MERS-CoV. Twelve monkeys should be divided into three groups—prophylactic, protection, and control group with four animals in each group. Four monkeys of prophylactic group should be intratracheally inoculated with siRNA combination encapsidated in HKP-SLiC nanoparticle system using a nebulizer. 24 h later, all twelve monkeys should be intratracheally inoculated with $6.5 \times 10^7$ $TCID_{50}$ of MERS-CoV in 1 mL. The prophylactic and protection groups should be continuously inoculated with siRNA combination at 0, 24, 48, 72 and 96 h post-infection using the nebulizer. The control group will be inoculated with PBS at the same time points.

All monkeys will be observed twice daily for the symptoms and mortality. Chest X-rays need to be performed 1 day pre-infection and 3, and 5 day post-infection. Oropharyngeal, nasal, and cloacal swabs should be collected at 1, 3, 5, 7, 9, 14, 21, and 28 day post-infection for the viral titration. Two infected monkeys from each group will be sacrificed on the day 3 post-infection. The tissue including lung, trachea, spleen, liver, heart, brain, kidney, and colon tissue will be collected for pathological and virological study.

The viral titers determination in the tissue and swab samples should be performed as described in Example 2. To investigate the efficiency of siRNA candidates on inhibiting viral gene expression, the total RNA will be extracted from the tissues and the one-step quantitative real-time PCR were performed.

To investigate the efficiency of siRNA candidates on inhibiting viral protein expression, the total RNA will be extracted from the tissues and the one-step quantitative real-time PCR will be performed as described in Example 8.

REFERENCES

1. Zumbla A, et al. (2015) Middle East respiratory syndrome. Lancet S0140-6736(15)60454-8.
2. Jalal S. (2015) The emerging threat of MERS. Pak Med Assoc. 65(3):310-1.
3. de Wit E, et al. (2013) Middle East respiratory syndrome coronavirus (MERS-CoV) causes transient lower respiratory tract infection in rhesus macaques. Proc Natl Acad Sci USA 110:16598-16603.
4. Chan J F (2015) Middle East Respiratory Syndrome Coronavirus: Another Zoonotic Betacoronavirus Causing SARS-Like Disease Clin. Microbiol. 28(2): 465-522.
5. Totura A L, Baric R S (2012) SARS coronavirus pathogenesis:Host innate immune responses and viral antagonism of interferon. Curr Opin Virol 2:264-275.
6. Abdel-Moneim A S (2014) Middle East respiratory syndrome coronavirus (MERS-CoV): evidence and speculations. Arch Virol. 159(7):1575-84.
7. Pascal K, et al. (2015) Pre- and postexposure efficacy of fully human antibodies against Spike protein in a novel humanized mouse model of MERS-CoV infection. Proc Natl Acad Sci USA. pii: 201510830.
8. de Wilde A H et al. (2014) Screening of an FDA-approved compound library identifies four small-molecule inhibitors of Middle East respiratory syndrome coronavirus replication in cell culture. Chemother. 58(8):4875-84. doi: 10.1128/AAC.03011-14.
9. Falzarano D, et al., (2013) Treatment with interferon-α2b and ribavirin improves outcome in MERS-CoV-infected rhesus macaques. Nat Med 19(10):1313-1317.
10. Lu L. et al.(2015) Urgent development of effective therapeutic and prophylactic agents to control the emerging threat of Middle East respiratory Syndrome (MERS). Emerging Microbes & Infections (2015) 4, e37; doi: 10.1038/emi.2015.37.
11. Zhao J, et al (2015) Passive immunotherapy with dromedary immune serum in an experimental animal model for middle East respiratory syndrome coronavirus infection. Virol. 89(11):6117-20. doi: 10.1128/JVI.00446-15.
12. Tianlei Ying et al (2015) Development of human neutralizing monoclonal antibodies for prevention and therapy of MERS-CoV infections. Microbes and Infection 17 (2015) 142-148.
13. Needle D. et al. (2015) Structures of the Middle East respiratory syndrome coronavirus 3C-like protease reveal insights into substrate specificity Acta Cryst. (2015). D71, 1102-1111.
14. Chan et al. (2013) Differential cell line susceptibility to the emerging novel humanbetacoronavirus 2c EMC/2012: implications for disease pathogenesisand clinical manifestation. J Infect Dis 207:1743-1752
15. Lundin A et al.(2014) Targeting membrane-bound viral RNA synthesis reveals potent inhibition of diverse coronaviruses including the middle East respiratory syndrome virus. PLoS Pathogens, vol. 10, no. 5, Article ID e1004166, 2014.
16. Zhao J, et al. (2014) Rapid generation of a mouse model for Middle East respiratory syndrome. Proc Natl Acad Sci USA 111(13):4970-4975.
17. Leng, Q and Mixson J. et al. Systemic delivery of HK Raf-1siRNA Polyplexes Inhibits MDA-MB-435 Xenografts. *Cancer Gene Therapy.* 1-11(2008).

The disclosures of all publications identified herein, including issued patents and published patent applications, and all database entries identified herein by url addresses or accession numbers are incorporated herein by reference in their entirety.

Although this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

TABLE 1

Predicted 25 mer siRNA targeting
MERS NC019843.3
25mer blunt ended sequences

| SiRNA sequence | SEQ ID NO: | StartProtein Base Coded | | 23 mer Sequences passing all metrics and BLAST search (allows for 2 base overhang on 21mer) | SEQ ID NO: |
|---|---|---|---|---|---|
| GGCUCAUUGCUUGUGAAAAUCCAUU | 24 | 1timesat | 555 NSP1 | | |
| GCUUGUGAAAAUCCAUUCAUGGUUA | 25 | 1timesat | 563 NSP1 | | |
| CCAUUCAUGGUUAACCAAUUGGCUU | 26 | 1timesat | 575 NSP1 | | |
| CGAACUUGUCACAGGAAAGCAAAAU | 27 | 1timesat | 679 NSP1 | | |
| GCAAAAUAUUCUCCUGCGCAAGUAU | 28 | 1timesat | 697 NSP1 | | |
| CCCCAUUCCACUAUGAGCGAGACAA | 29 | 1timesat | 744 NSP1 | | |
| GGCAAAUAUGCCCAGAAUCUGCUUA | 30 | 1timesat | 815 NSP1 | | |
| GCAAAUAUGCCCAGAAUCUGCUUAA | 31 | 1timesat | 816 NSP1 | | |
| CCCAGAAUCUGCUUAAGAAGUUGAU | 32 | 1timesat | 825 NSP1 | CCCAGAAUCUGCUUAAGAAGUUG | 952 |
| CCAGAAUCUGCUUAAGAAGUUGAUU | 33 | 1timesat | 826 NSP1 | | |
| GCUUAAGAAGUUGAUUGGCGGUGAU | 34 | 1timesat | 835 NSP1 | | |
| CGGUGAUGUCACUCCAGUUGACCAA | 35 | 1timesat | 853 NSP1 | | |
| GGUGAUGUCACUCCAGUUGACCAAU | 36 | 1timesat | 854 NSP1 | | |
| GGAAAACCCAUUAGUGCCUACGCAU | 37 | 1timesat | 896 NSP2 | | |
| CCCAUUAGUGCCUACGCAUUUUUAA | 38 | 1timesat | 902 NSP2 | | |
| CCAUUAGUGCCUACGCAUUUUUAAU | 39 | 1timesat | 903 NSP2 | | |
| GGAUGGAAUAACCAAACUGGCUGAU | 40 | 1timesat | 934 NSP2 | | |
| CGU-CGCAGCACGUGCUGAUGACGAA | 41 | 1timesat | 970 NSP2 | | |
| GCUGAUGACGAAGGCUUCAUCACAU | 42 | 1timesat | 983 NSP2 | | |
| CGUUCCAUAUCCUAAGCAAUCUAUU | 43 | 1timesat | 1054 NSP2 | | |
| CCAUAUCCUAAGCAAUCUAUUUUUA | 44 | 1timesat | 1058 NSP2 | | |
| CCUAAGCAAUCUAUUUUUACUAUUA | 45 | 1timesat | 1064 NSP2 | | |
| CCUCCUCACUAUUUUACUCUUGGAU | 46 | 1timesat | 1124 NSP2 | | |
| CGUUUCUGACUUGUCCCUCAAACAA | 47 | 1timesat | 1189 NSP2 | | |
| GGUAAGGAGUCACUUGAGAACCCAA | 48 | 1timesat | 1235 NSP2 | | |
| CCAACCUACAUUUACCACUCCGCAU | 49 | 1timesat | 1256 NSP2 | | |
| CCUACAUUUACCACUCCGCAUUCAU | 50 | 1timesat | 1260 NSP2 | | |
| GCUAUCCAAGGGUUUGCCUGUGGAU | 51 | 1timesat | 1328 NSP2 | | |
| GGGUUUGCCUGUGGAUGUGGGGCAU | 52 | 1timesat | 1337 NSP2 | | |
| GCCUGUGGAUGUGGGGCAUCAUAUA | 53 | 1timesat | 1343 NSP2 | | |
| GGAUGUGGGGCAUCAUAUACAGCUA | 54 | 1timesat | 1349 NSP2 | | |
| GGCGUAGCUUACGCCUACUUUGGAU | 55 | 1timesat | 1559 NSP2 | | |
| GCCUACUUUGGAUGUGAGGAAGGUA | 56 | 1timesat | 1571 NSP2 | | |
| CCUAGAGCUAAGUCUGUUGUCUCAA | 57 | 1timesat | 1610 NSP2 | | |
| CCUUAACUUUGUGGGAGAGUUCGUU | 58 | 1timesat | 1726 NSP2 | | |

TABLE 1-continued

Predicted 25 mer siRNA targeting
MERS NC019843.3
25mer blunt ended sequences

| SiRNA sequence | SEQ ID NO: | | Start Base | Protein Coded | 23 mer Sequences passing all metrics and BLAST search (allows for 2 base overhang on 21mer) | SEQ ID NO: |
|---|---|---|---|---|---|---|
| GGGAGAGUUCGUUGUCAACGAUGUU | 59 | 1 timesat | 1738 | NSP2 | | |
| GCCGGCCCAUUCAUGGAUAAUGCUA | 60 | 1 timesat | 1880 | NSP2 | | |
| CCGGCCCAUUCAUGGAUAAUGCUAU | 61 | 1 timesat | 1881 | NSP2 | | |
| CGGCCCAUUCAUGGAUAAUGCUAUU | 62 | 1 timesat | 1882 | NSP2 | | |
| GGCCCAUUCAUGGAUAAUGCUAUUA | 63 | 1 timesat | 1883 | NSP2 | | |
| GCCCAUUCAUGGAUAAUGCUAUUAA | 64 | 1 timesat | 1884 | NSP2 | GCCCAUUCAUGGAUAAUGCUAUU | 953 |
| CCCAUUCAUGGAUAAUGCUAUUAAU | 65 | 1 timesat | 1885 | NSP2 | CCCAUUCAUGGAUAAUGCUAUUA | 954 |
| GCUAUUAAUGUUGGUGGUACAGGAU | 66 | 1 timesat | 1901 | NSP2 | | |
| CGCCAUUACUGCACCUUAUGUAGUU | 67 | 1 timesat | 1936 | NSP2 | CGCCAUUACUGCACCUUAUGUAG | 955 |
| GCUCACAGCGUGUUGUACAGAGUUU | 68 | 1 timesat | 2048 | NSP2 | | |
| GCGUGUUGUACAGAGUUUUUCCUUA | 69 | 1 timesat | 2055 | NSP2 | | |
| CGUGUUGUACAGAGUUUUUCCUUAU | 70 | 1 timesat | 2056 | NSP2 | GUGUUGUACAGAGUUUUUCCUUA | 956 |
| GGCGACUUUAUGUCUACAAUUAUUA | 71 | 1 timesat | 2186 | NSP2 | GGCGACUUUAUGUCUACAAUUAU | 957 |
| CCAAACUGCUGUUAGUAAGCUUCUA | 72 | 1 timesat | 2218 | NSP2 | | |
| GCUGUUAGUAAGCUUCUAGAUACAU | 73 | 1 timesat | 2225 | NSP2 | CUGUUAGUAAGCUUCUAGAUACA | 958 |
| GCAACAUUUAACUUCUUGUUAGAUU | 74 | 1 timesat | 2267 | NSP2 | AACAUUUAACUUCUUGUUAGAUU | 959 |
| CCUAUGUGUACACUUCACAAGGGUU | 75 | 1 timesat | 2325 | NSP2 | | |
| GGAACCUAUUACUGUGUCACCACUA | 76 | 1 timesat | 2504 | NSP2 | | |
| GGUUGAAACUGUUGUGGGUCAACUU | 77 | 1 timesat | 2653 | NSP2 | | |
| GCAAACUAAUAUGCAUAGUCCUGAU | 78 | 1 timesat | 2680 | NSP2 | | |
| GGUGACUAUGUCAUUAUUAGUGAAA | 79 | 1 timesat | 2714 | NSP2 | | |
| GGGAGGUGCACCUGUAAAAAAAGUA | 80 | 1 timesat | 2830 | NSP2 | | |
| CGAGUACAACAUUCAUGCUGUAUUA | 81 | 1 timesat | 2908 | NSP3 | | |
| GCUGUAUUAGACACACUACUUGCUU | 82 | 1 timesat | 2924 | NSP3 | | |
| GGAGUUUGCUGACGUAGUAAAGGAA | 83 | 1 timesat | 2995 | NSP3 | | |
| GCGUGGAAUGCCGAUUCCAGAUUUU | 84 | 1 timesat | 3049 | NSP3 | | |
| GGAAUGCCGAUUCCAGAUUUUGAUU | 85 | 1 timesat | 3053 | NSP3 | | |
| CCAGAUUUUGAUUUAGACGAUUUUA | 86 | 1 timesat | 3065 | NSP3 | | |
| CGAUUUUAUUGACGCACCAUGCUAU | 87 | 1 timesat | 3082 | NSP3 | | |
| CCCGUCGAGUGUGACGAGGAGUGUU | 88 | 1 timesat | 3164 | NSP3 | | |
| CGAGUGUGACGAGGAGUGUUCUGAA | 89 | 1 timesat | 3169 | NSP3 | | |
| GGCUUCAGAUUUAGAAGAAGGUGAA | 90 | 1 timesat | 3199 | NSP3 | | |
| GCUUCAGAUUUAGAAGAAGGUGAAU | 91 | 1 timesat | 3200 | NSP3 | | |
| CGACGAGUGGGCUGCUGCAGUUGAU | 92 | 1 timesat | 3283 | NSP3 | | |
| CGAGUGGGCUGCUGCAGUUGAUGAA | 93 | 1 timesat | 3286 | NSP3 | | |
| GGGCUGCUGCAGUUGAUGAAGCGUU | 94 | 1 timesat | 3291 | NSP3 | | |

TABLE 1-continued

Predicted 25 mer siRNA targeting
MERS NC019843.3
25mer blunt ended sequences

| SiRNA sequence | SEQ ID NO: | | Start Base | Protein Coded | 23 mer Sequences passing all metrics and BLAST search (allows for 2 base overhang on 21mer) | SEQ ID NO: |
|---|---|---|---|---|---|---|
| GCAAGAAGAAGCACAACCAGUAGAA | 95 | 1 timesat | 3352 | NSP3 | | |
| CCAGUAGAAGUACCUGUUGAAGAUA | 96 | 1 timesat | 3368 | NSP3 | | |
| GCAGGUUGUCAUAGCUGACACCUUA | 97 | 1 timesat | 3397 | NSP3 | | |
| GGUUAUUACAGAGUGCGUUACCAUA | 98 | 1 timesat | 3628 | NSP3 | | |
| GGCGGUGGUAUCGCUGGUGCUAUUA | 99 | 1 timesat | 3734 | NSP3 | | |
| GCGGUGGUAUCGCUGGUGCUAUUAA | 100 | 1 timesat | 3735 | NSP3 | | |
| CGGUGGUAUCGCUGGUGCUAUUAAU | 101 | 1 timesat | 3736 | NSP3 | | |
| GCUGGUGCUAUUAAUGCGGCUUCAA | 102 | 1 timesat | 3746 | NSP3 | | |
| GCGGCUUCAAAAGGGGCUGUCCAAA | 103 | 1 timesat | 3761 | NSP3 | | |
| CGGCUUCAAAAGGGGCUGUCCAAAA | 104 | 1 timesat | 3762 | NSP3 | | |
| GGCUUCAAAAGGGGCUGUCCAAAAA | 105 | 1 timesat | 3763 | NSP3 | | |
| GCCGUUACAAGUAGGAGAUUCAGUU | 106 | 1 timesat | 3817 | NSP3 | | |
| CGUAGGCCCAGAUGCCCGCGCUAAA | 107 | 1 timesat | 3883 | NSP3 | | |
| CCCAGAUGCCCGCGCUAAACAGGAU | 108 | 1 timesat | 3889 | NSP3 | | |
| GGCUAUGAAUGCAUAUCCUCUUGUA | 109 | 1 timesat | 3940 | NSP3 | | |
| CCAGCUGUGUCUUUUGAUUAUCUUA | 110 | 1 timesat | 4004 | NSP3 | | |
| GCUGUGUCUUUUGAUUAUCUUAUUA | 111 | 1 timesat | 4007 | NSP3 | CUGUGUCUUUUGAUUAUCUUAUU | 960 |
| CGUCGUUAAUUCCCAAGAUGUCUAU | 112 | 1 timesat | 4057 | NSP3 | | |
| GGCGCAAUACGUAAAGCUAAAGAUU | 113 | 1 timesat | 4142 | NSP3 | | |
| GCGCAAUACGUAAAGCUAAAGAUUA | 114 | 1 timesat | 4143 | NSP3 | | |
| CGCAAUACGUAAAGCUAAAGAUUAU | 1 | 1 timesat | 4144 | NSP3 | CGCAAUACGUAAAGCUAAAGAUU | 961 |
| CGUAAAGCUAAAGAUUAUGGUUUUA | 115 | 1 timesat | 4151 | NSP3 | | |
| GCUAAAGAUUAUGGUUUUACUGUUU | 116 | 1 timesat | 4157 | NSP3 | | |
| GCACAGACAACUCUGCUAACACUAA | 117 | 1 timesat | 4188 | NSP3 | | |
| GGAACAAGGGUGUUGAUUAUACUAA | 118 | 1 timesat | 4221 | NSP3 | | |
| GGGUGUUGAUUAUACUAAGAAGUUU | 2 | 1 timesat | 4228 | NSP3 | GGGUGUUGAUUAUACUAAGAAGU | 962 |
| CGUCUAAGGACACUUUAGAUGAUAU | 119 | 1 timesat | 4287 | NSP3 | | |
| GGACACUUUAGAUGAUAUCUUACAA | 120 | 1 timesat | 4294 | NSP3 | GACACUUUAGAUGAUAUCUUACA | 963 |
| GCUAAUAAGUCUGUUGGUAUUAUAU | 121 | 1 timesat | 4322 | NSP3 | | |
| GGUAUUAUAUCUAUGCCUUUGGGAU | 122 | 1 timesat | 4337 | NSP3 | | |
| CCUUUGGGAUAUGUGUCUCAUGGUU | 123 | 1 timesat | 4352 | NSP3 | | |
| GCCCUACGUGUGUCUCCUAGCUAAU | 124 | 1 timesat | 4420 | NSP3 | | |
| CCCUACGUGUGUCUCCUAGCUAAUA | 125 | 1 timesat | 4421 | NSP3 | | |
| CCUACGUGUGUCUCCUAGCUAAUAA | 126 | 1 timesat | 4422 | NSP3 | | |
| GCUAAUAAAGAGCAAGAAGCUAUUU | 127 | 1 timesat | 4439 | NSP3 | | |
| GCAAGAAGCUAUUUUGAUGUCUGAA | 128 | 1 timesat | 4450 | NSP3 | | |

TABLE 1-continued

Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21mer) | SEQ ID NO: |

TABLE 1-continued

Predicted 25 mer siRNA targeting
MERS NC019843.3
25mer blunt ended sequences

| S

TABLE 1-continued

Predicted 25 mer siRNA targeting
MERS NC019843.3
25mer blunt ended sequences

| SiRNA sequence | SEQ ID NO: | Start | Protein Base Coded | 23 mer Sequences passing all metrics and BLAST search (allows for 2 base overhang on 21mer) | SEQ ID NO: |

TABLE 1-continued

Predicted 25 mer siRNA targeting
MERS NC019843.3
25mer blunt ended sequences

| SiRNA sequence | SEQ ID NO: | | StartProtein Base Coded | 23 mer Sequences passing all metrics and BLAST search (allows for 2 base overhang on 21mer) | SEQ ID NO: |

TABLE 1-continued

Predicted 25 mer siRNA targeting MERS NC019843.3 25mer blunt ended sequences

| SiRNA sequence | SEQ ID NO: | | Start Base | Protein Coded | 23 mer Sequences passing all metrics and BLAST search (allows for 2 base overhang on 21mer) | SEQ ID NO: |
|---|---|---|---|---|---|---|
| CCACAAAUGGCUCGUGGGCCAUUUU | 268 | 1 timesat | 9225 | NSP4 | | |
| GGCCAUUUUUAAUGACCACCAUCUU | 269 | 1 timesat | 9241 | NSP4 | | |
| GCCAUUUUUAAUGACCACCAUCUUA | 270 | 1 timesat | 9242 | NSP4 | | |
| CCAUUUUUAAUGACCACCAUCUUAA | 271 | 1 timesat | 9243 | NSP4 | | |
| CCAUCUUAAUAGACCUGGUGUCUAU | 272 | 1 timesat | 9259 | NSP4 | | |
| CCUGGUGUCUAUUGUGGCUCUGAUU | 273 | 1 timesat | 9272 | NSP4 | | |
| GGUGUCUAUUGUGGCUCUGAUUUUA | 274 | 1 timesat | 9275 | NSP4 | | |
| GCAGUAUCACUGUUCCAGCCUAUUA | 275 | 1 timesat | 9320 | NSP4 | | |
| CCUAUUACUUAUUUCCAAUUGACUA | 276 | 1 timesat | 9338 | NSP4 | | |
| CCUCAUUGGUCUUGGGUAUAGGUUU | 277 | 1 timesat | 9363 | NSP4 | | |
| CCUGACUUUGCUCUUCUAUUAUAUU | 278 | 1 timesat | 9397 | NSP4 | | |
| GCUCUUCUAUUAUAUUAAUAAAGUA | 279 | 1 timesat | 9406 | NSP4 | CUCUUCUAUUAUAUUAAUAAAGU | 982 |
| GCUGUUGUUGCUGCUGUUCUUAAUA | 280 | 1 timesat | 9470 | NSP4 | | |
| CCUGCAUUUAUUAUGCAUGUUUCUU | 281 | 1 timesat | 9587 | NSP4 | | |
| CCAGGACGCUGCCUCUAAUAUCUUU | 282 | 1 timesat | 9760 | NSP4 | | |
| GGACGCUGCCUCUAAUAUCUUUGUU | 283 | 1 timesat | 9763 | NSP4 | | |
| CGCUGCCUCUAAUAUCUUUGUUAUU | 284 | 1 timesat | 9766 | NSP4 | | |
| GCUGCCUCUAAUAUCUUUGUUAUUA | 285 | 1 timesat | 9767 | NSP4 | UGCCUCUAAUAUCUUUGUUAUUA | 983 |
| CCUCUAAUAUCUUUGUUAUUAACAA | 286 | 1 timesat | 9771 | NSP4 | CUCUAAUAUCUUUGUUAUUAACA | 984 |
| GCAGCUCUUAGAAACUCUUUAACUA | 287 | 1 timesat | 9806 | NSP4 | CAGCUCUUAGAAACUCUUUAACU | 985 |
| CCUAUUCACGAUUUUUGGGGUUGUU | 288 | 1 timesat | 9837 | NSP4 | | |
| GGUUGUUUAACAAGUAUAAGUACUU | 289 | 1 timesat | 9855 | NSP4 | | |
| GCCGCUUAUCGUGAAGCUGCAGCAU | 290 | 1 timesat | 9899 | NSP4 | | |
| GCGAGACUGGUAGUGAUCUUCUUUA | 291 | 1 timesat | 9954 | NSP4 | | |
| CCUCUGGCGUGUUGCAAAGCGGUUU | 292 | 1 timesat | 10002 | NSP4 | | |
| GCGUGUUGCAAAGCGGUUUGGUGAA | 293 | 1 timesat | 10008 | NSP4 | | |
| CGUGUUGCAAAGCGGUUUGGUGAAA | 294 | 1 timesat | 10009 | NSP4 | | |
| GGUUACCUGCGGUAGCAUGACUCUU | 295 | 1 timesat | 10075 | NSP5 | | |
| CGGUAGCAUGACUCUUAAUGGUCUU | 296 | 1 timesat | 10084 | NSP5 | | |
| GGUAGCAUGACUCUUAAUGGUCUUU | 297 | 1 timesat | 10085 | NSP5 | | |
| CCUAAUUAUGAUGCCUUGUUGAUUU | 298 | 1 timesat | 10172 | NSP5 | | |
| CGCUCCAGCAAACUUGCGUGUUGUU | 299 | 1 timesat | 10237 | NSP5 | | |
| GGUCAUGCCAUGCAAGGCACUCUUU | 300 | 1 timesat | 10262 | NSP5 | | |
| GGCGCAGCAUUUAGUGUGUUAGCAU | 301 | 1 timesat | 10352 | NSP5 | | |
| GCAUUUAGUGUGUUAGCAUGCUAUA | 302 | 1 timesat | 10358 | NSP5 | | |
| CCGACUGGUACAUUCACUGUUGUAA | 303 | 1 timesat | 10391 | NSP5 | | |

TABLE 1-continued

Predicted 25 mer siRNA targeting MERS NC019843.3 25mer blunt ended sequences

| SiRNA sequence | SEQ ID NO: | | StartProtein Base Coded | 23 mer Sequences passing all metrics and BLAST search (allows for 2 base overhang on 21mer) | SEQ ID NO: |
|---|---|---|---|---|---|
| CGACUGGUACAUUCACUGUUGUAAU | 304 | 1timesat | 10392NSP5 | | |
| CGCCCUAACUACACAAUUAAGGGUU | 305 | 1timesat | 10418NSP5 | | |
| CCGGUUCAGCAUUUGAUGGUACUAU | 306 | 1timesat | 10545NSP5 | | |
| GCACCAAGUUCAGUUAACAGACAAA | 307 | 1timesat | 10597NSP5 | | |
| GCUUGGCUUUACGCAGCAAUACUUA | 308 | 1timesat | 10643NSP5 | | |
| GCAGCAAUACUUAAUGGUUGCGCUU | 309 | 1timesat | 10655NSP5 | | |
| GGCGUUGCUAUUGAACAGCUGCUUU | 310 | 1timesat | 10793NSP5 | | |
| GCGUUGCUAUUGAACAGCUGCUUUA | 311 | 1timesat | 10794NSP5 | | |
| CGUUGCUAUUGAACAGCUGCUUUAU | 312 | 1timesat | 10795NSP5 | | |
| GGAAGAUGAAUUCACACCUGAGGAU | 313 | 1timesat | 10879NSP5 | | |
| CCUGAGGAUGUUAAUAUGCAGAUUA | 314 | 1timesat | 10895NSP5 | | |
| GGUUAUGCAGAGUGGUGUGAGAAAA | 315 | 1timesat | 10927NSP5 | | |
| GGUGUGAGAAAAGUUACAUAUGGUA | 316 | 1timesat | 10940NSP6 | | |
| CGACCCUUGUCUCAACCUAUGUGAU | 317 | 1timesat | 10983NSP6 | | |
| CCCUUGUCUCAACCUAUGUGAUAAU | 318 | 1timesat | 10986NSP6 | | |
| CCACUAAAUUUACUUUGUGGAACUA | 319 | 1timesat | 11019NSP6 | | |
| CCCACACAGUUGUUCCCACUCUUAU | 320 | 1timesat | 11060NSP6 | | |
| CCACACAGUUGUUCCCACUCUUAUU | 321 | 1timesat | 11061NSP6 | | |
| GGCCUUCGUUAUGUUGUUGGUUAAA | 322 | 1timesat | 11095NSP6 | | |
| CGUUAUGUUGUUGGUUAAACACAAA | 323 | 1timesat | 11101NSP6 | | |
| GCCUGUGGCUAUUUGUUUGACUUAU | 324 | 1timesat | 11152NSP6 | | |
| GCAAACAUAGUCUACGAGCCCACUA | 325 | 1timesat | 11177NSP6 | | |
| CGUCAGCGCUGAUUGCAGUUGCAAA | 326 | 1timesat | 11211NSP6 | | |
| GCUGAUUGCAGUUGCAAAUUGGCUU | 327 | 1timesat | 11218NSP6 | | |
| GGCUUGCCCCCACUAAUGCUUAUAU | 328 | 1timesat | 11238NSP6 | | |
| CCCACUAAUGCUUAUAUGCGCACUA | 329 | 1timesat | 11246NSP6 | | |
| GGUGUAAUGUGGUUGUACACUUAUA | 330 | 1timesat | 11378NSP6 | | |
| GCAUUGGAGAAGCCUCAAGCCCCAU | 331 | 1timesat | 11403NSP6 | | |
| CCGGAAGUGAAGAUGAUACUUUUAU | 332 | 1timesat | 11555NSP6 | | |
| CGGAAGUGAAGAUGAUACUUUUAUU | 333 | 1timesat | 11556NSP6 | CGGAAGUGAAGAUGAUACUUUUA | 986 |
| GGAAGUGAAGAUGAUACUUUUAUUA | 334 | 1timesat | 11557NSP6 | AAGUGAAGAUGAUACUUUUAUUA | 987 |
| GCUUAGAGCACCUAUGGGUGUCUAU | 335 | 1timesat | 11644NSP6 | | |
| GCACCUAUGGGUGUCUAUGACUUUA | 336 | 1timesat | 11651NSP6 | | |
| GCUAACAAUCUAACUGCACCUAGAA | 337 | 1timesat | 11708NSP6 | | |
| GCACCUAGAAAUUCUUGGGAGGCUA | 338 | 1timesat | 11723NSP6 | | |

TABLE 1-continued

Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21mer) | SEQ TABLE 1-continued Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on TABLE 1-continued Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21mer) | SEQ ID NO: |
|---|---|---|---|---|
| CCUCAUAUUGUACGUCAGCGUUUAA | 411 | 1timesat 13747NSP12 | | |
| CGUCAGCGUUUAACUGAGUACACUA | 412 | 1timesat 13759NSP12 | | |
| GCCCUGAGGCACUUUGAUCAAAAUA | 413 | 1timesat 13801NSP12 | | |
| GCUUAAGGCUAUCUUAGUGAAGUAU | 414 | 1timesat 13833NSP12 | | |
| GCUGUGAUGUUACCUACUUUGAAAA | 415 | 1timesat 13862NSP12 | CUGUGAUGUUACCUACUUUGAAA | 992 |
| CCUACUUUGAAAAUAAACUCUGGUU | 416 | 1timesat 13874NSP12 | | |
| CCCAGUGUUAUUGGUGUUUAUCAUA | 7 | 1timesat 13915NSP12 | CCCAGUGUUAUUGGUGUUUAUCA | 993 |
| CCAGUGUUAUUGGUGUUUAUCAUAA | 417 | 1timesat 13916NSP12 | CAGUGUUAUUGGUGUUUAUCAUA | 994 |
| CGCCAAGCUAUCUUAAACACUGUUA | 418 | 1timesat 13957NSP12 | | |
| GCCAAGCUAUCUUAAACACUGUUAA | 419 | 1timesat 13958NSP12 | | |
| CCAAGCUAUCUUAAACACUGUUAAA | 420 | 1timesat 13959NSP12 | | |
| GCUAUCUUAAACACUGUUAAAUUUU | 421 | 1timesat 13963NSP12 | | |
| GCUCACACUAGACAACCAGGACCUU | 422 | 1timesat 14022NSP12 | | |
| CCAGGACCUUAAUGGCAAGUGGUAU | 423 | 1timesat 14037NSP12 | | |
| GGACCUUAAUGGCAAGUGGUAUGAU | 424 | 1timesat 14040NSP12 | | |
| CCUUAAUGGCAAGUGGUAUGAUUUU | 425 | 1timesat 14043NSP12 | | |
| GCAAGUGGUAUGAUUUUGGUGACUU | 426 | 1timesat 14051NSP12 | | |
| GGUAUGAUUUUGGUGACUUCGUAAU | 427 | 1timesat 14057NSP12 | | |
| GGUUCAGGAGUAGCUAUAGUUGAUA | 428 | 1timesat 14092NSP12 | | |
| GCUAUAGUUGAUAGCUACUAUUCUU | 429 | 1timesat 14104NSP12 | | |
| CGAUUGUCUGGCCGCUGAGACACAU | 430 | 1timesat 14154NSP12 | | |
| CGCUGAGACACAUAGGGAUUGUGAU | 431 | 1timesat 14166NSP12 | | |
| GCUGAGACACAUAGGGAUUGUGAUU | 432 | 1timesat 14167NSP12 | | |
| GGUACAACUCUUUGAGAAGUACUUU | 433 | 1timesat 14247NSP12 | UACAACUCUUUGAGAAGUACUUU | 995 |
| CGCAAAUUGCGUUAAUUGUACUGAU | 434 | 1timesat 14295NSP12 | | |
| CCGUUGUGUGUUACAUUGUGCUAAU | 435 | 1timesat 14322NSP12 | | |
| CGUUGUGUGUUACAUUGUGCUAAUU | 436 | 1timesat 14323NSP12 | | |
| GCUAAUUUCAAUGUAUUGUUUGCUA | 437 | 1timesat 14341NSP12 | | |
| GCCUAAGACUUGUUUCGGACCCAUA | 438 | 1timesat 14373NSP12 | | |
| CGGACCCAUAGUCCGAAAGAUCUUU | 439 | 1timesat 14388NSP12 | | |
| GCCAUUGUAGUAUCUUGUGGUUAU | 440 | 1timesat 14424NSP12 | | |
| GGUUAUCACUACAAAGAAUUAGGUU | 441 | 1timesat 14443NSP12 | | |
| GGUUUAGUCAUGAAUAUGGAUGUUA | 442 | 1timesat 14464NSP12 | | |
| CCAGCCAUGCACAUUGCCUCCUCUA | 443 | 1timesat 14542NSP12 | | |
| GCACAUUGCCUCCUCUAACGCUUUU | 444 | 1timesat 14550NSP12 | | |

TABLE 1-continued

Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21mer) | SEQ ID NO: |
|---|---|---|---|---|
| GCCUCCUCUAACGCUUUUCUUGAUU | 445 | 1timesat 14557NSP12 | | |
| CCUCCUCUAACGCUUUUCUUGAUUU | 446 | 1timesat 14558NSP12 | CUCCUCUAACGCUUUUCUUGAUU | 996 |
| GCUUUUCUUGAUUUGAGGACAUCAU | 447 | 1timesat 14569NSP12 | | |
| GCUGCACUUACAACUGGUUUGACUU | 448 | 1timesat 14605NSP12 | | |
| GGCCUGGCAAUUUUAACCAAGACUU | 449 | 1timesat 14642NSP12 | | |
| CCAAGACUUCUAUGAUUUCGUGGUA | 450 | 1timesat 14658NSP12 | | |
| GCUCAAACAUUUUUUCUUUGCUCAA | 451 | 1timesat 14718NSP12 | | |
| GCUCAAGAUGGUAAUGCUGCUAUUA | 452 | 1timesat 14737NSP12 | | |
| GGUAAUGCUGCUAUUACAGAUUAUA | 453 | 1timesat 14746NSP12 | | |
| GCUAUUACAGAUUAUAAUUACUAUU | 454 | 1timesat 14755NSP12 | | |
| GCCUACUAUGUGUGACAUCAAACAA | 455 | 1timesat 14790NSP12 | | |
| CCUACUAUGUGUGACAUCAAACAAA | 456 | 1timesat 14791NSP12 | UACUAUGUGUGACAUCAAACAAA | 997 |
| GCAUGGAAGUUGUAAACAAGUACUU | 457 | 1timesat 14825NSP12 | | |
| GGAAGUUGUAAACAAGUACUUCGAA | 458 | 1timesat 14829NSP12 | | |
| CGAAAUCUAUGACGGUGGUUGUCUU | 459 | 1timesat 14850NSP12 | | |
| CGGUGGUUGUCUUAAUGCUUCUGAA | 460 | 1timesat 14862NSP12 | | |
| GCUUCUGAAGUGGUUGUUAAUAAUU | 461 | 1timesat 14878NSP12 | | |
| GCCAUCCUUUUAAUAAGUUUGGCAA | 462 | 1timesat 14918NSP12 | | |
| CCAUCCUUUUAAUAAGUUUGGCAAA | 463 | 1timesat 14919NSP12 | | |
| CGUGUCUAUUAUGAGAGCAUGUCUU | 464 | 1timesat 14947NSP12 | | |
| GCAGGCGUGUCCAUACUUAGCACAA | 465 | 1timesat 15082NSP12 | | |
| CGCCAGUACCAUCAGAAAAUGCUUA | 466 | 1timesat 15115NSP12 | | |
| GCCAGUACCAUCAGAAAAUGCUUAA | 467 | 1timesat 15116NSP12 | | |
| CGUGGAGCGACUUGCGUCAUUGGUA | 468 | 1timesat 15157NSP12 | | |
| GGAGCGACUUGCGUCAUUGGUACUA | 469 | 1timesat 15160NSP12 | | |
| GCGACUUGCGUCAUUGGUACUACAA | 470 | 1timesat 15163NSP12 | | |
| CGACUUGCGUCAUUGGUACUACAAA | 471 | 1timesat 15164NSP12 | | |
| GCGUCAUUGGUACUACAAAGUUCUA | 472 | 1timesat 15170NSP12 | | |
| GGUGGCUGGGAUUUCAUGCUUA TABLE 1-continued Predicted 25 mer siRNA targeting
MERS NC019843.3
25mer blunt ended sequences

| SiRNA sequence | SEQ ID NO: | | StartProtein Base Coded | 23 mer Sequences passing all metrics and BLAST search (allows for 2 base overhang on 21mer) | SEQ ID NO: |
|---|---|---|---|---|---|
| CGCUUCACUCAUAUUAGCUCGUAAA | 480 | 1 timesat | 15309NSP12 | | |
| GGGACAGAUUUUAUCGCUUGGCAAA | 481 | 1 timesat | 15356NSP12 | | |
| GGACAGAUUUUAUCGCUUGGCAAAU | 482 | 1 timesat | 15357NSP12 | | |
| GGCAAAUGAGUGUGCUCAGGUGCUA | 483 | 1 timesat | 15375NSP12 | | |
| GCAAAUGAGUGUGCUCAGGUGCUAA | 484 | 1 timesat | 15376NSP12 | | |
| GGUUACUACGUCAAACCUGGAGGUA | 485 | 1 timesat | 15424NSP12 | | |
| CCACUGCAUAUGCCAAUAGUGUCUU | 486 | 1 timesat | 15467NSP12 | CACUGCAUAUGCCAAUAGUGUCU | 1000 |
| GGGUGCUAAUGGCAACAAGAUUGUU | 9 | 1 timesat | 15534NSP12 | GGGUGCUAAUGGCAACAAGAUUG | 1001 |
| GGAGCACUAGCCCAGACCCCAAAUU | 487 | 1 timesat | 15608NSP12 | | |
| GCCCAGACCCCAAAUUUGUUGAUAA | 488 | 1 timesat | 15617NSP12 | | |
| CCCAGACCCCAAAUUUGUUGAUAAA | 489 | 1 timesat | 15618NSP12 | | |
| CCAGACCCCAAAUUUGUUGAUAAAU | 490 | 1 timesat | 15619NSP12 | | |
| CCCCAAAUUUGUUGAUAAAUACUAU | 10 | 1 timesat | 15624NSP12 | CCCCAAAUUUGUUGAUAAAUACU | 1002 |
| GCUUUUCUUAAUAAGCACUUUUCUA | 491 | 1 timesat | 15649NSP12 | | |
| CGGUGUCGUUUGCUAUAAUAGUGAU | 492 | 1 timesat | 15693NSP12 | | |
| GGUGUCGUUUGCUAUAAUAGUGAUU | 493 | 1 timesat | 15694NSP12 | | |
| GCUAUAAUAGUGAUUAUGCAGCUAA | 494 | 1 timesat | 15704NSP12 | | |
| GCAGCUAAGGGUUACAUUGCUGGAA | 495 | 1 timesat | 15721NSP12 | | |
| GGGUUACAUUGCUGGAAUACAGAAU | 496 | 1 timesat | 15729NSP12 | | |
| GGUUACAUUGCUGGAAUACAGAAUU | 497 | 1 timesat | 15730NSP12 | | |
| GGAAACGCUGUAUUAUCAGAACAAU | 498 | 1 timesat | 15759NSP12 | | |
| CGCUGUAUUAUCAGAACAAUGUCUU | 499 | 1 timesat | 15764NSP12 | | |
| GCUGUAUUAUCAGAACAAUGUCUUU | 500 | 1 timesat | 15765NSP12 | | |
| GCUGGGUGGAAACCGAUCUGAAGAA | 501 | 1 timesat | 15806NSP12 | | |
| CGAUCUGAAGAAAGGGCCACAUGAA | 502 | 1 timesat | 15819NSP12 | | |
| GCCACAUGAAUUCUGUUCACAGCAU | 503 | 1 timesat | 15834NSP12 | | |
| CCACAUGAAUUCUGUUCACAGCAUA | 504 | 1 timesat | 15835NSP12 | | |
| GCUUUAUAUUAAGGAUGGCGACGAU | 505 | 1 timesat | 15861NSP12 | | |
| GGAUGGCGACGAUGGUUACUUCCUU | 506 | 1 timesat | 15873NSP12 | | |
| GGCGACGAUGGUUACUUCCUUCCUU | 507 | 1 timesat | 15877NSP12 | | |
| GCGACGAUGGUUACUUCCUUCCUUA | 508 | 1 timesat | 15878NSP12 | | |
| CGACGAUGGUUACUUCCUUCCUUAU | 509 | 1 timesat | 15879NSP12 | | |
| CCUUAUCCAGACCCUUCAAGAAUUU | 510 | 1 timesat | 15898NSP12 | | |
| CCUUCAAGAAUUUUGUCUGCCGGUU | 511 | 1 timesat | 15910NSP12 | | |
| CGGUUGCUUUGUAGAUGAUAUCGUU | 11 | 1 timesat | 15930NSP12 | CGGUUGCUUUGUAGAUGAUAUCG | 1003 |

TABLE 1-continued

Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21mer) | SEQ ID NO: |
|---|---|---|---|---|
| GGUUGCUUUGUAGAUGAUAUCGUUA | 512 | 1timesat 15931NSP12 | UUGCUUUGUAGAUGAUAUCGUUA | 1004 |
| GCGGUUUGUGUCUUUGGCUAUAGAU | 513 | 1timesat 15981NSP12 | | |
| GCUAUAGAUGCUUACCCUCUCACAA | 514 | 1timesat 15997NSP12 | | |
| CCCUCUCACAAAGCAUGAAGAUAUA | 515 | 1timesat 16011NSP12 | CUCUCACAAAGCAUGAAGAUAUA | 1005 |
| GCAUGAAGAUAUAGAAUACCAGAAU | 516 | 1timesat 16023NSP12 | | |
| CCAGAAUGUAUUCUGGGUCUACUUA | 517 | 1timesat 16041NSP12 | | |
| GGGUCUACUUACAGUAUAUAGAAAA | 518 | 1timesat 16055NSP12 | | |
| GGUCUACUUACAGUAUAUAGAAAAA | 519 | 1timesat 16056NSP12 | GUCUACUUACAGUAUAUAGAAAA | 1006 |
| GCUUGACAGUUAUUCUGUCAUGCUA | 520 | 1timesat 16107NSP12 | | |
| CCUACCACUUUGCAGGCUGUCGGUU | 521 | 1timesat 16192NSP12 | | |
| GCAGGCUGUCGGUUCAUGCGUUGUA | 522 | 1timesat 16203NSP12 | | |
| CCACAUAAGAUGGUUUUGUCUGUUU | 523 | 1timesat 16318NSP13 | | |
| CCACUUUGCGCUAAUGGUCUUGUAU | 524 | 1timesat 16450NSP13 | | |
| GCGCUAAUGGUCUUGUAUUCGGCUU | 525 | 1timesat 16457NSP13 | | |
| CGCUAAUGGUCUUGUAUUCGGCUUA | 526 | 1timesat 16458NSP13 | | |
| GCUAAUGGUCUUGUAUUCGGCUUAU | 527 | 1timesat 16459NSP13 | | |
| GGUGAUUACACCCUUGCCAAUACUA | 528 | 1timesat 16558NSP13 | | |
| CCAAUACUACAACAGAACCACUCAA | 529 | 1timesat 16574NSP13 | | |
| CCACCACUCAAUCGUAAUUAUGUUU | 530 | 1timesat 16726NSP13 | ACCACUCAAUCGUAAUUAUGUUU | 1007 |
| CCACUCAAUCGUAAUUAUGUUUUUA | 531 | 1timesat 16729NSP13 | | |
| GGUUAUCAUAUAACCAAAAAUAGUA | 532 | 1timesat 16756NSP13 | | |
| GCGCAUUGAUUAUAGUGAUGCUGUA | 533 | 1timesat 16809NSP13 | | |
| CGCAUUGAUUAUAGUGAUGCUGUAU | 534 | 1timesat 16810NSP13 | | |
| GCUGUAUCCUACAAGUCUAGUACAA | 535 | 1timesat 16828NSP13 | | |
| CCUACAAGUCUAGUACAACGUAUAA | 536 | 1timesat 16835NSP13 | UACAAGUCUAGUACAACGUAUAA | 1008 |
| CGUAUAAACUGACUGUAGGUGACAU | 537 | 1timesat 16853NSP13 | | |
| GGCUACCUUGACGGCGCCCACAAUU | 538 | 1timesat 16902NSP13 | | |
| GGUAUGUUAAAAUUACUGGGUUGUA | 539 | 1timesat 16940NSP13 | | |
| GCCAACUUCCAAAAAUCAGGUUAUA | 540 | 1timesat 17005NSP13 | | |
| CCAAAAAUCAGGUUAUAGUAAAUAU | 541 | 1timesat 17013NSP13 | | |
| GCACGUGUUGUUUAUACAGCAUGUU | 542 | 1timesat 17110NSP13 | | |
| CGCAGCUGUUGAUGCUUUGUGUGAA | 543 | 1timesat 17139NSP13 | | |
| GCAGCUGUUGAUGCUUUGUGUGAAA | 544 | 1timesat 17140NSP13 | | |
| GCUUUGUGUGAAAAAGCUUUUUAAAU | 545 | 1timesat 17152NSP13 | | |
| GCUUUUAAAUAUUUGAACAUUGCUA | 546 | 1timesat 17167NSP13 | | |
| CGUGUUGAGUGCUAUGACAGGUUUA | 547 | 1timesat 17221NSP13 | | |

TABLE 1-continued

Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21mer) | SEQ ID NO: |
|

TABLE 1-continued

Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21mer) | SEQ TABLE 1-continued Predicted 25 mer siRNA targeting MERS NC019843.3 25mer blunt ended sequences

| SiRNA sequence | SEQ ID NO: | | StartProtein Base Coded | 23 mer Sequences passing all metrics and BLAST search (allows for 2 base overhang on 21mer) | SEQ ID NO: |
|---|---|---|---|---|---|
| CCAUUUUAUUGGUGUUGAGGGUGAA | 619 | 1 timesat | 19611NSP15 | | |
| CCACUUUGCCUACUAAUAUAGCUUU | 620 | 1 timesat | 19712NSP15 | | |
| GCGUGCUGUACGCUCGCAUCCCGAU | 621 | 1 timesat | 19752NSP15 | | |
| CGUGCUGUACGCUCGCAUCCCGAUU | 622 | 1 timesat | 19753NSP15 | | |
| CCCGAUUUCAAAUUGCUACACAAUU | 623 | 1 timesat | 19771NSP15 | | |
| CCGAUUUCAAAUUGCUACACAAUUU | 624 | 1 timesat | 19772NSP15 | | |
| CGAUUUCAAAUUGCUACACAAUUUA | 625 | 1 timesat | 19773NSP15 | | |
| GCUACACAAUUUACAAGCAGACAUU | 626 | 1 timesat | 19785NSP15 | | |
| GCUACAAGUUCGUCCUUUGGGAUUA | 627 | 1 timesat | 19811NSP15 | | |
| CCUUUGGGAUUAUGAACGUAGCAAU | 628 | 1 timesat | 19824NSP15 | | |
| GGGAUUAUGAACGUAGCAAUAUUUA | 629 | 1 timesat | 19829NSP15 | GGGAUUAUGAACGUAGCAAUAUU | 1019 |
| GGAUUAUGAACGUAGCAAUAUUUAU | 630 | 1 timesat | 19830NSP15 | | |
| CGUAGCAAUAUUUAUGGUACUGCUA | 631 | 1 timesat | 19840NSP15 | | |
| GCAAUAUUUAUGGUACUGCUACUAU | 632 | 1 timesat | 19844NSP15 | | |
| CCCAAUGCCAUCUUUAUUUCUGAUA | 633 | 1 timesat | 19966NSP15 | | |
| GCCAUCUUUAUUUCUGAUAGAAAAA | 634 | 1 timesat | 19972NSP15 | GCCAUCUUUAUUUCUGAUAGAAA | 1020 |
| CCAUCUUUAUUUCUGAUAGAAAAAU | 635 | 1 timesat | 19973NSP15 | AUCUUUAUUUCUGAUAGAAAAAU | 1021 |
| CCCUUGUAUGGUAGGUCCUGAUUAU | 636 | 1 timesat | 20007NSP15 | | |
| CCGUGAUAGUGAUGUUGUUAAACAA | 637 | 1 timesat | 20055NSP15 | CCGUGAUAGUGAUGUUGUUAAAC | 1022 |
| GGAAAACUAUGCUUUUGAGCACGUA | 638 | 1 timesat | 20244NSP15 | | |
| CGUUAGGCGGUCUUCACUUGCUUAU | 639 | 1 timesat | 20294NSP15 | | |
| GGCGGUCUUCACUUGCUUAUUGGUU | 640 | 1 timesat | 20299NSP15 | | |
| GCGGUCUUCACUUGCUUAUUGGUUU | 641 | 1 timesat | 20300NSP15 | | |
| CGGUCUUCACUUGCUUAUUGGUUUA | 642 | 1 timesat | 20301NSP15 | | |
| GGUCUUCACUUGCUUAUUGGUUUAU | 643 | 1 timesat | 20302NSP15 | GUCUUCACUUGCUUAUUGGUUUA | 1023 |
| GCUUAUUGGUUUAUACAAGAAGCAA | 644 | 1 timesat | 20313NSP15 | | |
| GGAAGGUCAUAUUAUUAUGGAAGAA | 645 | 1 timesat | 20340NSP15 | | |
| GCUAAAAGGUAGCUCAACUAUUCAU | 646 | 1 timesat | 20367NSP15 | | |
| GGUAGCUCAACUAUUCAUAACUAUU | 647 | 1 timesat | 20374NSP15 | | |
| GCUCAACUAUUCAUAACUAUUUUAU | 648 | 1 timesat | 20378NSP15 | CUCAACUAUUCAUAACUAUUUUA | 1024 |
| GGCUUUUAAGGCGGUGUGUUCUGUU | 649 | 1 timesat | 20421NSP15 | | |
| GCUUUUAAGGCGGUGUGUUCUGUUA | 650 | 1 timesat | 20422NSP15 | | |
| GGCGGUGUGUUCUGUUAUAGAUUUA | 651 | 1 timesat | 20430NSP15 | | |
| GCGGUGUGUUCUGUUAUAGAUUUAA | 652 | 1 timesat | 20431NSP15 | | |
| CGGUGUGUUCUGUUAUAGAUUUAAA | 653 | 1 timesat | 20432NSP15 | | |
| GCUUGACGACUUUGUUAUGAUUUUA | 654 | 1 timesat | 20457NSP15 | | |

TABLE 1-continued

Predicted 25 mer siRNA targeting
MERS NC019843.3
25mer blunt ended sequences

| SiRNA sequence | SEQ ID NO: | | StartProtein Base Coded | 23 mer Sequences passing all metrics and BLAST search (allows for 2 base overhang on 21mer) | SEQ ID NO: |
|---|---|---|---|---|---|
| CGUAGUAUCCAAGGUUGUCAAGGUU | 655 | 1 timesat | 20499NSP15 | | |
| GGUUGUCAAGGUUCCUAUUGACUUA | 656 | 1 timesat | 20511NSP15 | | |
| GGUUCCUAUUGACUUAACAAUGAUU | 657 | 1 timesat | 20520NSP15 | UUCCUAUUGACUUAACAAUGAUU | 1025 |
| CCCUCGACUCCAGGCUUCUGCAGAU | 658 | 1 timesat | 20589NSP15 | | |
| CCUCGACUCCAGGCUUCUGCAGAUU | 659 | 1 timesat | 20590NSP15 | | |
| GCCAUCCCUCUUUAAAGUUCAAAAU | 660 | 1 timesat | 20634NSP16 | | |
| CCCUCUUUAAAGUUCAAAAUGUAAA | 661 | 1 timesat | 20639NSP16 | CUCUUUAAAGUUCAAAAUGUAAA | 1026 |
| CGCGGUGUGCACAUGAACAUCGCUA | 662 | 1 timesat | 20713NSP16 | | |
| GCGGUGUGCACAUGAACAUCGCUAA | 663 | 1 timesat | 20714NSP16 | | |
| CGGUGUGCACAUGAACAUCGCUAAA | 664 | 1 timesat | 20715NSP16 | | |
| GGUGUGCACAUGAACAUCGCUAAAU | 665 | 1 timesat | 20716NSP16 | | |
| GCCAGUAUUUAAAUACUUGCACAUU | 666 | 1 timesat | 20753NSP16 | | |
| CCAGUAUUUAAAUACUUGCACAUUA | 667 | 1 timesat | 20754NSP16 | | |
| GCCUGCCAAUAUGCGUGUUAUACAU | 668 | 1 timesat | 20784NSP16 | | |
| CCUGCCAAUAUGCGUGUUAUACAUU | 669 | 1 timesat | 20785NSP16 | UGCCAAUAUGCGUGUUAUACAUU | 1027 |
| CGUGUUAUACAUUUUGGCGCUGGUU | 670 | 1 timesat | 20797NSP16 | | |
| GCCAUUAUUAUAGAUAAUGAUUUAA | 671 | 1 timesat | 20878NSP16 | | |
| CCAUUAUUAUAGAUAAUGAUUUAAA | 672 | 1 timesat | 20879NSP16 | | |
| CGUGUCAGAUGCUGACAUAACUUUA | 673 | 1 timesat | 20910NSP16 | | |
| GCUGACAUAACUUUAUUUGGAGAUU | 674 | 1 timesat | 20920NSP16 | | |
| CCGACAUGUAUGAUCCUACUACUAA | 675 | 1 timesat | 20987NSP16 | GACAUGUAUGAUCCUACUACUAA | 1028 |
| CCUACUACUAAGAAUGUAACAGGUA | 676 | 1 timesat | 21001NSP16 | | |
| GGUAGUAAUGAGUCAAAGGCUUUAU | 677 | 1 timesat | 21022NSP16 | | |
| GCUUUAUUCUUUACUUACCUGUGUA | 678 | 1 timesat | 21040NSP16 | | |
| CCUGUGUAACCUCAUUAAUAAUAAU | 679 | 1 timesat | 21057NSP16 | | |
| GGUGGGUCUGUUGCUAUUAAAAUAA | 680 | 1 timesat | 21091NSP16 | | |
| GCUAUUAAAAUAACAGAACACUCUU | 681 | 1 timesat | 21103NSP16 | | |
| GGAGCGUUGAACUUUAUGAACUUAU | 682 | 1 timesat | 21128NSP16 | GAGCGUUGAACUUUAUGAACUUA | 1029 |
| GGGAAAAUUUGCUUGGUGGACUGUU | 683 | 1 timesat | 21153NSP16 | | |
| GGAAAAUUUGCUUGGUGGACUGUUU | 684 | 1 timesat | 21154NSP16 | | |
| GCAAAUGCAUCCUCAUCUGAAGGAU | 685 | 1 timesat | 21190NSP16 | | |
| GGUAUUAAUUACUUGGGUACUAUUA | 686 | 1 timesat | 21223NSP16 | | |
| GGGUACUAUUAAAGAAAAUAUAGAU | 687 | 1 timesat | 21237NSP16 | GGGUACUAUUAAAGAAAAUAUAG | 1030 |
| GGUGGUGCUAUGCACGCCAACUAUA | 688 | 1 timesat | 21262NSP16 | | |
| GGUGCUAUGCACGCCAACUAUAUAU | 689 | 1 timesat | 21265NSP16 | | |

TABLE 1-continued

Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21mer) | SEQ ID NO: |
|---|---|---|---|---|
| GCUAUGCACGCCAACUAUAUAUUUU | 690 | 1timesat 21268NSP16 | | |
| CGCCAACUAUAUAUUUUGGAGAAAU | 691 | 1timesat 21276NSP16 | | |
| GCCAACUAUAUAUUUUGGAGAAAUU | 692 | 1timesat 21277NSP16 | | |
| CCACUCCUAUGAAUCUGAGUACUUA | 693 | 1timesat 21302NSP16 | | |
| GGAGAGUCAAAUUAACGAACUCGUA | 694 | 1timesat 21390NSP16 | | |
| GGGUAAGUUACUUAUCCGUGACAAU | 695 | 1timesat 21432NSP16 | | |
| CCGUGACAAUGAUACACUCAGUGUU | 696 | 1timesat 21447NSP16 | | |

TABLE 1-continued

Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21

TABLE 1-continued

Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21mer) | SEQ ID NO: |
|---|---|---|---|---|
| GGUGUUCGACAGCAGCGCUUUGUUU | 759 | 1timesat 23324S protein | |

TABLE 1-continued

Predicted 25 mer siRNA targeting MERS NC019843.3 25mer blunt ended sequences

| SiRNA sequence | SEQ ID NO: | | Start Base | Protein Coded | 23 mer Sequences passing all metrics and BLAST search (allows for 2 base overhang on 21mer) | SEQ ID NO: |
|---|---|---|---|---|---|---|
| GGCUUCACUACAACUAAUGAAGCUU | 15 | 1 timesat | 24485 | S protein | GGCUUCACUACAACUAAUGAAGC | 1042 |
| GCUUCACUACAACUAAUGAAGCUUU | 794 | 1 timesat | 24486 | S protein | | |
| GCUAUCUAAUACUUUUGGUGCUAUU | 795 | 1 timesat | 24571 | S protein | | |
| GGCACAAUCCAAGCGUUCUGGAUUU | 796 | 1 timesat | 24778 | S protein | | |
| GCACAAUCCAAGCGUUCUGGAUUUU | 797 | 1 timesat | 24779 | S protein | | |
| CCCUAGCAACCACAUUGAGGUUGUU | 798 | 1 timesat | 24880 | S protein | | |
| CCUAGCAACCACAUUGAGGUUGUUU | 799 | 1 timesat | 24881 | S protein | | |
| CCACAUUGAGGUUGUUUCUGCUUAU | 800 | 1 timesat | 24889 | S protein | | |
| CCCUACUAAUUGUAUAGCCCCUGUU | 801 | 1 timesat | 24934 | S protein | | |
| CCUACUAAUUGUAUAGCCCCUGUUA | 802 | 1 timesat | 24935 | S protein | | |
| GCCCCUGUUAAUGGCUACUUUAUUA | 803 | 1 timesat | 24950 | S protein | | |
| CCCCUGUUAAUGGCUACUUUAUUAA | 16 | 1 timesat | 24951 | S protein | CCCCUGUUAAUGGCUACUUUAUU | 1043 |
| CCCUGUUAAUGGCUACUUUAUUAAA | 17 | 1 timesat | 24952 | S protein | CCCUGUUAAUGGCUACUUUAUUA | 1044 |
| CCUGUUAAUGGCUACUUUAUUAAAA | 804 | 1 timesat | 24953 | S protein | | |
| GGUCAUAUACUGGCUCGUCCUUCUA | 805 | 1 timesat | 25005 | S protein | | |
| CCUUAAUGAGUCUUACAUAGACCUU | 806 | 1 timesat | 25279 | S protein | | |
| GGCAAUUAUACUUAUUACAACAAAU | 807 | 1 timesat | 25313 | S protein | | |
| GGCCGUGGUACAUUUGGCUUGGUUU | 808 | 1 timesat | 25338 | S protein | | |
| GCUGGGCUUGUUGCCUUAGCUCUAU | 809 | 1 timesat | 25367 | S protein | | |
| GCACUGGUUGUGGCACAAACUGUAU | 810 | 1 timesat | 25413 | S protein | | |
| GGUUGUGGCACAAACUGUAUGGGAA | 811 | 1 timesat | 25418 | S protein | | |
| GGCACAAACUGUAUGGGAAAACUUA | 812 | 1 timesat | 25424 | S protein | | |
| GCACAAACUGUAUGGGAAAACUUAA | 813 | 1 timesat | 25425 | S protein | CACAAACUGUAUGGGAAAACUUA | 1045 |
| GGAAAACUUAAGUGUAAUCGUUGUU | 814 | 1 timesat | 25439 | S protein | | |
| CGUUGUUGUGAUAGAUACGAGGAAU | 815 | 1 timesat | 25457 | S protein | | |
| GCCGCAUAAGGUUCAUGUUCACUAA | 18 | 1 timesat | 25492 | S protein | GCCGCAUAAGGUUCAUGUUCACU | 1046 |
| CCGCAUAAGGUUCAUGUUCACUAAU | 816 | 1 timesat | 25493 | S protein | | |
| CGCAUAAGGUUCAUGUUCACUAAUU | 817 | 1 timesat | 25494 | S protein | | |
| GCAUAAGGUUCAUGUUCACUAAUUA | 818 | 1 timesat | 25495 | S protein | | |
| GGUUGCAUGCUUAGGGCUUGUAUUA | 819 | 1 timesat | 25639 | orf 3 | | |
| CCAAGCUGAUACAGCUGGUCUUUAU | 820 | 1 timesat | 25671 | orf 3 | | |
| GCUGAUACAGCUGGUCUUUAUACAA | 821 | 1 timesat | 25675 | orf 3 | | |
| CGAAUUGACGUCCCAUCUGCAGAAU | 822 | 1 timesat | 25705 | orf 3 | | |
| CCCUGUGCUGUGGAACUGUCAGCUA | 823 | 1 timesat | 25973 | orf4a | | |
| CCUGUGCUGUGGAACUGUCAGCUAU | 824 | 1 timesat | 25974 | orf4a | | |
| GCUGUGGAACUGUCAGCUAUCCUUU | 825 | 1 timesat | 25979 | orf4a | | |

TABLE 1-continued

Predicted 25 mer siRNA targeting MERS NC019843.3 25mer blunt ended sequences

| SiRNA sequence | SEQ ID NO: | | StartProtein Base Coded | 23 mer Sequences passing all metrics and BLAST search (allows for 2 base overhang on 21mer) | SEQ ID NO: |
|---|---|---|---|---|---|
| GCUAUCCUUUGCUGGUUAUACUGAA | 826 | 1 timesat | 25994orf4a | | |
| GCUGGUUAUACUGAAUCUGCUGUUA | 827 | 1 timesat | 26004orf4a | | |
| GGUUAUACUGAAUCUGCUGUUAAUU | 828 | 1 timesat | 26007orf4a | | |
| GCCAAACAGGACGCAGCUCAGCGAA | 829 | 1 timesat | 26046orf4a | | |
| CCAAACAGGACGCAGCUCAGCGAAU | 830 | 1 timesat | 26047orf4a | | |
| GGUUGCUACAUAAGGAUGGAGGAAU | 831 | 1 timesat | 26077orf4a | | |
| CGGCACUCAAGUUUAUUCGCGCAAA | 832 | 1 timesat | 26127orf4a | | |
| CCAACACACUAUGUCAGGGUUACAU | 833 | 1 timesat | 26248orf4b | | |
| GGGUUACAUUUUCAGACCCCAACAU | 834 | 1 timesat | 26264orf4b | | |
| GGUAUCUACGUUCGGGUCAUCAUUU | 835 | 1 timesat | 26291orf4b | | |
| GCCAACCUGUUUCUGAGUACCAUAU | 836 | 1 timesat | 26351orf4b | | |
| CCAACCUGUUUCUGAGUACCAUAUU | 837 | 1 timesat | 26352orf4b | | |
| CCAUAUUACUCUAGCUUUGCUAAAU | 838 | 1 timesat | 26370orf4b | | |
| GCUAAAUCUCACUGAUGAAGAUUUA | 839 | 1 timesat | 26388orf4b | | |
| CGCCUUGCUGCGCAAAACUCUUGUU | 840 | 1 timesat | 26475orf4b | | |
| GCUGCGCAAAACUCUUGUUCUUAAU | 841 | 1 timesat | 26481orf4b | CUGCGCAAAACUCUUGUUCUUAA | 1047 |
| CGCAAAACUCUUGUUCUUAAUGCAU | 842 | 1 timesat | 26485orf4b | CGCAAAACUCUUGUUCUUAAUGC | 1048 |
| GGAUUGGCUUCUCGUUCAGGGAUUU | 843 | 1 timesat | 26583orf4b | | |
| GCUUCUCGUUCAGGGAUUUUCCCUU | 844 | 1 timesat | 26589orf4b | | |
| CGUUCAGGGAUUUUCCCUUUACCAU | 845 | 1 timesat | 26595orf4b | | |
| CCCUUUACCAUAGUGGCCUCCCUUU | 846 | 1 timesat | 26609orf4b | | |
| CCUUUACCAUAGUGGCCUCCCUUUA | 847 | 1 timesat | 26610orf4b | | |
| CGCAAUUACAUCAUUACAAUGCCAU | 848 | 1 timesat | 26677orf4b | | |
| CCUCAACAAAUGUUUGUUACUCCUU | 849 | 1 timesat | 26716orf4b | | |
| CCAUACGGUCUUCCAAUCAGGGUAA | 850 | 1 timesat | 26759orf4b | | |
| GGUAAUAAACAAAUUGUUCAUUCUU | 851 | 1 timesat | 26779orf4b | | |
| GGCUUUCUCGGCGUCUUUAUUUAAA | 852 | 1 timesat | 26841orf5 | GGCUUUCUCGGCGUCUUUAUUUA | 1049 |
| CCUAUUAUUACUGCUACGUCAAGAU | 853 | 1 timesat | 26991orf5 | | |
| CCUUGUUCUGUAUAACUUUUUAUUA | 854 | 1 timesat | 27057orf5 | UUGUUCUGUAUAACUUUUUAUUA | 1050 |
| GGUGUACAUUAUCCAACUGGAAGUU | 855 | 1 timesat | 27100orf5 | | |
| CCUCAUAAUACUUUGGUUUGUAGAU | 856 | 1 timesat | 27147orf5 | | |
| CCAAACCAUUAUUUAUUAGAAACUU | 857 | 1 timesat | 27284orf5 | | |
| GCGUUGCAGCUGUUCUCGUUGUUUU | 858 | 1 timesat | 27315orf5 | | |
| CGUUGCAGCUGUUCUCGUUGUUUUU | 859 | 1 timesat | 27316orf5 | | |
| GCAGCUGUUCUCGUUGUUUUUAUUU | 860 | 1 timesat | 27320orf5 | | |

TABLE 1-continued

Predicted 25 mer siRNA targeting
MERS NC019843.3
25mer blunt

TABLE 1-continued

Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21mer) | SEQ ID NO: |
|

TABLE 1-continued

Predicted 25 mer siRNA targeting
MERS NC019843.3
25mer blunt ended sequences

| SiRNA sequence | SEQ ID NO: | StartProtein Base Coded | 23 mer Sequences passing all metrics and BLAST search (allows for 2 base overhang on 21mer) | SEQ ID NO: |
|---|---|---|---|---|
| CGCAGCCAAAAGUAAUCACUAAGAA | 932 | 1 times at 29262N | | |
| GCGCCACAAGCGCACUUCCACCAAA | 933 | 1 times at 29314N | | |
| CGCCACAAGCGCACUUCCACCAAAA | 934 | 1 times at 29315N | | |
| GCACUUCCACCAAAAGUUUCAACAU | 935 | 1 times at 29325N | | |
| CGCGGACCAGGAGACCUCCAGGGAA | 936 | 1 times at 29369N | | |
| GCGGACCAGGAGACCUCCAGGGAAA | 937 | 1 times at 29370N | | |
| CCUCCAGGGAAACUUUGGUGAUCUU | 938 | 1 times at 29383N | | |
| CCAGGGAAACUUUGGUGAUCUUCAA | 939 | 1 times at 29386N | | |
| CCCCAAAUUGCUGAGCUUGCUCCUA | 940 | 1 times at 29444N | | |
| GCUUGCUCCUACAGCCAGUGCUUUU | 941 | 1 times at 29458N | | |
| CCUACAGCCAGUGCUUUUAUGGGUA | 942 | 1 times at 29465N | | |
| GCUUUUAUGGGUAUGUCGCAAUUUA | 943 | 1 times at 29477N | | |
| CGCAAUUUAAACUUACCCAUCAGAA | 944 | 1 times at 29493N | | |
| GCAACCCUGUGUACUUCCUUCGGUA | 945 | 1 times at 29532N | | |
| CCUUCGGUACAGUGGAGCCAUUAAA | 946 | 1 times at 29548N | | |
| GGUUGGAGCUUCUUGAGCAAAAUAU | 947 | 1 times at 29604N | | |
| GGAGCUUCUUGAGCAAAAUAUUGAU | 948 | 1 times at 29608N | GAGCUUCUUGAGCAAAAUAUUGA | 1056 |
| GGAAAAGAAACAAAAGGCACCAAAA | 949 | 1 times at 29656N | | |
| CGUCCAAGUGUUCAGCCUGGUCCAA | 950 | 1 times at 29759N | | |
| CCAAUGAUUGAUGUUAACACUGAUU | 951 | 1 times at 29780N | | |

TABLE 2

Predicted 25 mer siRNA targeting
MERS NC019843.3
25mer blunt ended sequences

| SiRNA sequence | SEQ ID NO: | StartProtein Base Name | 23 mer Sequences passing all metrics and BLAST search | SEQ ID NO: |
|---|---|---|---|---|
| CCCAGAAUCUGCUUAAGAAGUUGAU | 32 | 1 times at 825 NSP1 | CCCAGAAUCUGCUUAAGAAGUUG | 952 |
| GCCCAUUCAUGGAUAAUGCUAUUAA | 64 | 1 times at 1884 NSP2 | GCCCAUUCAUGGAUAAUGCUAUU | 953 |
| CCCAUUCAUGGAUAAUGCUAUUAAU | 65 | 1 times at 1885 NSP2 | CCCAUUCAUGGAUAAUGCUAUUA | 954 |
| CGCCAUUACUGCACCUUAUGUAGUU | 67 | 1 times at 1936 NSP2 | CGCCAUUACUGCACCUUAUGUAG | 955 |
| GGCGACUUUAUGUCUACAAUUAUUA | 71 | 1 times at 2186 NSP2 | GGCGACUUUAUGUCUACAAUUAU | 957 |
| GCUGUGUCUUUUGAUUAUCUUAUUA | 111 | 1 times at 4007 NSP3 | CUGUGUCUUUUGAUUAUCUUAUU | 960 |
| CGCAAUACGUAAAGCUAAAGAUUAU | 1 | 1 times at 4144 NSP3 | CGCAAUACGUAAAGCUAAAGAUU | 961 |
| GGGUGUUGAUUAUACUAAGAAGUUU | 2 | 1 times at 4228 NSP3 | GGGUGUUGAUUAUACUAAGAAGU | 962 |
| GGACACUUUAGAUGAUAUCUUACAA | 120 | 1 times at 4294 NSP3 | GACACUUUAGAUGAUAUCUUACA | 963 |
| CGCACUAAUGGUGGUUACAAUUCUU | 132 | 1 times at 4517 NSP3 | CGCACUAAUGGUGGUUACAAUUC | 964 |

TABLE 2-continued

Predicted 25 mer siRNA targeting MERS NC019843.3 25mer blunt ended sequences

| SiRNA sequence | SEQ ID NO: | | StartProtein Base Name | 23 mer Sequences passing all metrics and BLAST search | SEQ ID NO: |
|---|---|---|---|---|---|
| CCUACUUUCUUACACAGAUUCUAUU | 138 | 1 times at | 4949NSP3 | UACUUUCUUACACAGAUUCUAUU | 965 |
| CCGACCUAUCUGCUUUCUAUGUUAA | 160 | 1 times at | 5733NSP3 | GACCUAUCUGCUUUCUAUGUUAA | 966 |
| GGUGAUGCUAUUAGUUUGAGUUUUA | 172 | 1 times at | 5870NSP3 | GUGAUGCUAUUAGUUUGAGUUUU | 967 |
| GCAUCUUAUGAUACUAAUCUUAAUA | 176 | 1 times at | 6062NSP3 | AUCUUAUGAUACUAAUCUUAAUA | 968 |
| GCCCCCAUUGAACUCGAAAAUAAAU | 178 | 1 times at | 6125NSP3 | CCCCAUUGAACUCGAAAAUAAAU | 969 |
| CCCCCAUUGAACUCGAAAAUAAAUU | 179 | 1 times at | 6126NSP3 | CCCAUUGAACUCGAAAAUAAAUU | 970 |
| CCUAAGUAUCAAGUCAUUGUCUUAA | 184 | 1 times at | 6353NSP3 | CCCUAAGUAUCAAGUCAUUGUCU | 971 |
| GGCUUCAUUUUAUUUCAAAGAAUUU | 4 | 1 times at | 6487NSP3 | GGCUUCAUUUUAUUUCAAAGAAU | 972 |
| CCACUAGCUUACUUUAGUGAUUCAA | 194 | 1 times at | 6638NSP3 | CACUAGCUUACUUUAGUGAUUCA | 973 |
| CCCAAGGUUUGAAAAAGUUCUACAA | 203 | 1 times at | 6906NSP3 | CCCAAGGUUUGAAAAAGUUCUAC | 974 |
| CCAAGGUUUGAAAAAGUUCUACAAA | 204 | 1 times at | 6907NSP3 | AAGGUUUGAAAAAGUUCUACAAA | 975 |
| GGCAGGUACAUUGCAUUAUUUCUUU | 213 | 1 times at | 7207NSP3 | CAGGUACAUUGCAUUAUUUCUUU | 976 |
| GCGCUUUUACAAAUCUAGAUAAGUU | 5 | 1 times at | 7740NSP3 | GCGCUUUUACAAAUCUAGAUAAG | 977 |
| CGGCUUCAGUUAACCAAAUUGUCUU | 242 | 1 times at | 8286NSP3 | GGCUUCAGUUAACCAAAUUGUCU | 978 |
| CGCAUUGCAUGCCGUAAGUGUAAUU | 6 | 1 times at | 8387NSP3 | CGCAUUGCAUGCCGUAAGUGUAA | 979 |
| CCUCAAAGCUACGCGCUAAUGAUAA | 247 | 1 times at | 8430NSP3 | CUCAAAGCUACGCGCUAAUGAUA | 980 |
| CCGCAUCUUGGACUUUAAAGUUCUU | 251 | 1 times at | 8638NSP4 | CCGCAUCUUGGACUUUAAAGUUC | 981 |
| GCUCUUCUAUUAUAUUAAUAAAGUA | 279 | 1 times at | 9406NSP4 | CUCUUCUAUUAUAUUAAUAAAGU | 982 |
| GCUGCCUCUAAUAUCUUUGUUAUUA | 285 | 1 times at | 9767NSP4 | UGCCUCUAAUAUCUUUGUUAUUA | 983 |
| CCUCUAAUAUCUUUGUUAUUAACAA | 286 | 1 times at | 9771NSP4 | CUCUAAUAUCUUUGUUAUUAACA | 984 |
| GCAGCUCUUAGAAACUCUUUAACUA | 287 | 1 times at | 9806NSP4 | CAGCUCUUAGAAACUCUUUAACU | 985 |
| CGGAAGUGAAGAUGAUACUUUUAUU | 333 | 1 times at | 11556NSP6 | CGGAAGUGAAGAUGAUACUUUUA | 986 |
| GGAAGUGAAGAUGAUACUUUUAUUA | 334 | 1 times at | 11557NSP6 | AAGUGAAGAUGAUACUUUUAUUA | 987 |
| GGCUAUGACUUCUAUGUAUAAGCAA | 358 | 1 times at | 12259NSP8 | GGCUAUGACUUCUAUGUAUAAGC | 988 |
| CCCCAAUCUAAAGAUUCCAAUUUUU | 395 | 1 times at | 13403NSP10 | CCCCAAUCUAAAGAUUCCAAUUU | 990 |
| CCCAAUCUAAAGAUUCCAAUUUUUU | 396 | 1 times at | 13404NSP10 | CCCAAUCUAAAGAUUCCAAUUUU | 991 |
| GCUGUGAUGUUACCUACUUUGAAAA | 415 | 1 times at | 13862NSP12 | CUGUGAUGUUACCUACUUUGAAA | 992 |
| CCCAGUGUUAUUGGUGUUUAUCAUA | 7 | 1 times at | 13915NSP12 | CCCAGUGUUAUUGGUGUUUAUCA | 993 |
| CCAGUGUUAUUGGUGUUUAUCAUAA | 417 | 1 times at | 13916NSP12 | CAGUGUUAUUGGUGUUUAUCAUA | 994 |
| GGUACAACUCUUUGAGAAGUACUUU | 433 | 1 times at | 14247NSP12 | UACAACUCUUUGAGAAGUACUUU | 995 |
| CCUCCUCUAACGCUUUUCUUGAUUU | 446 | 1 times at | 14558NSP12 | CUCCUCUAACGCUUUUCUUGAUU | 996 |
| CCUACUAUGUGUGACAUCAAACAAA | 456 | 1 times at | 14791NSP12 | UACUAUGUGUGACAUCAAACAAA | 997 |
| GCUGGGAUUUCAUGCUUAAAACAUU | 475 | 1 times at | 15200NSP12 | UGGGAUUUCAUGCUUAAAACAUU | 998 |
| GGGAUUUCAUGCUUAAAACAUUGUA | 8 | 1 times at | 15203NSP12 | GGGAUUUCAUGCUUAAAACAUUG | 999 |
| CCACUGCAUAUGCCAAUAGUGUCUU | 486 | 1 times at | 15467NSP12 | CACUGCAUAUGCCAAUAGUGUCU | 1000 |
| GGGUGCUAAUGGCAACAAGAUUGUU | 9 | 1 times at | 15534NSP12 | GGGUGCUAAUGGCAACAAGAUUG | 1001 |
| CCCCAAAUUUGUUGAUAAAUACUAU | 10 | 1 times at | 15624NSP12 | CCCCAAAUUUGUUGAUAAAUACU | 1002 |

TABLE 2-continued

Predicted 25 mer siRNA targeting
MERS NC019843.3
25mer blunt ended sequences

| SiRNA sequence | SEQ ID NO: | Start Base | Protein Name | 23 mer Sequences passing all metrics and BLAST search | SEQ ID NO: |
|---|---|---|---|---|---|
| CGGUUGCUUUGUAGAUGAUAUCGUU | 11 | 1 times at 15930 | NSP12 | CGGUUGCUUUGUAGAUGAUAUCG | 1003 |
| GGUUGCUUUGUAGAUGAUAUCGUUA | 512 | 1 times at 15931 | NSP12 | UUGCUUUGUAGAUGAUAUCGUUA | 1004 |
| CCCUCUCACAAAGCAUGAAGAUAUA | 515 | 1 times at 16011 | NSP12 | CUCUCACAAAGCAUGAAGAUAUA | 1005 |
| GGUCUACUUACAGUAUAUAGAAAAA | 519 | 1 times at 16056 | NSP12 | GUCUACUUACAGUAUAUAGAAAA | 1006 |
| CCACCACUCAAUCGUAAUUAUGUUU | 530 | 1 times at 16726 | NSP13 | ACCACUCAAUCGUAAUUAUGUUU | 1007 |
| CCUACAAGUCUAGUACAACGUAUAA | 536 | 1 times at 16835 | NSP13 | UACAAGUCUAGUACAACGUAUAA | 1008 |
| GCACUAAUUAUGAUCUUUCAAUUAU | 549 | 1 times at 17342 | NSP13 | CACUAAUUAUGAUCUUUCAAUUA | 1009 |
| GCAUGGAGUAAGGCAGUCUUUAUUU | 564 | 1 times at 17719 | NSP13 | AUGGAGUAAGGCAGUCUUUAUUU | 1010 |
| GCACAUGCUAACAACAUUAACAGAU | 566 | 1 times at 17863 | NSP13 | CACAUGCUAACAACAUUAACAGA | 1011 |
| GCCCAAAAAGGUAUUCUUUGUGUUA | 568 | 1 times at 17908 | NSP13 | GCCCAAAAAGGUAUUCUUUGUGU | 1012 |
| GCACUCUUUGAGUCCUUAGAGUUUA | 571 | 1 times at 17944 | NSP13 | CACUCUUUGAGUCCUUAGAGUUU | 1013 |
| CCUGCGGUUAUGAUUAUGUCUACAA | 598 | 1 times at 18689 | NSP14 | CUGCGGUUAUGAUUAUGUCUACA | 1014 |
| CGGUUCAUUUGACAAAGUCUAUGAU | 607 | 1 times at 18969 | NSP14 | CGGUUCAUUUGACAAAGUCUAUG | 1015 |
| GGUUCAUUUGACAAAGUCUAUGAUA | 608 | 1 times at 18970 | NSP14 | UUCAUUUGACAAAGUCUAUGAUA | 1016 |
| GGUAGUAUGAUAGAGGAUAUUGAUU | 615 | 1 times at 19360 | NSP14 | UAGUAUGAUAGAGGAUAUUGAUU | 1017 |
| GGUGUUAUAAGACCUUUGAUAUUUA | 618 | 1 times at 19517 | NSP14 | GUGUUAUAAGACCUUUGAUAUUU | 1018 |
| GGGAUUAUGAACGUAGCAAUAUUUA | 629 | 1 times at 19829 | NSP15 | GGGAUUAUGAACGUAGCAAUAUU | 1019 |
| GCCAUCUUUAUUUCUGAUAGAAAAA | 634 | 1 times at 19972 | NSP15 | GCCAUCUUUAUUUCUGAUAGAAA | 1020 |
| CCAUCUUUAUUUCUGAUAGAAAAAU | 635 | 1 times at 19973 | NSP15 | AUCUUUAUUUCUGAUAGAAAAAU | 1021 |
| CCGUGAUAGUGAUGUUGUUAAACAA | 637 | 1 times at 20055 | NSP15 | CCGUGAUAGUGAUGUUGUUAAAC | 1022 |
| GGUCUUCACUUGCUUAUUGGUUUAU | 643 | 1 times at 20302 | NSP15 | GUCUUCACUUGCUUAUUGGUUUA | 1023 |
| GCUCAACUAUUCAUAACUAUUUUAU | 648 | 1 times at 20378 | NSP15 | CUCAACUAUUCAUAACUAUUUUA | 1024 |
| GGUUCCUAUUGACUUAACAAUGAUU | 657 | 1 times at 20520 | NSP15 | UUCCUAUUGACUUAACAAUGAUU | 1025 |
| CCCUCUUUAAAGUUCAAAAUGUAAA | 661 | 1 times at 20639 | NSP16 | CUCUUUAAAGUUCAAAAUGUAAA | 1026 |
| CCUGCCAAUAUGCGUGUUAUACAUU | 669 | 1 times at 20785 | NSP16 | UGCCAAUAUGCGUGUUAUACAUU | 1027 |
| CCGACAUGUAUGAUCCUACUACUAA | 675 | 1 times at 20987 | NSP16 | GACAUGUAUGAUCCUACUACUAA | 1028 |
| GGAGCGUUGAACUUUAUGAACUUAU | 682 | 1 times at 21128 | NSP16 | GAGCGUUGAACUUUAUGAACUUA | 1029 |
| GGGUACUAUUAAAGAAAAUAUAGAU | 687 | 1 times at 21237 | NSP16 | GGGUACUAUUAAAGAAAAUAUAG | 1030 |
| GGCCGUACAUAUUCUAACAUAACUA | 12 | 1 times at 21635 | S protein | GGCCGUACAUAUUCUAACAUAAC | 1031 |
| GCCGUACAUAUUCUAACAUAACUAU | 700 | 1 times at 21636 | S protein | GCCGUACAUAUUCUAACAUAACU | 1032 |
| GGGAGACCAUGGUGAUAUGUAUGUU | 703 | 1 times at 21688 | S protein | CACUUUACUUAGAGCUUUUUAUU | 1033 |
| GCACCUUUAUGUACACUUAUAACAU | 717 | 1 times at 22164 | S protein | CACCUUUAUGUACACUUAUAACA | 1034 |
| CCGAAGAUGAGAUUUUAGAGUGGUU | 13 | 1 times at 22191 | S protein | CCGAAGAUGAGAUUUUAGAGUGG | 1035 |
| GGUCCAAUAUCCCAGUUUAAUUAUA | 741 | 1 times at 22838 | S protein | UGGUCCAAUAUCCCAGUUUAAUU | 1036 |
| CCCAGUUUAAUUAUAAACAGUCCUU | 14 | 1 times at 22848 | S protein | CCCAGUUUAAUUAUAAACAGUCC | 1037 |
| GGUUGAUCAACUUAAUAGUAGUUAU | 765 | 1 times at 23761 | S protein | UUGAUCAACUUAAUAGUAGUUAU | 1038 |

TABLE 2-continued

Predicted 25 mer siRNA targeting
MERS NC019843.3
25mer blunt ended sequences

| SiRNA sequence | SEQ ID NO: | Start Base | Protein Name | 23 mer Sequences passing all metrics and BLAST search | SEQ ID NO: |
|---|---|---|---|---|---|
| GCCAGGAUGAUUCUGUACGUAAUUU | 770 | 1 times at 23976 | S protein | CAGGAUGAUUCUGUACGUAAUUU | 1039 |
| GGAUGAUUCUGUACGUAAUUUGUUU | 771 | 1 times at 23980 | S protein | AUGAUUCUGUACGUAAUUUGUUU | 1040 |
| CCAGGUUUUGGAGGUGACUUUAAUU | 774 | 1 times at 24041 | S protein | CAGGUUUUGGAGGUGACUUUAAU | 1041 |
| GGCUUCACUACAACUAAUGAAGCUU | 15 | 1 times at 24485 | S protein | GGCUUCACUACAACUAAUGAAGC | 1042 |
| CCCCUGUUAAUGGCUACUUUAUUAA | 16 | 1 times at 24951 | S protein | CCCCUGUUAAUGGCUACUUUAUU | 1043 |
| CCCUGUUAAUGGCUACUUUAUUAAA | 17 | 1 times at 24952 | S protein | CCCUGUUAAUGGCUACUUUAUUA | 1044 |
| GCACAAACUGUAUGGGAAAACUUAA | 813 | 1 times at 25425 | S protein | CACAAACUGUAUGGGAAAACUUA | 1045 |
| GCCGCAUAAGGUUCAUGUUCACUAA | 18 | 1 times at 25492 | S protein | GCCGCAUAAGGUUCAUGUUCACU | 1046 |
| GCUGCGCAAAACUCUUGUUCUUAAU | 841 | 1 times at 26481 | orf4b | CUGCGCAAAACUCUUGUUCUUAA | 1047 |
| CGCAAAACUCUUGUUCUUAAUGCAU | 842 | 1 times at 26485 | orf4b | CGCAAAACUCUUGUUCUUAAUGC | 1048 |
| GGCUUUCUCGGCGUCUUUAUUUAAA | 852 | 1 times at 26841 | orf5 | GGCUUUCUCGGCGUCUUUAUUUA | 1049 |
| CCUUGUUCUGUAUAACUUUUUAUUA | 854 | 1 times at 27057 | orf5 | UUGUUCUGUAUAACUUUUUAUUA | 1050 |
| GGACAUAUGGAAAACGAACUAUGUU | 873 | 1 times at 27569 | | GACAUAUGGAAAACGAACUAUGU | 1051 |
| GGCAUUGUAGCAGCUGUUUCAGCUA | 884 | 1 times at 28092 | M | GGCAUUGUAGCAGCUGUUUCAGC | 1052 |
| GCCUAUUACGGCGGAUAUUGAACUU | 903 | 1 times at 28469 | M | GCCUAUUACGGCGGAUAUUGAAC | 1053 |
| CCGGUACUAAGCUUCCUAAAAACUU | 923 | 1 times at 29019 | N | CCGGUACUAAGCUUCCUAAAAAC | 1054 |

TABLE 3

Predicted 25 mer siRNA targeting
25mer blunt ended sequences

| SiRNA sequence | SEQ ID NO: | Start Base | Protein Name | 23 mer Sequences passing all metrics and BLAST search | SEQ ID NO: |
|---|---|---|---|---|---|
| CCCAGAAUCUGCUUAAGAAGUUGAU | 32 | 1 times at | 825 NSP1 | CCCAGAAUCUGCUUAAGAAGUUG | 952 |
| GCCCAUUCAUGGAUAAUGCUAUUAA | 64 | 1 times at | 1884 NSP2 | GCCCAUUCAUGGAUAAUGCUAUU | 953 |
| CCCAUUCAUGGAUAAUGCUAUUAAU | 65 | 1 times at | 1885 NSP2 | CCCAUUCAUGGAUAAUGCUAUUA | 954 |
| CGCCAUUACUGCACCUUAUGUAGUU | 67 | 1 times at | 1936 NSP2 | CGCCAUUACUGCACCUUAUGUAG | 955 |
| GGCGACUUUAUGUCUACAAUUAUUA | 71 | 1 times at | 2186 NSP2 | GGCGACUUUAUGUCUACAAUUAU | 957 |
| CGCAAUACGUAAAGCUAAAGAUUAU | 1 | 1 times at | 4144 NSP3 | CGCAAUACGUAAAGCUAAAGAUU | 961 |
| GGGUGUUGAUUAUACUAAGAAGUUU | 2 | 1 times at | 4228 NSP3 | GGGUGUUGAUUAUACUAAGAAGU | 962 |
| CGCACUAAUGGUGGUUACAAUUCUU | 132 | 1 times at | 4517 NSP3 | CGCACUAAUGGUGGUUACAAUUC | 964 |
| GGCUUCAUUUUAUUUCAAAGAAUUU | 4 | 1 times at | 6487 NSP3 | GGCUUCAUUUUAUUUCAAAGAAU | 972 |
| GCGCUUUUACAAAUCUAGAUAAGUU | 5 | 1 times at | 7740 NSP3 | GCGCUUUUACAAAUCUAGAUAAG | 977 |
| CGCAUUGCAUGCCGUAAGUGUAAUU | 6 | 1 times at | 8387 NSP3 | CGCAUUGCAUGCCGUAAGUGUAA | 979 |
| CCGCAUCUUGGACUUUAAAGUUCUU | 251 | 1 times at | 8638 NSP4 | CCGCAUCUUGGACUUUAAAGUUC | 981 |
| CGGAAGUGAAGAUGAUACUUUUAUU | 333 | 1 times at | 11556 NSP6 | CGGAAGUGAAGAUGAUACUUUUA | 986 |
| GGCUAUGACUUCUAUGUAUAAGCAA | 358 | 1 times at | 12259 NSP8 | GGCUAUGACUUCUAUGUAUAAGC | 988 |
| CCCCAAUCUAAAGAUUCCAAUUUUU | 395 | 1 times at | 13403 NSP10 | CCCCAAUCUAAAGAUUCCAAUUU | 990 |

TABLE 3-continued

Predicted 25 mer siRNA targeting 25mer blunt ended sequences

| SiRNA sequence | SEQ ID NO: | Start times | Protein Base Name | 23 mer Sequences passing all metrics and BLAST search | SEQ ID NO: |
|---|---|---|---|---|---|
| CCCAAUCUAAAGAUUCCAAUUUUUU | 936 | 1 times at 13404 | NSP10 | CCCAAUCUAAAGAUUCCAAUUUU | 991 |
| CCCAGUGUUAUUGGUGUUUAUCAUA | 7 | 1 times at 13915 | NSP12 | CCCAGUGUUAUUGGUGUUUAUCA | 993 |
| GGGAUUUCAUGCUUAAAACAUUGUA | 8 | 1 times at 15203 | NSP12 | GGGAUUUCAUGCUUAAAACAUUG | 999 |
| GGGUGCUAAUGGCAACAAGAUUGUU | 9 | 1 times at 15534 | NSP12 | GGGUGCUAAUGGCAACAAGAUUG | 1001 |
| CCCCAAAUUUGUUGAUAAAUACUAU | 10 | 1 times at 15624 | NSP12 | CCCCAAAUUUGUUGAUAAAUACU | 1002 |
| CGGUUGCUUUGUAGAUGAUAUCGUU | 11 | 1 times at 15930 | NSP12 | CGGUUGCUUUGUAGAUGAUAUCG | 1003 |
| GCCCAAAAAGGUAUUCUUUGUGUUA | 568 | 1 times at 17908 | NSP13 | GCCCAAAAAGGUAUUCUUUGUGU | 1012 |
| CGGUUCAUUUGACAAAGUCUAUGAU | 607 | 1 times at 18969 | NSP14 | CGGUUCAUUUGACAAAGUCUAUG | 1015 |
| GGGAUUAUGAACGUAGCAAUAUUUA | 629 | 1 times at 19829 | NSP15 | GGGAUUAUGAACGUAGCAAUAUU | 1019 |
| GCCAUCUUUAUUUCUGAUAGAAAAA | 634 | 1 times at 19972 | NSP15 | GCCAUCUUUAUUUCUGAUAGAAA | 1020 |
| CCGUGAUAGUGAUGUUGUUAAACAA | 637 | 1 times at 20055 | NSP15 | CCGUGAUAGUGAUGUUGUUAAAC | 1022 |
| GGGUACUAUUAAAGAAAAUAUAGAU | 687 | 1 times at 21237 | NSP16 | GGGUACUAUUAAAGAAAAUAUAG | 1030 |
| GGCCGUACAUAUUCUAACAUAACUA | 12 | 1 times at 21635 | S protein | GGCCGUACAUAUUCUAACAUAAC | 1031 |
| GCCGUACAUAUUCUAACAUAACUAU | 700 | 1 times at 21636 | S protein | GCCGUACAUAUUCUAACAUAACU | 1032 |
| CCGAAGAUGAGAUUUUAGAGUGGUU | 13 | 1 times at 22191 | S protein | CCGAAGAUGAGAUUUUAGAGUGG | 1035 |
| CCCAGUUUAAUUAUAAACAGUCCUU | 14 | 1 times at 22848 | S protein | CCCAGUUUAAUUAUAAACAGUCC | 1037 |
| GGCUUCACUACAACUAAUGAAGCUU | 15 | 1 times at 24485 | S protein | GGCUUCACUACAACUAAUGAAGC | 1042 |
| CCCCUGUUAAUGGCUACUUUAUUAA | 16 | 1 times at 24951 | S protein | CCCCUGUUAAUGGCUACUUUAUU | 1043 |
| CCCUGUUAAUGGCUACUUUAUUAAA | 17 | 1 times at 24952 | S protein | CCCUGUUAAUGGCUACUUUAUUA | 1044 |
| GCCGCAUAAGGUUCAUGUUCACUAA | 18 | 1 times at 25492 | S protein | GCCGCAUAAGGUUCAUGUUCACU | 1046 |
| CGCAAAACUCUUGUUCUUAAUGCAU | 842 | 1 times at 26485 | orf4b | CGCAAAACUCUUGUUCUUAAUGC | 1048 |
| GGCUUUCUCGGCGUCUUUAUUUAAA | 852 | 1 times at 26841 | orf5 | GGCUUUCUCGGCGUCUUUAUUUA | 1049 |
| GGCAUUGUAGCAGCUGUUUCAGCUA | 884 | 1 times at 28092 | M | GGCAUUGUAGCAGCUGUUUCAGC | 1052 |
| GCCUAUUACGGCGGAUAUUGAACUU | 903 | 1 times at 28469 | M | GCCUAUUACGGCGGAUAUUGAAC | 1053 |
| CCGGUACUAAGCUUCCUAAAAACUU | 923 | 1 times at 29019 | N | CCGGUACUAAGCUUCCUAAAAAC | 1054 |

TABLE 4

Characterization indexes of five SLiC species and five SLiC-siRNA nanoparticles, including particle sizes, poly-dispersity index (PDI) and Zeta-potential.

| Names | Diameter (nm) | PDI | Zeta-potential (mV0) | Names | Diameter (nm) | PDI | Zeta-potential (mV0) |
|---|---|---|---|---|---|---|---|
| SLiC1 | 479.3 ± 55.1 | 0.66 ± 0.13 | 61.1 ± 1.27 | SLiC3 | 213.8 ± 20.4 | 0.25 ± 0.14 | 43.1 ± 1.72 |
| SLiC2 | 196.9 ± 25.6 | 0.41 ± 0.24 | 42.3 ± 1.85 | SLiC4 | 341.2 ± 33.8 | 0.71 ± 0.08 | 46.1 ± 1.35 |

TABLE 4-continued

Characterization indexes of five SLiC species and five SLiC-siRNA nanoparticles, including particle sizes, poly-dispersity index (PDI) and Zeta-potential.

| Names | Diameter (nm) | PDI | Zeta-potential (mV0) |
|---|---|---|---|
| SLiC5 | 1091 ± 34.2 | 0.87 ± 0.09 | 61.5 ± 1.14 |
| SLiC1 (siRNA) | 174.1 ± 11.1 | 0.39 ± 0.03 | 42.3 ± 1.15 |
| SLiC2 (siRNA) | 115.5 ± 15.6 | 0.20 ± 0.04 | 34.4 ± 1.85 |
| SLiC3 (siRNA) | 169.6 ± 10.4 | 0.22 ± 0.04 | 38.2 ± 0.80 |
| SLiC4 (siRNA) | 154.7 ± 13.8 | 0.35 ± 0.07 | 40.6 ± 1.21 |
| SLiC5 (siRNA) | 182.6 ± 14.1 | 0.38 ± 0.09 | 44.4 ± 1.23 |

What is claimed is:

1. A pharmaceutical composition comprising at least two different siRNA molecules that target the MERS-CoV Spike protein, and a pharmaceutically acceptable carrier comprising a polymeric nanoparticle or a liposomal nanoparticle, wherein the siRNA molecules are selected from the group consisting of:

```
                                            (SEQ ID NO: 12)
MSP1: GGCCGUACAUAUUCUAACAUAACUA, (SEQ ID NO: 700)
MSP2: GCCGUACAUAUUCUAACAUAACUAU, (SEQ ID NO: 13)
MSP3: CCGAAGAUGAGAUUUUAGAGUGGUU, (SEQ ID NO: 14)
MSP4: CCCAGUUUAAUUAUAAACAGUCCUU, (SEQ ID NO: 15)
MSP5: GGCUUCACUACAACUAAUGAAGCUU, (SEQ ID NO: 16)
MSP6: CCCCUGUUAAUGGCUACUUUAUUAA, (SEQ ID NO: 17)
MSP7: CCCUGUUAAUGGCUACUUUAUUAAA,
and (SEQ ID NO: 18)
MSP8: GCCGCAUAAGGUUCAUGUUCACUAA.
```

2. A pharmaceutical composition comprising at least two different siRNA molecules that target the genome of a MERS-CoV, wherein a first siRNA molecule comprises MRR2: GGGAUUUCAUGCUUAAAACAUUGUA (SEQ ID NO: 20) and a second siRNA molecule comprises MSP2: GCCGUACAUAUUCUAACAUAACUAU (SEQ ID NO: 700).

3. A pharmaceutical composition comprising a siRNA cocktail, MSTRS1, wherein a first siRNA molecule comprises MRR1: CCCAGUGUUAUUGGUGUUUAUCAUA (SEQ ID NO: 21) and a second siRNA molecule comprises MSP1: GGCCGUACAUAUUCUAACAUAACUA (SEQ ID NO: 12) and a pharmaceutically acceptable carrier comprising a polymeric nanoparticle or a liposomal nanoparticle.

4. A pharmaceutical composition comprising a siRNA cocktail, MSTPRS1, wherein a first siRNA molecule comprises MPL1: CGCAAUACGUAAAGCUAAAGAUAU (SEQ ID NO: 22), a second siRNA molecule comprises MRR1: CCCAGUGUUAUUGGUGUUUAUCAUA (SEQ ID NO: 7), and a third siRNA molecule comprises MSP1: GGCCGUACAUAUUCUAACAUAACUA (SEQ ID NO:12) and a pharmaceutically acceptable carrier comprising a polymeric nanoparticle or a liposomal nanoparticle.

5. The composition of claim 1, wherein the polymeric nanoparticle carrier comprises a Histidine-Lysine co-polymer (HKP).

6. The composition of claim 1, wherein the liposomal nanoparticle carrier comprises a Spermine-Lipid Conjugate (SLiC) and cholesterol.

7. A method of treating a mammal with a MERS infection comprising administering to said mammal a pharmaceutically effective amount of the composition of claim 1.

8. The method of claim 7, wherein the mammal is a human.

9. An siRNA molecule that targets a conserved region of the genome of a MERS-CoV wherein the molecule is selected from the group consisting of the molecules of SEQ ID NOs 12, 1031, 700, 1032, 703, 1033, 717, 1034, 13, 1035, 741, 1036, 14, 1037, 765, 1038, 770, 1039, 771, 1040, 774, 1041, 15, 1042, 16, 1043, 17, 1044, 813, 1045, 18, and 1046.

10. An siRNA molecule that targets a conserved region of the genome of a MERS-CoV selected from the group consisting of:

```
                                            (SEQ ID NO: 12)
MSP1: GGCCGUACAUAUUCUAACAUAACUA, (SEQ ID NO: 700)
MSP2: GCCGUACAUAUUCUAACAUAACUAU, (SEQ ID NO: 13)
MSP3: CCGAAGAUGAGAUUUUAGAGUGGUU, (SEQ ID NO: 14)
MSP4: CCCAGUUUAAUUAUAAACAGUCCUU, (SEQ ID NO: 15)
MSP5: GGCUUCACUACAACUAAUGAAGCUU, (SEQ ID NO: 16)
MSP6: CCCCUGUUAAUGGCUACUUUAUUAA, (SEQ ID NO: 17)
MSP7: CCCUGUUAAUGGCUACUUUAUUAAA,
and (SEQ ID NO: 18)
MSP8: GCCGCAUAAGGUUCAUGUUCACUAA.
```

11. A composition comprising the siRNA molecule of claim 9 and a pharmaceutically acceptable carrier comprising a polymeric nanoparticle or a liposomal nanoparticle.

12. A method of treating a mammal with a MERS infection comprising administering to said mammal a pharmaceutically effective amount of the composition of claim 11.

13. The method of claim 12, wherein the mammal is a human.

14. The composition of claim 2, wherein if a polymeric nanoparticle carrier is present said carrier comprises a Histidine-Lysine co-polymer (HKP) and if a liposomal nanoparticle carrier is present said carrier comprises a Spermine-Lipid Conjugate (SLiC) and cholesterol.

15. The composition of claim 3, wherein if a polymeric nanoparticle carrier is present said carrier comprises a Histidine-Lysine co-polymer (HKP) and if a liposomal nanoparticle carrier is present said carrier comprises a Spermine-Lipid Conjugate (SLiC) and cholesterol.

16. The composition of claim 4, wherein if a polymeric nanoparticle carrier is present said carrier comprises a Histidine-Lysine co-polymer (HKP) and if a liposomal nanoparticle carrier is present said carrier comprises a Spermine-Lipid Conjugate (SLiC) and cholesterol.

17. A method of treating a mammal with a MERS infection comprising administering to said mammal a pharmaceutically effective amount of the composition of claim 2.

18. A method of treating a mammal with a MERS infection comprising administering to said mammal a pharmaceutically effective amount of the composition of claim 3.

19. A method of treating a mammal with a MERS infection comprising administering to said mammal a pharmaceutically effective amount of the composition of claim 4.

20. A method of treating a mammal with a MERS infection comprising administering to said mammal a pharmaceutically effective amount of the composition of claim 10.

* * * * *